United States Patent
Evans et al.

(10) Patent No.: US 10,227,351 B2
(45) Date of Patent: Mar. 12, 2019

(54) SALT AND POLYMORPHIC FORMS OF (3R,4S)-L-((4-AMINO-5H-PYRROLO[3,2,-D]PYRIMIDIN-7-YL)METHYL)-4(METHYLTHIOMETHYL)PYRODIN-3-OL(MTDIA)

(71) Applicant: VICTORIA LINK LIMITED, Wellington (NZ)

(72) Inventors: Gary Brian Evans, Lower Hutt (NZ); Peter Michael Kelly, Lower Hutt (NZ); Peter Charles Tyler, Wellington (NZ)

(73) Assignee: Victoria Link Limited, Wellington (NZ)

( * ) Notice: Subject to any disclaimer, the term of this patent is extended or adjusted under 35 U.S.C. 154(b) by 0 days.

(21) Appl. No.: 15/993,669

(22) Filed: May 31, 2018

(65) Prior Publication Data

US 2018/0319803 A1 Nov. 8, 2018

Related U.S. Application Data

(62) Division of application No. 14/441,690, filed as application No. PCT/NZ2013/000201 on Nov. 12, 2013, now Pat. No. 9,994,574.

(60) Provisional application No. 61/725,078, filed on Nov. 12, 2012.

(51) Int. Cl.
| | |
|---|---|
| C07D 207/50 | (2006.01) |
| C07D 487/04 | (2006.01) |
| C07D 207/44 | (2006.01) |
| C07D 207/12 | (2006.01) |
| C07D 207/34 | (2006.01) |
| C07C 55/07 | (2006.01) |
| C07C 53/06 | (2006.01) |
| C07C 269/04 | (2006.01) |
| A61K 31/519 | (2006.01) |
| A61P 35/00 | (2006.01) |
| A61P 35/02 | (2006.01) |

(52) U.S. Cl.
CPC ............ *C07D 487/04* (2013.01); *C07C 53/06* (2013.01); *C07C 55/07* (2013.01); *C07C 269/04* (2013.01); *C07D 207/12* (2013.01); *C07D 207/34* (2013.01); *C07D 207/44* (2013.01); *C07D 207/50* (2013.01); *C07B 2200/13* (2013.01)

(58) Field of Classification Search
CPC .................................................. C07D 207/50
See application file for complete search history.

(56) References Cited

U.S. PATENT DOCUMENTS

| | | | |
|---|---|---|---|
| 7,553,839 | B2 | 6/2009 | Evans et al. |
| 8,173,662 | B2 | 5/2012 | Evans et al. |
| 2006/0160765 | A1 | 7/2006 | Evans et al. |
| 2009/0239885 | A1 | 9/2009 | Evans et al. |
| 2010/0222370 | A1 | 9/2010 | Schramm et al. |

FOREIGN PATENT DOCUMENTS

| | | |
|---|---|---|
| WO | 2004018496 A1 | 3/2004 |
| WO | 2007097647 A1 | 8/2007 |

OTHER PUBLICATIONS

Bastin R J et al., entitled "Salt Selection and Optimisation Procedures for Pharmaceutical New Chemical Entities," Organic Process Research & Development 2000, 4, 427-435.
PCT International Preliminary Report on Patentability, dated May 12, 2015, in connection with PCT International Patent Application No. PCT/NZ2013/000201.
Berge S M et al., entitled "Pharmaceutical Salts," Journal of Pharmaceutical Sciences, Jan. 1, 1977, vol. 66, No. 1, 1-19.
Caira M R, entitled "Crystalline Polymorphism of Organic Compounds," Topics in Current Chemistry, vol. 198, Jan. 1, 1998, 163-208.
Kumar L et al., entitled "An overview of automated systems relevant in pharmaceutical salt screening," Drug Discovery Today, vol. 12, No. 23-24, Nov. 29, 2007, 1046-1053.
Australian Examination Report No. 1 dated Feb. 17, 2017 for Australian Patent Application No. 2013341877, 4 pages.
Notice of Reasons for Rejection dated Aug. 1, 2017 for Japanese Patent Application No. P2015-541735, 4 pages.
Communication Supplementary European Search Report dated Mar. 1, 2016 in connection with European Patent Application No. 13852990. 4, 10 pages.
International Search Report dated Feb. 20, 2014 for PCT Application No. PCT/NZ2013/000201.
Written Opinion of the International Searching Authority dated Feb. 20, 2014 for PCT Application No. PCT/NZ2013/000201.

*Primary Examiner* — Susanna Moore
(74) *Attorney, Agent, or Firm* — Amster, Rothstein & Ebenstein LLP

(57) ABSTRACT

The invention relates to salt forms of (3R,4S)-1-((4-amino-5H-pyrrolo[3,2-d]pyrimidin-7-yl)methyl)-4-(methyl-thiomethyl)pyrrolidin-3-ol, as well as polymorphic forms of the salts. The invention further relates to processes for preparing the salt forms and to the use of the salt forms in the treatment of diseases and disorders where it is desirable to inhibit 5'-methylthioadenosine phosphorylase (MTAP).

1 Claim, 25 Drawing Sheets

SALT AND POLYMORPHIC FORMS OF (3R,4S)-L-((4-AMINO-5H-PYRROLO[3,2,-D]PYRIMIDIN-7-YL)METHYL)-4(METHYLTHIOMETHYL)PYRODIN-3-OL(MTDIA)

CROSS-REFERENCE TO RELATED APPLICATIONS

This application is a divisional of U.S. patent application Ser. No. 14/441,690, filed on May 8, 2015, now U.S. Pat. No. 9,994,574 B2, which is a U.S. national stage entry under 35 U.S.C. § 371 of PCT International Patent Application No. PCT/NZ2013/000201, filed on Nov. 12, 2013, which claims the benefit of U.S. Provisional Application No. 61/725,078, filed on Nov. 12, 2012, the contents of all of which are herein incorporated by reference.

TECHNICAL FIELD

This invention relates to salt forms of (3R,4S)-1-((4-amino-5H-pyrrolo[3,2-d]pyrimidin-7-yl)methyl)-4-(methylthiomethyl)pyrrolidin-3-ol, compound (I) (MTDIA), as well as polymorphic forms of the salts. The invention further relates to processes for preparing the salt forms and to the use of the salt forms in the treatment of diseases and disorders where it is desirable to inhibit 5'-methylthioadenosine phosphorylase (MTAP), such as cancer.

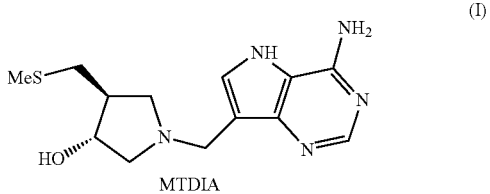

MTDIA (I)

BACKGROUND

5'-Methylthioadenosine phosphorylase (MTAP) functions in the polyamine biosynthesis pathway, in purine salvage in mammals. It catalyses the reversible phosphorolysis of 5'-methylthioadenosine (MTA) to adenine and 5-methylthio-α-D-ribose-1-phosphate (MTR-1P). The adenine formed is subsequently recycled and converted into nucleotides. Essentially, the only source of free adenine in the human cell is a result of the action of these enzymes. The MTR-1P is subsequently converted into methionine by successive enzymatic actions.

MTA is a by-product of the reaction involving the transfer of an aminopropyl group from decarboxylated S-adenosyl methionine to putrescine during the formation of spermidine and spermine. The reactions are catalyzed by spermidine synthase and spermine synthase. The synthases are very sensitive to product inhibition by accumulation of MTA. Therefore, inhibition of MTAP severely limits the polyamine biosynthesis and the salvage pathway for adenine in the cells.

MTAP deficiency due to a genetic deletion has been reported with many malignancies. The loss of MTAP enzyme function in these cells is known to be due to homozygous deletions on chromosome 9 of the closely linked MTAP and p16/MTS1 tumour suppressor gene. As absence of p16/MTS1 is probably responsible for the tumour, the lack of MTAP activity is a consequence of the genetic deletion and is not causative for the cancer. However, the absence of MTAP alters the purine metabolism in these cells so that they are mainly dependent on the de novo pathway for their supply of purines. That makes these cells unusually sensitive to inhibitors like methotrexate and azaserine that block the de novo pathway. Therefore, a combination therapy of methotrexate or azaserine with an MTAP inhibitor will have unusually effective anti-tumour properties.

WO 2004/018496 describes compounds, including MTDIA, which are inhibitors of nucleoside processing enzymes. US 2010/0222370 describes that MTDIA is useful in the treatment of prostate and head and neck cancers.

It is an object of the invention to provide salt forms of (3R,4S)-1-((4-amino-5H-pyrrolo[3,2-d]pyrimidin-7-yl)methyl)-4-(methylthiomethyl)pyrrolidin-3-ol, or to at least provide the public with a useful alternative.

STATEMENTS OF INVENTION

In a first aspect the invention provides a salt form of (3R,4S)-1-((4-amino-5H-pyrrolo[3,2-d]pyrimidin-7-yl)methyl)-4-(methylthiomethyl)pyrrolidin-3-ol, selected from the group consisting of (3R,4S)-1-((4-amino-5H-pyrrolo[3,2-d]pyrimidin-7-yl)methyl)-4-(methylthiomethyl)pyrrolidin-3-phosphate, (3R,4S)-1-((4-amino-5H-pyrrolo[3,2-d]pyrimidin-7-yl)methyl)-4-(methylthiomethyl)pyrrolidin-3-ol formate, (3R,4S)-1-((4-amino-5H-pyrrolo[3,2-d]pyrimidin-7-yl)methyl)-4-(methylthiomethyl)pyrrolidin-3-ol oxalate and (3R,4S)-1-((4-amino-5H-pyrrolo[3,2-d]pyrimidin-7-yl)methyl)-4-(methylthiomethyl)pyrrolidin-3-ol sulfate.

In another aspect the invention provides a crystalline salt form of (3R,4S)-1-((4-amino-5H-pyrrolo[3,2-d]pyrimidin-7-yl)methyl)-4-(methylthiomethyl)pyrrolidin-3-ol, selected from the group consisting of (3R,4S)-1-((4-amino-5H-pyrrolo[3,2-d]pyrimidin-7-yl)methyl)-4-(methylthiomethyl)pyrrolidin-3-ol phosphate, (3R,4S)-1-((4-amino-5H-pyrrolo[3,2-d]pyrimidin-7-yl)methyl)-4-(methylthiomethyl)pyrrolidin-3-ol formate, (3R,4S)-1-((4-amino-5H-pyrrolo[3,2-d]pyrimidin-7-yl)methyl)-4-(methylthiomethyl)pyrrolidin-3-ol oxalate and (3R,4S)-1-((4-amino-5H-pyrrolo[3,2-d]pyrimidin-7-yl)methyl)-4-(methylthiomethyl)pyrrolidin-3-ol sulfate.

In another aspect the invention provides (3R,4S)-1-((4-amino-5H-pyrrolo[3,2-d]pyrimidin-7-yl)methyl)-4-(methylthiomethyl)pyrrolidin-3-ol phosphate, a compound of formula (Ia):

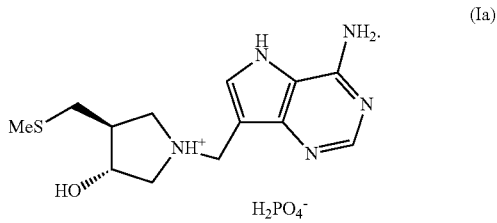

(Ia)

In another aspect the invention provides crystalline (3R,4S)-1-((4-amino-5H-pyrrolo[3,2-d]pyrimidin-7-yl)methyl)-4-(methylthiomethyl)pyrrolidin-3-ol phosphate.

In still another aspect the invention provides crystalline (3R,4S)-1-((4-amino-5H-pyrrolo[3,2-d]pyrimidin-7-yl)methyl)-4-(methylthiomethyl)pyrrolidin-3-ol phosphate of Form D characterised by X-ray power diffraction peaks at the following 2 theta angles: about 5.38, 7.10, 8.93, 10.87, 13.06, 14.31, 15.81, 17.59, 17.92, 19.97, 21.53, 22.76, 26.00, 27.06, 27.79, 28.95 and 29.97 degrees 2 theta±0.05 degrees 2 theta, which correspond, respectively, to the following d-spacings: about 19.1, 14.4, 11.49, 9.44, 7.87, 7.18, 6.50, 5.85, 5.74, 5.16, 4.79, 4.53, 3.977, 3.823, 3.725, 3.579 and 3.459 Å.

Preferably the crystalline (3R,4S)-1-((4-amino-5H-pyrrolo[3,2-d]pyrimidin-7-yl)methyl)-4-(methylthiomethyl) pyrrolidin-3-ol phosphate of Form D is further characterised by one or more additional X-ray power diffraction peaks at the following 2 theta angles: about 14.57, 15.32, 16.50, 19.07, 20.17, 20.77, 21.78, 22.22, 23.12, 24.84, 25.75, 26.31, 28.14, 28.57, 29.35, 30.50, 30.91, 31.35, 32.64, 32.09, 34.17, 33.33 degrees 2 theta±0.05 degrees 2 theta, which correspond, respectively, to the following d-spacings: about 7.05, 6.71, 6.23, 5.40, 5.11, 4.96, 4.73, 4.64, 4.46, 4.159, 4.014, 3.931, 3.679, 3.625, 3.531, 3.401, 3.357, 3.311, 3.183, 3.236, 3.045, 3.119 Å.

In a further aspect the invention provides crystalline (3R,4S)-1-((4-amino-5H-pyrrolo[3,2-d]pyrimidin-7-yl)methyl)-4-(methylthiomethyl)pyrrolidin-3-ol phosphate Form D having an X-ray power diffraction pattern substantially as shown in FIG. 3(a).

In still another aspect the invention provides crystalline (3R,4S)-1-((4-amino-5H-pyrrolo[3,2-d]pyrimidin-7-yl)methyl)-4-(methylthiomethyl)pyrrolidin-3-ol phosphate of Form E characterised by X-ray power diffraction peaks at the following 2 theta angles: about 5.26, 7.01, 8.69, 10.58, 15.95, 17.26, 17.57, 21.27, 21.60, 22.75, 25.64, 26.88, 28.86, 29.99 and 30.75 degrees 2 theta±0.05 degrees 2 theta, which correspond, respectively, to the following d-spacings: about 19.5, 14.6, 11.81, 9.70, 6.45, 5.96, 5.86, 4.85, 4.77, 4.54, 4.031, 3.849, 3.589, 3.457 and 3.374 Å.

Preferably the crystalline (3R,4S)-1-((4-amino-5H-pyrrolo[3,2-d]pyrimidin-7-yl)methyl)-4-(methylthiomethyl) pyrrolidin-3-ol phosphate of Form E is further characterised by one or more additional X-ray power diffraction peaks at the following 2 theta angles: about 8.91, 12.56, 16.76, 17.84, 19.36, 20.14, 20.86, 22.09, 22.53, 23.03, 24.14, 25.95, 26.16, 26.63, 27.72, 29.35, 30.22, 31.11, 31.57, 32.38, 33.04, 33.38, 33.93 degrees 2 theta±0.05 degrees 2 theta, which correspond, respectively, to the following d-spacings: about 11.52, 8.18, 6.14, 5.77, 5.32, 5.12, 4.94, 4.67, 4.58, 4.48, 4.278, 3.984, 3.952, 3.884, 3.734, 3.531, 3.431, 3.336, 3.288, 3.208, 3.146, 3.115, 3.066 Å.

In a further aspect the invention provides crystalline (3R,4S)-1-((4-amino-5H-pyrrolo[3,2-d]pyrimidin-7-yl)methyl)-4-(methylthiomethyl)pyrrolidin-3-ol phosphate Form E having an X-ray power diffraction pattern substantially as shown in FIG. 4(a).

In still another aspect the invention provides crystalline (3R,4S)-1-((4-amino-5H-pyrrolo[3,2-d]pyrimidin-7-yl)methyl)-4-(methylthiomethyl)pyrrolidin-3-ol phosphate of Form F characterised by X-ray power diffraction peaks at the following 2 theta angles: about 5.25, 7.00, 8.73, 10.67, 15.82, 16.04, 17.52, 17.75, 20.13, 20.77, 21.36, 21.72, 22.79, 25.70, 26.10, 28.55, 29.56, 30.52, 31.43 and 32.42 degrees 2 theta±0.05 degrees 2 theta, which correspond, respectively, to the following d-spacings: about 19.5, 14.7, 11.76, 9.62, 6.50, 6.41, 5.87, 5.80, 5.12, 4.97, 4.83, 4.75, 4.53, 4.022, 3.962, 3.627, 3.506, 3.398, 3.303 and 3.204 Å.

Preferably the crystalline (3R,4S)-1-((4-amino-5H-pyrrolo[3,2-d]pyrimidin-7-yl)methyl)-4-(methylthiomethyl) pyrrolidin-3-ol phosphate of Form F is further characterised by one or more additional X-ray power diffraction peaks at the following 2 theta angles: about 8.92, 12.69, 14.19, 15.14, 16.68, 19.21, 22.09, 23.60, 24.35, 24.80, 26.81, 27.00, 27.81, 29.01, 29.88, 32.12, 32.95, 33.68, 34.08, 35.08, 35.84, 36.58, 37.32, 39.18, 40.37, 40.79, 41.84, 42.56, 43.62, 44.51, 46.14, 46.52, 47.00, 48.24, 49.02, 49.54 degrees 2 theta±0.05 degrees 2 theta, which correspond, respectively, to the following d-spacings: about 11.50, 8.09, 7.25, 6.79, 6.17, 5.36, 4.67, 4.374, 4.241, 4.165, 3.859, 3.832, 3.722, 3.571, 3.469, 3.233, 3.154, 3.088, 3.052, 2.968, 2.907, 2.850, 2.795, 2.668, 2.592, 2.567, 2.505, 2.464, 2.408, 2.362, 2.283, 2.265, 2.243, 2.189, 2.156, 2.135 Å.

In a further aspect the invention provides crystalline (3R,4S)-1-((4-amino-5H-pyrrolo[3,2-d]pyrimidin-7-yl)methyl)-4-(methylthiomethyl)pyrrolidin-3-ol phosphate Form F having an X-ray power diffraction pattern substantially as shown in FIG. 5(a).

In still another aspect the invention provides crystalline (3R,4S)-1-((4-amino-5H-pyrrolo[3,2-d]pyrimidin-7-yl)methyl)-4-(methylthiomethyl)pyrrolidin-3-ol oxalate characterised by X-ray power diffraction peaks at the following 2 theta angles: about 6.22, 12.35, 13.54, 18.23, 20.47, 21.94, 24.22 and 29.44 degrees 2 theta±0.05 degrees 2 theta, which correspond, respectively, to the following d-spacings: about 16.5, 8.32, 7.59, 5.65, 5.03, 4.70, 4.263 and 3.520 Å.

Preferably the crystalline (3R,4S)-1-((4-amino-5H-pyrrolo[3,2-d]pyrimidin-7-yl)methyl)-4-(methylthiomethyl) pyrrolidin-3-ol oxalate is further characterised by one or more additional X-ray power diffraction peaks at the following 2 theta angles: about 14.94, 15.72, 19.11, 22.54, 30.07, 31.11, 32.06, 32.71, 33.90 degrees 2 theta±0.05 degrees 2 theta, which correspond, respectively, to the following d-spacings: about 6.88, 6.54, 5.39, 4.58, 3.448, 3.336, 3.239, 3.177, 3.068 Å.

In a further aspect the invention provides crystalline (3R,4S)-1-((4-amino-5H-pyrrolo[3,2-d]pyrimidin-7-yl)methyl)-4-(methylthiomethyl)pyrrolidin-3-ol oxalate having an X-ray power diffraction pattern substantially as shown in FIG. 1(a).

In still another aspect the invention provides crystalline (3R,4S)-1-((4-amino-5H-pyrrolo[3,2-d]pyrimidin-7-yl)methyl)-4-(methylthiomethyl)pyrrolidin-3-ol formate characterised by X-ray power diffraction peaks at the following 2 theta angles: about 8.11, 16.30, 20.68, 24.85, 25.70, 26.03, 28.00, 32.23 and 33.02 degrees 2 theta±0.05 degrees 2 theta, which correspond, respectively, to the following d-spacings: about 12.65, 6.31, 4.98, 4.157, 4.022, 3.972, 3.698, 3.223 and 3.147 Å.

Preferably the crystalline (3R,4S)-1-((4-amino-5H-pyrrolo[3,2-d]pyrimidin-7-yl)methyl)-4-(methylthiomethyl) pyrrolidin-3-ol formate is further characterised by one or more additional X-ray power diffraction peaks at the following 2 theta angles: about 10.34, 13.66, 17.54, 17.95, 18.83, 21.32, 21.71, 23.17, 24.63, 27.13, 27.57, 28.51, 28.77, 30.33, 31.05, 31.24, 33.45, 34.24, 34.52, 35.57, 35.99, 36.66, 36.93, 38.15, 38.91, 39.94, 40.47, 41.45, 42.17, 42.75, 44.36, 45.15, 46.27, 46.50, 47.36, 48.49, 49.20, 50.12 degrees 2 theta±0.05 degrees 2 theta, which correspond, respectively, to the following d-spacings: about 9.93, 7.52, 5.87, 5.74, 5.47, 4.84, 4.75, 4.45, 4.194, 3.814, 3.754, 3.632, 3.600, 3.420, 3.342, 3.322, 3.108, 3.039, 3.014, 2.929, 2.896, 2.845, 2.825, 2.737, 2.686, 2.619, 2.586, 2.528, 2.486, 2.454, 2.369, 2.330, 2.277, 2.266, 2.227, 2.178, 2.149, 2.112 Å.

In a further aspect the invention provides crystalline (3R,4S)-1-((4-amino-5H-pyrrolo[3,2-d]pyrimidin-7-yl)methyl)-4-(methylthiomethyl)pyrrolidin-3-ol formate having an X-ray power diffraction pattern substantially as shown in FIG. 6(a).

In still another aspect the invention provides crystalline (3R,4S)-1-((4-amino-5H-pyrrolo[3,2-d]pyrimidin-7-yl)methyl)-4-(methylthiomethyl)pyrrolidin-3-ol sulfate characterised by X-ray power diffraction peaks at the following 2 theta angles: about 5.75, 10.33, 13.14, 15.41, 15.90, 17.61, 18.32, 21.43, 24.30, 26.15, 26.76, 27.67, 30.28, 30.97, 31.52 and 32.27 degrees 2 theta±0.05 degrees 2 theta, which correspond, respectively, to the following d-spacings: about 17.8, 9.94, 7.82, 6.67, 6.47, 5.84, 5.62, 4.81, 4.25, 3.954, 3.866, 3.741, 3.425, 3.35, 3.293 and 3.219 Å.

Preferably the crystalline (3R,4S)-1-((4-amino-5H-pyrrolo[3,2-d]pyrimidin-7-yl)methyl)-4-(methylthiomethyl)pyrrolidin-3-ol sulfate is further characterised by one or more additional X-ray power diffraction peaks at the following 2 theta angles: about 19.14, 20.28, 20.87, 22.26, 24.64, 29.37, 33.24 degrees 2 theta±0.05 degrees 2 theta, which correspond, respectively, to the following d-spacings: about 5.38, 5.08, 4.94, 4.63, 4.192, 3.529, 3.127 Å.

In a further aspect the invention provides crystalline (3R,4S)-1-((4-amino-5H-pyrrolo[3,2-d]pyrimidin-7-yl)methyl)-4-(methylthiomethyl)pyrrolidin-3-ol sulfate having an X-ray power diffraction pattern substantially as shown in FIG. 2(*a*).

In still another aspect the invention provides (3R,4S)-1-((4-amino-5H-pyrrolo[3,2-d]pyrimidin-7-yl)methyl)-4-(methylthiomethyl)pyrrolidin-3-ol phosphate which exhibits an endotherm at a range of about 165° C. to about 185° C. as measured by differential scanning calorimetry.

In still another aspect the invention provides (3R,4S)-1-((4-amino-5H-pyrrolo[3,2-d]pyrimidin-7-yl)methyl)-4-(methylthiomethyl)pyrrolidin-3-ol phosphate of Form D, having a differential scanning calorimetry thermogram substantially as shown in FIG. 3(*c*).

In still another aspect the invention provides (3R,4S)-1-((4-amino-5H-pyrrolo[3,2-d]pyrimidin-7-yl)methyl)-4-(methylthiomethyl)pyrrolidin-3-ol phosphate of Form E, having a differential scanning calorimetry thermogram substantially as shown in FIG. 4(*c*).

In still another aspect the invention provides (3R,4S)-1-((4-amino-5H-pyrrolo[3,2-d]pyrimidin-7-yl)methyl)-4-(methylthiomethyl)pyrrolidin-3-ol phosphate of Form F, having a differential scanning calorimetry thermogram substantially as shown in FIG. 5(*c*).

In still another aspect the invention provides (3R,4S)-1-((4-amino-5H-pyrrolo[3,2-d]pyrimidin-7-yl)methyl)-4-(methylthiomethyl)pyrrolidin-3-ol oxalate which exhibits an endotherm at about 137.04° C. as measured by differential scanning calorimetry.

In still another aspect the invention provides (3R,4S)-1-((4-amino-5H-pyrrolo[3,2-d]pyrimidin-7-yl)methyl)-4-(methylthiomethyl)pyrrolidin-3-ol oxalate, having a differential scanning calorimetry thermogram substantially as shown in FIG. 1(*b*).

In still another aspect the invention provides (3R,4S)-1-((4-amino-5H-pyrrolo[3,2-d]pyrimidin-7-yl)methyl)-4-(methylthiomethyl)pyrrolidin-3-ol formate which exhibits an endotherm at about 179.54° C. as measured by differential scanning calorimetry.

In still another aspect the invention provides (3R,4S)-1-((4-amino-5H-pyrrolo[3,2-d]pyrimidin-7-yl)methyl)-4-(methylthiomethyl)pyrrolidin-3-ol formate, having a differential scanning calorimetry thermogram substantially as shown in FIG. 6(*c*).

Preferably the (3R,4S)-1-((4-amino-5H-pyrrolo[3,2-d]pyrimidin-7-yl)methyl)-4-(methylthiomethyl)pyrrolidin-3-ol phosphate, (3R,4S)-1-((4-amino-5H-pyrrolo[3,2-d]pyrimidin-7-yl)methyl)-4-(methylthiomethyl)pyrrolidin-3-ol formate, (3R,4S)-1-((4-amino-5H-pyrrolo[3,2-d]pyrimidin-7-yl)methyl)-4-(methylthiomethyl)pyrrolidin-3-ol oxalate or (3R,4S)-1-((4-amino-5H-pyrrolo[3,2-d]pyrimidin-7-yl)methyl)-4-(methylthiomethyl)pyrrolidin-3-ol sulfate is crystalline.

In a further aspect the invention provides a pharmaceutical composition comprising (3R,4S)-1-((4-amino-5H-pyrrolo[3,2-d]pyrimidin-7-yl)methyl)-4-(methylthiomethyl)pyrrolidin-3-ol phosphate, (3R,4S)-1-((4-amino-5H-pyrrolo[3,2-d]pyrimidin-7-yl)methyl)-4-(methylthiomethyl)pyrrolidin-3-ol formate, (3R,4S)-1-((4-amino-5H-pyrrolo[3,2-d]pyrimidin-7-yl)methyl)-4-(methylthiomethyl)pyrrolidin-3-ol oxalate or (3R,4S)-1-((4-amino-5H-pyrrolo[3,2-d]pyrimidin-7-yl)methyl)-4-(methylthiomethyl)pyrrolidin-3-ol sulfate, preferably (3R,4S)-1-((4-amino-5H-pyrrolo[3,2-d]pyrimidin-7-yl)methyl)-4-(methylthiomethyl)pyrrolidin-3-ol phosphate, more preferably crystalline (3R,4S)-1-((4-amino-5H-pyrrolo[3,2-d]pyrimidin-7-yl)methyl)-4-(methylthiomethyl)pyrrolidin-3-ol phosphate, and at least one pharmaceutically acceptable excipient.

Preferably the crystalline (3R,4S)-1-((4-amino-5H-pyrrolo[3,2-d]pyrimidin-7-yl)methyl)-4-(methylthiomethyl)pyrrolidin-3-ol phosphate is characterised by X-ray power diffraction peaks at the following 2 theta angles: about 5.38, 7.10, 8.93, 10.87, 13.06, 14.31, 15.81, 17.59, 17.92, 19.97, 21.53, 22.76, 26.00, 27.06, 27.79, 28.95 and 29.97 degrees 2 theta±0.05 degrees 2 theta, which correspond, respectively, to the following d-spacings: about 19.1, 14.4, 11.49, 9.44, 7.87, 7.18, 6.50, 5.85, 5.74, 5.16, 4.79, 4.53, 3.977, 3.823, 3.725, 3.579 and 3.459 Å. More preferably the crystalline (3R,4S)-1-((4-amino-5H-pyrrolo[3,2-d]pyrimidin-7-yl)methyl)-4-(methylthiomethyl)pyrrolidin-3-ol phosphate is further characterised by one or more additional X-ray power diffraction peaks at the following 2 theta angles: about 14.57, 15.32, 16.50, 19.07, 20.17, 20.77, 21.78, 22.22, 23.12, 24.84, 25.75, 26.31, 28.14, 28.57, 29.35, 30.50, 30.91, 31.35, 32.64, 32.09, 34.17, 33.33 degrees 2 theta±0.05 degrees 2 theta, which correspond, respectively, to the following d-spacings: about 7.05, 6.71, 6.23, 5.40, 5.11, 4.96, 4.73, 4.64, 4.46, 4.159, 4.014, 3.931, 3.679, 3.625, 3.531, 3.401, 3.357, 3.311, 3.183, 3.236, 3.045, 3.119 Å.

Alternatively preferably the crystalline (3R,4S)-1-((4-amino-5H-pyrrolo[3,2-d]pyrimidin-7-yl)methyl)-4-(methylthiomethyl)pyrrolidin-3-ol phosphate is characterised by X-ray power diffraction peaks at the following 2 theta angles about 5.26, 7.01, 8.69, 10.58, 15.95, 17.26, 17.57, 21.27, 21.60, 22.75, 25.64, 26.88, 28.86, 29.99 and 30.75 degrees 2 theta±0.05 degrees 2 theta, which correspond, respectively, to the following d-spacings: about 19.5, 14.6, 11.81, 9.70, 6.45, 5.96, 5.86, 4.85, 4.77, 4.54, 4.031, 3.849, 3.589, 3.457 and 3.374 Å. More preferably the crystalline (3R,4S)-1-((4-amino-5H-pyrrolo[3,2-d]pyrimidin-7-yl)methyl)-4-(methylthiomethyl)pyrrolidin-3-ol phosphate is further characterised by one or more additional X-ray power diffraction peaks at the following 2 theta angles: about 8.91, 12.56, 16.76, 17.84, 19.36, 20.14, 20.86, 22.09, 22.53, 23.03, 24.14, 25.95, 26.16, 26.63, 27.72, 29.35, 30.22, 31.11, 31.57, 32.38, 33.04, 33.38, 33.93 degrees 2 theta±0.05 degrees 2 theta, which correspond, respectively, to the following d-spacings: about 11.52, 8.18, 6.14, 5.77, 5.32, 5.12, 4.94, 4.67, 4.58, 4.48, 4.278, 3.984, 3.952, 3.884, 3.734, 3.531, 3.431, 3.336, 3.288, 3.208, 3.146, 3.115, 3.066 Å.

Alternatively preferably the crystalline (3R,4S)-1-((4-amino-5H-pyrrolo[3,2-d]pyrimidin-7-yl)methyl)-4-(methylthiomethyl)pyrrolidin-3-ol phosphate is characterised by X-ray power diffraction peaks at the following 2 theta angles: about 5.25, 7.00, 8.73, 10.67, 15.82, 16.04, 17.52, 17.75, 20.13, 20.77, 21.36, 21.72, 22.79, 25.70, 26.10, 28.55, 29.56, 30.52, 31.43 and 32.42 degrees 2 theta±0.05 degrees 2 theta, which correspond, respectively, to the following d-spacings: about 19.5, 14.7, 11.76, 9.62, 6.50, 6.41, 5.87, 5.80, 5.12, 4.97, 4.83, 4.75, 4.53, 4.022, 3.962, 3.627, 3.506, 3.398, 3.303 and 3.204 Å. More preferably the crystalline (3R,4S)-1-(4-amino-5H-pyrrolo[3,2-d]pyrimidin-7-yl)methyl)-4-(methylthiomethyl)pyrrolidin-3-ol phosphate is further characterised by one or more additional X-ray power diffraction peaks at the following 2 theta angles: about 8.92, 12.69, 14.19, 15.14, 16.68, 19.21, 22.09, 23.60, 24.35, 24.80, 26.81, 27.00, 27.81, 29.01, 29.88, 32.12, 32.95, 33.68, 34.08, 35.08, 35.84, 36.58, 37.32, 39.18, 40.37, 40.79, 41.84, 42.56, 43.62, 44.51, 46.14, 46.52, 47.00, 48.24, 49.02, 49.54 degrees 2 theta±0.05 degrees 2 theta, which correspond, respectively, to the following d-spacings: about 11.50, 8.09, 7.25, 6.79, 6.17, 5.36, 4.67, 4.374, 4.241, 4.165, 3.859, 3.832, 3.722, 3.571, 3.469, 3.233, 3.154, 3.088, 3.052, 2.968, 2.907, 2.850, 2.795, 2.668, 2.592, 2.567, 2.505, 2.464, 2.408, 2.362, 2.283, 2.265, 2.243, 2.189, 2.156, 2.135 Å.

In a yet another aspect, the invention provides a method of treating a disease or disorder in which it is desirable to inhibit MTAP, comprising administering an effective amount of (3R,4S)-1-((4-amino-5H-pyrrolo[3,2-d]pyrimidin-7-yl)methyl)-4-(methylthiomethyl)pyrrolidin-3-ol phosphate or (3R,4S)-1-((4-amino-5H-pyrrolo[3,2-d]pyrimidin-7-yl)methyl)-4-(methylthiomethyl)pyrrolidin-3-ol formate or (3R,4S)-1-((4-amino-5H-pyrrolo[3,2-d]pyrimidin-7-yl)methyl)-4-(methylthiomethyl)pyrrolidin-3-ol oxalate or (3R,4S)-1-((4-amino-5H-pyrrolo[3,2-d]pyrimidin-7-yl)methyl)-4-(methylthiomethyl)pyrrolidin-3-ol sulfate, preferably (3R,4S)-1-((4-amino-5H-pyrrolo[3,2-d]pyrimidin-7-yl)methyl)-4-(methylthiomethyl)pyrrolidin-3-ol phosphate, to a patient in need thereof.

In still another aspect the invention provides the use of (3R,4S)-1-((4-amino-5H-pyrrolo[3,2-d]pyrimidin-7-yl)methyl)-4-(methylthiomethyl)pyrrolidin-3-ol phosphate or (3R,4S)-1-((4-amino-5H-pyrrolo[3,2-d]pyrimidin-7-yl)methyl)-4-(methylthiomethyl)pyrrolidin-3-ol formate or (3R,4S)-1-((4-amino-5H-pyrrolo[3,2-d]pyrimidin-7-yl)methyl)-4-(methylthiomethyl)pyrrolidin-3-ol oxalate or (3R,4S)-1-((4-amino-5H-pyrrolo[3,2-d]pyrimidin-7-yl)methyl)-4-(methylthiomethyl)pyrrolidin-3-ol sulfate, preferably (3R,4S)-1-((4-amino-5H-pyrrolo[3,2-d]pyrimidin-7-yl)methyl)-4-(methylthiomethyl)pyrrolidin-3-ol phosphate, as a medicament.

In still another aspect the invention provides the use of (3R,4S)-1-((4-amino-5H-pyrrolo[3,2-d]pyrimidin-7-yl)methyl)-4-(methylthiomethyl)pyrrolidin-3-ol phosphate or (3R,4S)-1-((4-amino-5H-pyrrolo[3,2-d]pyrimidin-7-yl)methyl)-4-(methylthiomethyl)pyrrolidin-3-ol formate or (3R,4S)-1-((4-amino-5H-pyrrolo[3,2-d]pyrimidin-7-yl)methyl)-4-(methylthiomethyl)pyrrolidin-3-ol oxalate or (3R,4S)-1-((4-amino-5H-pyrrolo[3,2-d]pyrimidin-7-yl)methyl)-4-(methylthiomethyl)pyrrolidin-3-ol sulfate, preferably (3R,4S)-1-((4-amino-5H-pyrrolo[3,2-d]pyrimidin-7-yl)methyl)-4-(methylthiomethyl)pyrrolidin-3-ol phosphate, in the manufacture of a medicament.

In still another aspect the invention provides the use of (3R,4S)-1-((4-amino-5H-pyrrolo[3,2-d]pyrimidin-7-yl)methyl)-4-(methylthiomethyl)pyrrolidin-3-ol phosphate or (3R,4S)-1-((4-amino-5H-pyrrolo[3,2-d]pyrimidin-7-yl)methyl)-4-(methylthiomethyl)pyrrolidin-3-ol formate or (3R,4S)-1-((4-amino-5H-pyrrolo[3,2-d]pyrimidin-7-yl)methyl)-4-(methylthiomethyl)pyrrolidin-3-ol oxalate or (3R,4S)-1-((4-amino-5H-pyrrolo[3,2-d]pyrimidin-7-yl)methyl)-4-(methylthiomethyl)pyrrolidin-3-ol sulfate, preferably (3R,4S)-1-((4-amino-5H-pyrrolo[3,2-d]pyrimidin-7-yl)methyl)-4-(methylthiomethyl)pyrrolidin-3-ol phosphate, in the manufacture of a medicament for treating a disease or disorder in which it is desirable to inhibit MTAP.

In still another aspect the invention provides a pharmaceutical composition comprising (3R,4S)-1-(4-amino-5H-pyrrolo[3,2-d]pyrimidin-7-yl)methyl)-4-(methylthiomethyl) pyrrolidin-3-ol phosphate or (3R,4S)-1-((4-amino-5H-pyrrolo[3,2-d]pyrimidin-7-yl)methyl)-4-(methylthiomethyl) pyrrolidin-3-ol formate or (3R,4S)-1-((4-amino-5H-pyrrolo [3,2-d]pyrimidin-7-yl)methyl)-4-(methylthiomethyl) pyrrolidin-3-ol oxalate or (3R,4S)-1-((4-amino-5H-pyrrolo [3,2-d]pyrimidin-7-yl)methyl)-4-(methylthiomethyl) pyrrolidin-3-ol sulfate, preferably (3R,4S)-1-((4-amino-5H-pyrrolo[3,2-d]pyrimidin-7-yl)methyl)-4-(methylthiomethyl) pyrrolidin-3-ol phosphate, for use in treating a disease or disorder in which it is desirable to inhibit MTAP.

Preferably the (3R,4S)-1-((4-amino-5H-pyrrolo[3,2-d]pyrimidin-7-yl)methyl)-4-(methylthiomethyl)pyrrolidin-3-ol phosphate is crystalline (3R,4S)-1-((4-amino-5H-pyrrolo[3,2-d]pyrimidin-7-yl)methyl)-4-(methylthiomethyl)pyrrolidin-3-ol phosphate.

Preferably the crystalline (3R,4S)-1-((4-amino-5H-pyrrolo[3,2-d]pyrimidin-7-yl)methyl)-4-(methylthiomethyl) pyrrolidin-3-ol phosphate is characterised by X-ray power diffraction peaks at the following 2 theta angles: about 5.38, 7.10, 8.93, 10.87, 13.06, 14.31, 15.81, 17.59, 17.92, 19.97, 21.53, 22.76, 26.00, 27.06, 27.79, 28.95 and 29.97 degrees 2 theta±0.05 degrees 2 theta, which correspond, respectively, to the following d-spacings: about 19.1, 14.4, 11.49, 9.44, 7.87, 7.18, 6.50, 5.85, 5.74, 5.16, 4.79, 4.53, 3.977, 3.823, 3.725, 3.579 and 3.459 Å. More preferably the crystalline (3R,4S)-1-((4-amino-5H-pyrrolo[3,2-d]pyrimidin-7-yl)methyl)-4-(methylthiomethyl)pyrrolidin-3-ol phosphate is further characterised by one or more additional X-ray power diffraction peaks at the following 2 theta angles: about 14.57, 15.32, 16.50, 19.07, 20.17, 20.77, 21.78, 22.22, 23.12, 24.84, 25.75, 26.31, 28.14, 28.57, 29.35, 30.50, 30.91, 31.35, 32.64, 32.09, 34.17, 33.33 degrees 2 theta±0.05 degrees 2 theta, which correspond, respectively, to the following d-spacings: about 7.05, 6.71, 6.23, 5.40, 5.11, 4.96, 4.73, 4.64, 4.46, 4.159, 4.014, 3.931, 3.679, 3.625, 3.531, 3.401, 3.357, 3.311, 3.183, 3.236, 3.045, 3.119 Å.

Alternatively preferably the crystalline (3R,4S)-1-((4-amino-5H-pyrrolo[3,2-d]pyrimidin-7-yl)methyl)-4-(methylthiomethyl)pyrrolidin-3-ol phosphate is characterised by X-ray power diffraction peaks at the following 2 theta angles about 5.26, 7.01, 8.69, 10.58, 15.95, 17.26, 17.57, 21.27, 21.60, 22.75, 25.64, 26.88, 28.86, 29.99 and 30.75 degrees 2 theta±0.05 degrees 2 theta, which correspond, respectively, to the following d-spacings: about 19.5, 14.6, 11.81, 9.70, 6.45, 5.96, 5.86, 4.85, 4.77, 4.54, 4.031, 3.849, 3.589, 3.457 and 3.374 Å. More preferably the crystalline (3R,4S)-1-((4-amino-5H-pyrrolo[3,2-d]pyrimidin-7-yl)methyl)-4-(methylthiomethyl)pyrrolidin-3-ol phosphate is further characterised by one or more additional X-ray power diffraction peaks at the following 2 theta angles: about 8.91, 12.56, 16.76, 17.84, 19.36, 20.14, 20.86, 22.09, 22.53, 23.03, 24.14, 25.95, 26.16, 26.63, 27.72, 29.35, 30.22, 31.11, 31.57, 32.38, 33.04, 33.38, 33.93 degrees 2 theta±0.05 degrees 2 theta, which correspond, respectively, to the following d-spacings: about 11.52, 8.18, 6.14, 5.77, 5.32, 5.12, 4.94, 4.67, 4.58, 4.48, 4.278, 3.984, 3.952, 3.884, 3.734, 3.531, 3.431, 3.336, 3.288, 3.208, 3.146, 3.115, 3.066 Å.

Alternatively preferably the crystalline (3R,4S)-1-((4-amino-5H-pyrrolo[3,2-d]pyrimidin-7-yl)methyl)-4-(methylthiomethyl)pyrrolidin-3-ol phosphate is characterised by X-ray power diffraction peaks at the following 2 theta angles: about 5.25, 7.00, 8.73, 10.67, 15.82, 16.04, 17.52, 17.75, 20.13, 20.77, 21.36, 21.72, 22.79, 25.70, 26.10, 28.55, 29.56, 30.52, 31.43 and 32.42 degrees 2 theta±0.05 degrees 2 theta, which correspond, respectively, to the following d-spacings: about 19.5, 14.7, 11.76, 9.62, 6.50, 6.41, 5.87, 5.80, 5.12, 4.97, 4.83, 4.75, 4.53, 4.022, 3.962, 3.627, 3.506, 3.398, 3.303 and 3.204 Å. More preferably the crystalline (3R,4S)-1-((4-amino-5H-pyrrolo[3,2-d]pyrimidin-7-yl)methyl)-4-(methylthiomethyl)pyrrolidin-3-ol phosphate is further characterised by one or more additional X-ray power diffraction peaks at the following 2 theta angles: about 8.92, 12.69, 14.19, 15.14, 16.68, 19.21, 22.09, 23.60, 24.35, 24.80, 26.81, 27.00, 27.81, 29.01, 29.88, 32.12, 32.95, 33.68, 34.08, 35.08, 35.84, 36.58, 37.32, 39.18, 40.37, 40.79, 41.84, 42.56, 43.62, 44.51, 46.14, 46.52, 47.00, 48.24, 49.02, 49.54 degrees 2 theta±0.05 degrees 2 theta, which correspond, respectively, to the following d-spacings: about 11.50, 8.09, 7.25, 6.79, 6.17, 5.36, 4.67, 4.374, 4.241, 4.165, 3.859, 3.832, 3.722, 3.571, 3.469, 3.233, 3.154, 3.088, 3.052, 2.968, 2.907, 2.850, 2.795, 2.668, 2.592, 2.567, 2.505, 2.464, 2.408, 2.362, 2.283, 2.265, 2.243, 2.189, 2.156, 2.135 Å.

Preferably the disease or disorder is cancer, e.g. head and neck cancers, lung cancer, breast cancer, colon cancer, cervical cancer or prostate cancer.

The (3R,4S)-1-((4-amino-5H-pyrrolo[3,2-d]pyrimidin-7-yl)methyl)-4-(methylthiomethyl)pyrrolidin-3-ol phosphate or (3R,4S)-1-((4-amino-5H-pyrrolo[3,2-d]pyrimidin-7-yl)methyl)-4-(methylthiomethyl)pyrrolidin-3-ol formate or (3R,4S)-1-((4-amino-5H-pyrrolo[3,2-d]pyrimidin-7-yl)methyl)-4-(methylthiomethyl)pyrrolidin-3-ol oxalate or (3R,4S)-1-((4-amino-5H-pyrrolo[3,2-d]pyrimidin-7-yl)methyl)-4-(methylthiomethyl)pyrrolidin-3-ol sulfate may be administered with a second compound, e.g. methylthioadenosine. The compounds may be administered separately, sequentially or together.

In another aspect the invention provides a process for the preparation of crystalline (3R,4S)-1-((4-amino-5H-pyrrolo[3,2-d]pyrimidin-7-yl)methyl)-4-(methylthiomethyl)pyrrolidin-3-ol phosphate, including the steps:

(a) preparing a solution of (3R,4S)-1-((4-amino-5H-pyrrolo[3,2-d]pyrimidin-7-yl)methyl)-4-(methylthiomethyl) pyrrolidin-3-ol phosphate in water;

(b) adding an alcohol, methyl ethyl ketone, tetrahydrofuran or acetone to the solution, to form crystals of (3R,4S)-1-((4-amino-5H-pyrrolo[3,2-d]pyrimidin-7-yl)methyl)-4-(methylthiomethyl)pyrrolidin-3-ol phosphate; and (c) isolating the crystals of (3R,4S)-1-((4-amino-5H-pyrrolo[3,2-d]pyrimidin-7-yl)methyl)-4-(methylthiomethyl) pyrrolidin-3-ol phosphate.

Preferably an alcohol is added in step (b), more preferably the alcohol is a $C_1$-$C_6$ alcohol, still more preferably the alcohol is methanol, ethanol, n-propanol or isopropanol, even more preferably the alcohol is methanol or ethanol. It is further preferred that the ratio of ethanol to water in step (b) is at least about 50% ethanol, e.g. about 55:45 ethanol:water, e.g. about 60:40 ethanol:water.

Alternatively, it is preferred that the ratio of ethanol to water in step (b) is less than about 50% ethanol, e.g. about 45:55 ethanol:water, e.g. about 40:60 ethanol:water.

In another aspect, the invention provides a process for preparing a compound of formula (V)

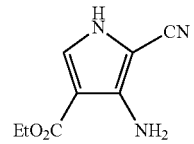

(V)

including the steps:

(d) reacting a compound of formula (III) with methyl chloroformate to produce a compound of formula (IV)

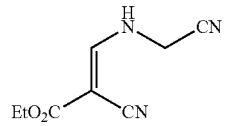

(III)

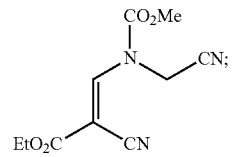

(IV)

and (e) cyclisation of the compound of formula (IV) under basic conditions to give the compound of formula (V);

wherein ethyl acetate is employed as a solvent in step (d).

Preferably DBU is employed as a base in the cyclisation step (e). More preferably DBU and dichloromethane are employed as base and solvent, respectively, in the cyclisation step (e). It is further preferred that a reaction time of less than about 15 minutes, e.g. about 10 minutes, is employed in step (e). It is also preferred that, after the reaction time of less than about 15 minutes in step (e), methanol, followed by ammonium acetate, are added to the reaction.

In still another aspect, the invention provides a process for preparing a compound of formula (XII)

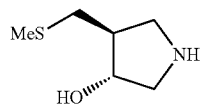

(XII)

including the steps:

(f) contacting a compound of formula (IX) with methanesulfonyl chloride and 2,6-lutidine followed by sodium thiomethoxide to give a compound of formula (X)

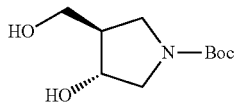

(IX)

-continued

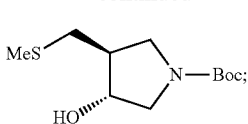
(X)

(g) deprotection of the compound of formula (X) followed by conversion to a compound of formula (XI)

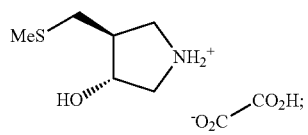
(XI)

and (h) conversion of the compound of formula (XI) to the compound of formula (XII); wherein acetone is employed as a solvent in step (f).

Preferably the deprotection of the compound of formula (X) in step (g) is carried out by contacting the compound of formula (X) with trifluoroacetic acid. It is further preferred that the conversion to compound (XI) in step (g) is carried out by contacting the deprotected compound of formula (X) with a resin such as a food grade strong base anionic exchange resin. It is also preferred that the conversion of the compound of formula (XI) to the compound (XII) in step (h) is carried out by contacting the compound of formula (XI) with a resin such as a food grade strong base anionic exchange resin.

In still another aspect, the invention provides a process for preparing (3R,4S)-1-((4-amino-5H-pyrrolo[3,2-d]pyrimidin-7-yl)methyl)-4-(methylthiomethyl)pyrrolidin-3-ol phosphate, including the steps:

(a) contacting a compound of formula (XII) with 9-deazaadenine and formaldehyde in water/ethanol solvent to produce (3R,4S)-1-((4-amino-5H-pyrrolo[3,2-d]pyrimidin-7-yl)methyl)-4-(methylthiomethyl)pyrrolidin-3-ol

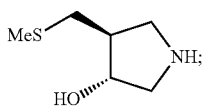
(XII)

(b) contacting the (3R,4S)-1-((4-amino-5H-pyrrolo[3,2-d]pyrimidin-7-yl)methyl)-4-(methylthiomethyl)pyrrolidin-3-ol produced in step (a) with:

(i) a solution of phosphoric acid in water, to produce a solution containing (3R,4S)-1-((4-amino-5H-pyrrolo[3,2-d]pyrimidin-7-yl)methyl)-4-(methylthiomethyl)pyrrolidin-3-ol phosphate;

(ii) seed crystals of (3R,4S)-1-((4-amino-5H-pyrrolo[3,2-d]pyrimidin-7-yl)methyl)-4-(methylthiomethyl)pyrrolidin-3-ol phosphate; and optionally (iii) ethanol;

to produce crystalline (3R,4S)-1-((4-amino-5H-pyrrolo[3,2-d]pyrimidin-7-yl)methyl)-4-(methylthiomethyl)pyrrolidin-3-ol phosphate;

(c) isolating crystalline (3R,4S)-1-((4-amino-5H-pyrrolo[3,2-d]pyrimidin-7-yl)methyl)-4-(methylthiomethyl)pyrrolidin-3-ol phosphate.

Preferably the ratio of water to ethanol in step (a) is about 4:1. It is further preferred that the reaction mixture in step (a) is stirred at ambient temperature for about 2 days.

Preferably the ethanol is added stepwise, in portions, in step (b). It is further preferred that the ethanol is added over a time period of about two hours.

DETAILED DESCRIPTION

Salt forms of (3R,4S)-1-((4-amino-5H-pyrrolo[3,2-d]pyrimidin-7-yl)methyl)-4-(methylthiomethyl)pyrrolidin-3-ol, particularly as exemplified, e.g. (3R,4S)-1-((4-amino-5H-pyrrolo[3,2-d]pyrimidin-7-yl)methyl)-4-(methylthiomethyl)pyrrolidin-3-ol phosphate, compound (Ia):

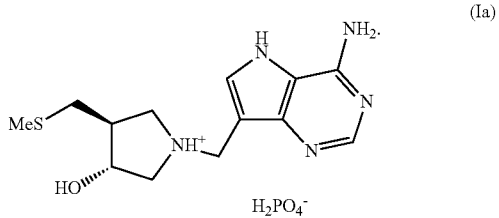
(Ia)

or (3R,4S)-1-((4-amino-5H-pyrrolo[3,2-d]pyrimidin-7-yl)methyl)-4-(methylthiomethyl)pyrrolidin-3-ol formate or (3R,4S)-1-((4-amino-5H-pyrrolo[3,2-d]pyrimidin-7-yl)methyl)-4-(methylthiomethyl)pyrrolidin-3-ol oxalate or (3R,4S)-1-((4-amino-5H-pyrrolo[3,2-d]pyrimidin-7-yl)methyl)-4-(methylthiomethyl)pyrrolidin-3-ol sulfate, are useful as a pharmaceuticals, for example for the treatment of diseases or disorders where it is desirable to inhibit MTAP, such as cancers, e.g. head and neck cancers, lung cancer, breast cancer, colon cancer, cervical cancer or prostate cancer.

For example, FIG. 8 shows a study of the effect of (3R,4S)-1-((4-amino-5H-pyrrolo[3,2-d]pyrimidin-7-yl)methyl)-4-(methylthiomethyl)pyrrolidin-3-ol phosphate on larger tumours (150 mm$^3$). The study uses MDA-MB-468 tumours grown orthotopically for 35 days in a mouse xenograft model. Treatment causes the 150 mm$^3$ tumours to shrink by half within days and suppresses growth for the subsequent 30 days. Doses of (3R,4S)-1-((4-amino-5H-pyrrolo[3,2-d]pyrimidin-7-yl)methyl)-4-(methylthiomethyl)pyrrolidin-3-ol phosphate from 24 to 30.5 mg/kg are equally effective at stopping cancer growth. Upon drug release, tumour size increases slowly relative to untreated tumours. Control tumours grow from 150 to 400 mm$^3$ over 35 days. At day 71, the large tumours are treated with 30 mg/kg i.p. (3R,4S)-1-((4-amino-5H-pyrrolo[3,2-d]pyrimidin-7-yl)methyl)-4-(methylthiomethyl)pyrrolidin-3-ol phosphate. The tumours undergo rapid decrease in size as a consequence of tumour lysis with most of the tumours resolved over a two-week period.

Those skilled in the art will appreciate that salt forms of (3R,4S)-1-((4-amino-5H-pyrrolo[3,2-d]pyrimidin-7-yl)methyl)-4-(methylthiomethyl)pyrrolidin-3-ol, such as (3R,4S)-1-((4-amino-5H-pyrrolo[3,2-d]pyrimidin-7-yl)methyl)-4-(methylthiomethyl)pyrrolidin-3-ol phosphate or (3R,4S)-1-((4-amino-5H-pyrrolo[3,2-d]pyrimidin-7-yl)methyl)-4-(methylthiomethyl)pyrrolidin-3-ol formate or (3R,4S)-1-((4-amino-5H-pyrrolo[3,2-d]pyrimidin-7-yl)methyl)-4-(methylthiomethyl)pyrrolidin-3-ol sulfate, can exist as solvates. For example, crystalline forms of (3R,4S)-1-((4-amino-5H-pyrrolo[3,2-d]pyrimidin-7-yl)methyl)-4-(methylthiomethyl)pyrrolidin-3-ol phosphate and (3R,4S)-1-(4-amino-5H-pyrrolo[3,2-d]pyrimidin-7-yl)methyl)-4-(methylthiomethyl)pyrrolidin-3-ol sulfate can contain waters of crystallisation.

Advantageously, the phosphate salt of (3R,4S)-1-((4-amino-5H-pyrrolo[3,2-d]pyrimidin-7-yl)methyl)-4-(methylthiomethyl)pyrrolidin-3-ol of the present invention provides improved stability and solubility. The phosphate salt of (3R,4S)-1-((4-amino-5H-pyrrolo[3,2-d]pyrimidin-7-yl)methyl)-4-(methylthiomethyl)pyrrolidin-3-ol can be crystallised directly from the reaction mixture providing the product in high purity. This is not achievable with the free base form or the hydrochloride salt form. The phosphate salt of (3R,4S)-1-((4-amino-5H-pyrrolo[3,2-d]pyrimidin-7-yl)methyl)-4-(methylthiomethyl)pyrrolidin-3-ol is suitable for large scale production, particularly because it can be purified by recrystallisation, whereas previously the only method to purify (3R,4S)-1-((4-amino-5H-pyrrolo[3,2-d]pyrimidin-7-yl)methyl)-4-(methylthiomethyl)pyrrolidin-3-ol was by chromatography.

The present invention provides:

1. A salt form of (3R,4S)-1-((4-amino-5H-pyrrolo[3,2-d]pyrimidin-7-yl)methyl)-4-(methylthiomethyl)pyrrolidin-3-ol, selected from the group consisting of (3R,4S)-1-((4-amino-5H-pyrrolo[3,2-d]pyrimidin-7-yl)methyl)-4-(methylthiomethyl)pyrrolidin-3-ol phosphate, (3R,4S)-1-((4-amino-5H-pyrrolo[3,2-d]pyrimidin-7-yl)methyl)-4-(methylthiomethyl)pyrrolidin-3-ol formate, (3R,4S)-1-((4-amino-5H-pyrrolo[3,2-d]pyrimidin-7-yl)methyl)-4-(methylthiomethyl)pyrrolidin-3-ol oxalate and (3R,4S)-1-((4-amino-5H-pyrrolo[3,2-d]pyrimidin-7-yl)methyl)-4-(methylthiomethyl)pyrrolidin-3-ol sulfate.

2. A salt form of (3R,4S)-1-((4-amino-5H-pyrrolo[3,2-d]pyrimidin-7-yl)methyl)-4-(methylthiomethyl)pyrrolidin-3-ol as described in the above paragraph 1, which is crystalline.

3. A salt form as described in the above paragraph 1 or the above paragraph 2 which is (3R,4S)-1-((4-amino-5H-pyrrolo[3,2-d]pyrimidin-7-yl)methyl)-4-(methylthiomethyl)pyrrolidin-3-ol phosphate, a compound of formula (Ia):

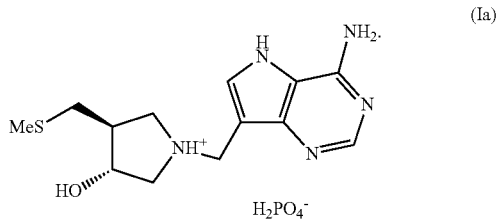

(Ia)

4. A salt form as described in the above paragraph 1 or the above paragraph 2 which is crystalline (3R,4S)-1-((4-amino-5H-pyrrolo[3,2-d]pyrimidin-7-yl)methyl)-4-(methylthiomethyl)pyrrolidin-3-ol phosphate of Form D characterised by X-ray power diffraction peaks at the following 2 theta angles: about 5.38, 7.10, 8.93, 10.87, 13.06, 14.31, 15.81, 17.59, 17.92, 19.97, 21.53, 22.76, 26.00, 27.06, 27.79, 28.95 and 29.97 degrees 2 theta±0.05 degrees 2 theta, which correspond, respectively, to the following d-spacings: about 19.1, 14.4, 11.49, 9.44, 7.87, 7.18, 6.50, 5.85, 5.74, 5.16, 4.79, 4.53, 3.977, 3.823, 3.725, 3.579 and 3.459 Å.

5. A salt form as described in the above paragraph 4 which is further characterised by one or more additional X-ray power diffraction peaks at the following 2 theta angles: about 14.57, 15.32, 16.50, 19.07, 20.17, 20.77, 21.78, 22.22, 23.12, 24.84, 25.75, 26.31, 28.14, 28.57, 29.35, 30.50, 30.91, 31.35, 32.64, 32.09, 34.17, 33.33 degrees 2 theta±0.05 degrees 2 theta, which correspond, respectively, to the following d-spacings: about 7.05, 6.71, 6.23, 5.40, 5.11, 4.96, 4.73, 4.64, 4.46, 4.159, 4.014, 3.931, 3.679, 3.625, 3.531, 3.401, 3.357, 3.311, 3.183, 3.236, 3.045, 3.119 Å.

6. A salt form as described in the above paragraph 1 or the above paragraph 2 which is crystalline (3R,4S)-1-((4-amino-5H-pyrrolo[3,2-d]pyrimidin-7-yl)methyl)-4-(methylthiomethyl)pyrrolidin-3-ol phosphate Form D having an X-ray power diffraction pattern substantially as shown in FIG. 3(a).

7. A salt form as described in the above paragraph 1 or the above paragraph 2 which is crystalline (3R,4S)-1-((4-amino-5H-pyrrolo[3,2-d]pyrimidin-7-yl)methyl)-4-(methylthiomethyl)pyrrolidin-3-ol phosphate of Form E characterised by X-ray power diffraction peaks at the following 2 theta angles: about 5.26, 7.01, 8.69, 10.58, 15.95, 17.26, 17.57, 21.27, 21.60, 22.75, 25.64, 26.88, 28.86, 29.99 and 30.75 degrees 2 theta±0.05 degrees 2 theta, which correspond, respectively, to the following d-spacings: about 19.5, 14.6, 11.81, 9.70, 6.45, 5.96, 5.86, 4.85, 4.77, 4.54, 4.031, 3.849, 3.589, 3.457 and 3.374 Å.

8. A salt form as described in the above paragraph 7 which is further characterised by one or more additional X-ray power diffraction peaks at the following 2 theta angles: about 8.91, 12.56, 16.76, 17.84, 19.36, 20.14, 20.86, 22.09, 22.53, 23.03, 24.14, 25.95, 26.16, 26.63, 27.72, 29.35, 30.22, 31.11, 31.57, 32.38, 33.04, 33.38, 33.93 degrees 2 theta±0.05 degrees 2 theta, which correspond, respectively, to the following d-spacings: about 11.52, 8.18, 6.14, 5.77, 5.32, 5.12, 4.94, 4.67, 4.58, 4.48, 4.278, 3.984, 3.952, 3.884, 3.734, 3.531, 3.431, 3.336, 3.288, 3.208, 3.146, 3.115, 3.066 Å.

9. A salt form as described in the above paragraph 1 or the above paragraph 2 which is crystalline (3R,4S)-1-((4-amino-5H-pyrrolo[3,2-d]pyrimidin-7-yl)methyl)-4-(methylthiomethyl)pyrrolidin-3-ol phosphate Form E having an X-ray power diffraction pattern substantially as shown in FIG. 4(a).

10. A salt form as described in the above paragraph 1 or the above paragraph 2 which is crystalline (3R,4S)-1-((4-amino-5H-pyrrolo[3,2-d]pyrimidin-7-yl)methyl)-4-(methylthiomethyl)pyrrolidin-3-ol phosphate of Form F characterised by X-ray power diffraction peaks at the following 2 theta angles: about 5.25, 7.00, 8.73, 10.67, 15.82, 16.04, 17.52, 17.75, 20.13, 20.77, 21.36, 21.72, 22.79, 25.70, 26.10, 28.55, 29.56, 30.52, 31.43 and 32.42 degrees 2 theta±0.05 degrees 2 theta, which correspond, respectively, to the following d-spacings: about 19.5, 14.7, 11.76, 9.62, 6.50, 6.41, 5.87, 5.80, 5.12, 4.97, 4.83, 4.75, 4.53, 4.022, 3.962, 3.627, 3.506, 3.398, 3.303 and 3.204 Å.

11. A salt form as described in the above paragraph 10 which is further characterised by one or more additional X-ray power diffraction peaks at the following 2 theta angles: about 8.92, 12.69, 14.19, 15.14, 16.68, 19.21, 22.09, 23.60, 24.35, 24.80, 26.81, 27.00, 27.81, 29.01, 29.88, 32.12, 32.95, 33.68, 34.08, 35.08, 35.84, 36.58, 37.32, 39.18, 40.37, 40.79, 41.84, 42.56, 43.62, 44.51, 46.14, 46.52, 47.00, 48.24, 49.02, 49.54 degrees 2 theta±0.05 degrees 2 theta, which correspond, respectively, to the following d-spacings: about 11.50, 8.09, 7.25, 6.79, 6.17, 5.36, 4.67, 4.374, 4.241, 4.165, 3.859, 3.832, 3.722, 3.571, 3.469, 3.233, 3.154, 3.088, 3.052, 2.968, 2.907, 2.850, 2.795, 2.668, 2.592, 2.567, 2.505, 2.464, 2.408, 2.362, 2.283, 2.265, 2.243, 2.189, 2.156, 2.135 Å.

12. A salt form as described in the above paragraph 1 or the above paragraph 2 which is crystalline (3R,4S)-1-((4-amino-5H-pyrrolo[3,2-d]pyrimidin-7-yl)methyl)-4-(methylthiomethyl)pyrrolidin-3-ol phosphate Form F having an X-ray power diffraction pattern substantially as shown in FIG. 5(a).

13. A salt form as described in the above paragraph 1 or the above paragraph 2 which is crystalline (3R,4S)-1-((4-amino-5H-pyrrolo[3,2-d]pyrimidin-7-yl)methyl)-4-(methylthiomethyl)pyrrolidin-3-ol oxalate characterised by X-ray power diffraction peaks at the following 2 theta angles: about 6.22, 12.35, 13.54, 18.23, 20.47, 21.94, 24.22 and 29.44 degrees 2 theta±0.05 degrees 2 theta, which correspond, respectively, to the following d-spacings: about 16.5, 8.32, 7.59, 5.65, 5.03, 4.70, 4.263 and 3.520 Å.

14. A salt form as described in the above paragraph 13 which is further characterised by one or more additional X-ray power diffraction peaks at the following 2 theta angles: about 14.94, 15.72, 19.11, 22.54, 30.07, 31.11, 32.06, 32.71, 33.90 degrees 2 theta±0.05 degrees 2 theta, which correspond, respectively, to the following d-spacings: about 6.88, 6.54, 5.39, 4.58, 3.448, 3.336, 3.239, 3.177, 3.068 Å.

15. A salt form as described in the above paragraph 1 or the above paragraph 2 which is crystalline (3R,4S)-1-((4-amino-5H-pyrrolo[3,2-d]pyrimidin-7-yl)methyl)-4-(methylthiomethyl)pyrrolidin-3-ol oxalate having an X-ray power diffraction pattern substantially as shown in FIG. 1(a).

16. A salt form as described in the above paragraph 1 or the above paragraph 2 which is crystalline (3R,4S)-1-((4-amino-5H-pyrrolo[3,2-d]pyrimidin-7-yl)methyl)-4-(methylthiomethyl)pyrrolidin-3-ol formate characterised by X-ray power diffraction peaks at the following 2 theta angles: about 8.11, 16.30, 20.68, 24.85, 25.70, 26.03, 28.00, 32.23 and 33.02 degrees 2 theta±0.05 degrees 2 theta, which correspond, respectively, to the following d-spacings: about 12.65, 6.31, 4.98, 4.157, 4.022, 3.972, 3.698, 3.223 and 3.147 Å.

17. A salt form as described in the above paragraph 16 which is further characterised by one or more additional X-ray power diffraction peaks at the following 2 theta angles: about 10.34, 13.66, 17.54, 17.95, 18.83, 21.32, 21.71, 23.17, 24.63, 27.13, 27.57, 28.51, 28.77, 30.33, 31.05, 31.24, 33.45, 34.24, 34.52, 35.57, 35.99, 36.66, 36.93, 38.15, 38.91, 39.94, 40.47, 41.45, 42.17, 42.75, 44.36, 45.15, 46.27, 46.50, 47.36, 48.49, 49.20, 50.12 degrees 2 theta±0.05 degrees 2 theta, which correspond, respectively, to the following d-spacings: about 9.93, 7.52, 5.87, 5.74, 5.47, 4.84, 4.75, 4.45, 4.194, 3.814, 3.754, 3.632, 3.600, 3.420, 3.342, 3.322, 3.108, 3.039, 3.014, 2.929, 2.896, 2.845, 2.825, 2.737, 2.686, 2.619, 2.586, 2.528, 2.486, 2.454, 2.369, 2.330, 2.277, 2.266, 2.227, 2.178, 2.149, 2.112 Å.

18. A salt form as described in the above paragraph 1 or the above paragraph 2 which is crystalline (3R,4S)-1-((4-amino-5H-pyrrolo[3,2-d]pyrimidin-7-yl)methyl)-4-(methylthiomethyl)pyrrolidin-3-ol formate having an X-ray power diffraction pattern substantially as shown in FIG. 6(a).

19. A salt form as described in the above paragraph 1 or the above paragraph 2 which is crystalline (3R,4S)-1-((4-amino-5H-pyrrolo[3,2-d]pyrimidin-7-yl)methyl)-4-(methylthiomethyl)pyrrolidin-3-ol sulfate characterised by X-ray power diffraction peaks at the following 2 theta angles: about 5.75, 10.33, 13.14, 15.41, 15.90, 17.61, 18.32, 21.43, 24.30, 26.15, 26.76, 27.67, 30.28, 30.97, 31.52 and 32.27 degrees 2 theta±0.05 degrees 2 theta, which correspond, respectively, to the following d-spacings: about 17.8, 9.94, 7.82, 6.67, 6.47, 5.84, 5.62, 4.81, 4.25, 3.954, 3.866, 3.741, 3.425, 3.35, 3.293 and 3.219 Å.

20. A salt form as described in the above paragraph 19 which is further characterised by one or more additional X-ray power diffraction peaks at the following 2 theta angles: about 19.14, 20.28, 20.87, 22.26, 24.64, 29.37, 33.24 degrees 2 theta±0.05 degrees 2 theta, which correspond, respectively, to the following d-spacings: about 5.38, 5.08, 4.94, 4.63, 4.192, 3.529, 3.127 Å.

21. A salt form as described in the above paragraph 1 or the above paragraph 2 which is crystalline (3R,4S)-1-((4-amino-5H-pyrrolo[3,2-d]pyrimidin-7-yl)methyl)-4-(methylthiomethyl)pyrrolidin-3-ol sulfate having an X-ray power diffraction pattern substantially as shown in FIG. 2(a).

22. A salt form as described in the above paragraph 1 or the above paragraph 2 which is (3R,4S)-1-((4-amino-5H-pyrrolo[3,2-d]pyrimidin-7-yl)methyl)-4-(methylthiomethyl)pyrrolidin-3-ol phosphate which exhibits an endotherm at a range of about 165° C. to about 185° C. as measured by differential scanning calorimetry.

23. A salt form as described in the above paragraph 1 or the above paragraph 2 which is (3R,4S)-1-((4-amino-5H-pyrrolo[3,2-d]pyrimidin-7-yl)methyl)-4-(methylthiomethyl)pyrrolidin-3-ol phosphate of Form D, having a differential scanning calorimetry thermogram substantially as shown in FIG. 3(c).

24. A salt form as described in the above paragraph 1 or the above paragraph 2 which is (3R,4S)-1-((4-amino-5H-pyrrolo[3,2-d]pyrimidin-7-yl)methyl)-4-(methylthiomethyl)pyrrolidin-3-ol phosphate of Form E, having a differential scanning calorimetry thermogram substantially as shown in FIG. 4(c).

25. A salt form as described in the above paragraph 1 or the above paragraph 2 which is (3R,4S)-1-((4-amino-5H-pyrrolo[3,2-d]pyrimidin-7-yl)methyl)-4-(methylthiomethyl)pyrrolidin-3-ol phosphate of Form F, having a differential scanning calorimetry thermogram substantially as shown in FIG. 5(c).

26. A salt form as described in the above paragraph 1 or the above paragraph 2 which is (3R,4S)-1-((4-amino-5H-pyrrolo[3,2-d]pyrimidin-7-yl)methyl)-4-(methylthiomethyl)pyrrolidin-3-ol oxalate which exhibits an endotherm at about 137.04° C. as measured by differential scanning calorimetry.

27. A salt form as described in the above paragraph 1 or the above paragraph 2 which is (3R,4S)-1-((4-amino-5H-pyrrolo[3,2-d]pyrimidin-7-yl)methyl)-4-(methylthiomethyl)pyrrolidin-3-ol oxalate, having a differential scanning calorimetry thermogram substantially as shown in FIG. 1(b).

28. A salt form as described in the above paragraph 1 or the above paragraph 2 which is (3R,4S)-1-((4-amino-5H-pyrrolo[3,2-d]pyrimidin-7-yl)methyl)-4-(methylthiomethyl)pyrrolidin-3-ol formate which exhibits an endotherm at about 179.54° C. as measured by differential scanning calorimetry.

29. A salt form as described in the above paragraph 1 or the above paragraph 2 which is (3R,4S)-1-((4-amino-5H-pyrrolo[3,2-d]pyrimidin-7-yl)methyl)-4-(methylthiomethyl)pyrrolidin-3-ol formate, having a differential scanning calorimetry thermogram substantially as shown in FIG. 6(c).

30. A pharmaceutical composition comprising a salt form as described in any one of the above paragraphs 1 to 29 and at least one pharmaceutically acceptable excipient.

31. A pharmaceutical composition as described in the above paragraph 30, wherein the salt form is (3R,4S)-1-((4-amino-5H-pyrrolo[3,2-d]pyrimidin-7-yl)methyl)-4-(methylthiomethyl)pyrrolidin-3-ol phosphate.

32. A method of treating a disease or disorder in which it is desirable to inhibit MTAP, comprising administering an effective amount of a salt form as described in any one of the above paragraphs 1 to 29 to a patient in need thereof.

33. A method as described in the above paragraph 32, wherein the salt form is (3R,4S)-1-((4-amino-5H-pyrrolo[3,2-d]pyrimidin-7-yl)methyl)-4-(methylthiomethyl)pyrrolidin-3-ol phosphate.

34. A method as described in the above paragraph 32 or 33, wherein the disease or disorder is cancer.

35. A process for the preparation of crystalline (3R,4S)-1-((4-amino-5H-pyrrolo[3,2-d]pyrimidin-7-yl)methyl)-4-(methylthiomethyl)pyrrolidin-3-ol phosphate, including the steps:
(a) preparing a solution of (3R,4S)-1-((4-amino-5H-pyrrolo[3,2-d]pyrimidin-7-yl)methyl)-4-(methylthiomethyl)pyrrolidin-3-ol phosphate in water;
(b) adding an alcohol, methyl ethyl ketone, tetrahydrofuran or acetone to the solution, to form crystals of (3R,4S)-1-((4-amino-5H-pyrrolo[3,2-d]pyrimidin-7-yl)methyl)-4-(methylthiomethyl)pyrrolidin-3-ol phosphate; and
(c) isolating the crystals of (3R,4S)-1-((4-amino-5H-pyrrolo[3,2-d]pyrimidin-7-yl)methyl)-4-(methylthiomethyl)pyrrolidin-3-ol phosphate.

36. A process as described in the above paragraph 35 wherein ethanol is added in step (b).

37. A process for preparing a compound of formula (V)

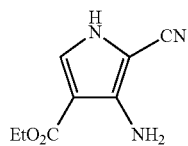

(V)

including the steps:
(d) reacting a compound of formula (III) with methyl chloroformate to produce a compound of formula (IV)

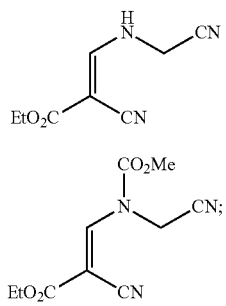

(III)

(IV)

and
(e) cyclisation of the compound of formula (IV) under basic conditions to give the compound of formula (V);
wherein ethyl acetate is employed as a solvent in step (d).

38. A process for preparing a compound of formula (XII)

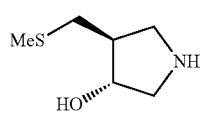

(XII)

including the steps:
(f) contacting a compound of formula (IX) with methanesulfonyl chloride and 2,6-lutidine followed by sodium thiomethoxide to give a compound of formula (X)

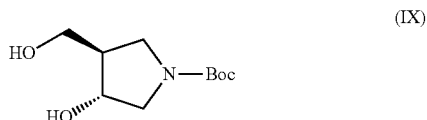

(IX)

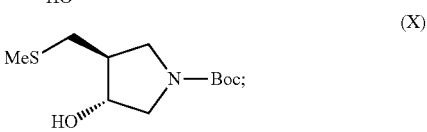

(X)

(g) deprotection of the compound of formula (X) followed by conversion to a compound of formula (XI)

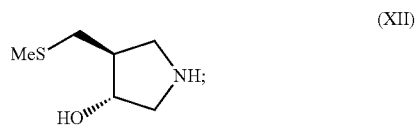

(XII)

and
(h) conversion of the compound of formula (XI) to the compound of formula (XII); wherein acetone is employed as a solvent in step (f).

39. A process for preparing (3R,4S)-1-((4-amino-5H-pyrrolo[3,2-d]pyrimidin-7-yl)methyl)-4-(methylthiomethyl)pyrrolidin-3-ol phosphate, including the steps:
(a) contacting a compound of formula (XII) with 9-deazaadenine and formaldehyde in water/ethanol solvent to produce (3R,4S)-1-((4-amino-5H-pyrrolo[3,2-d]pyrimidin-7-yl)methyl)-4-(methylthiomethyl)pyrrolidin-3-ol (XII)

(b) contacting the (3R,4S)-1-((4-amino-5H-pyrrolo[3,2-d]pyrimidin-7-yl)methyl)-4-(methylthiomethyl)pyrrolidin-3-ol produced in step (a) with:
(i) a solution of phosphoric acid in water, to produce a solution containing (3R,4S)-1-((4-amino-5H-pyrrolo[3,2-d]pyrimidin-7-yl)methyl)-4-(methylthiomethyl)pyrrolidin-3-ol phosphate;
(ii) seed crystals of (3R,4S)-1-((4-amino-5H-pyrrolo[3,2-d]pyrimidin-7-yl)methyl)-4-(methylthiomethyl)pyrrolidin-3-ol phosphate; and optionally
(iii) ethanol;
to produce crystalline (3R,4S)-1-((4-amino-5H-pyrrolo[3,2-d]pyrimidin-7-yl)methyl)-4-(methylthiomethyl)pyrrolidin-3-ol phosphate;
(c) isolating crystalline (3R,4S)-1-((4-amino-5H-pyrrolo[3,2-d]pyrimidin-7-yl)methyl)-4-(methylthiomethyl)pyrrolidin-3-ol phosphate.

Definitions

The term "patient" includes human and non-human animals.

The terms "treatment", "treating" and the like include the alleviation of one or more symptoms, or improvement of a state associated with the disease or disorder, for example in the case of cancer, a reduction in tumour size or suppression of tumour growth.

Synthesis of Compound (I)

(3R,4S)-1-((4-Amino-5H-pyrrolo[3,2-d]pyrimidin-7-yl) methyl)-4-(methylthiomethyl)pyrrolidin-3-ol, compound (I), and its phosphate salt, (3R,4S)-1-((4-amino-5H-pyrrolo [3,2-d]pyrimidin-7-yl)methyl)-4-(methylthiomethyl)pyrrolidin-3-ol phosphate, compound (Ia), are synthesised by the convergence of two reaction pathways.

The first pathway is a five step process to afford the 9-deazaadenine (VII) as shown in Scheme 1.

The synthesis of compound (VI) involves isolation of the product and subsequent re-charging of the reaction. In this way, it is surprisingly possible to obtain approximately full conversion.

Saponification of compound (VI) followed by decarboxylation removes the ester group. As the reaction nears completion it is common to observe crystallisation of the product which results in high purity of approximately 99.74%, indicating that purification occurs on crystallisation which is advantageous for scale-up procedures.

The second pathway is a four step process to afford the pyrrolidine (XII) as shown in Scheme 2.

Scheme 1: Synthesis of 9-deazaadenine (VII)

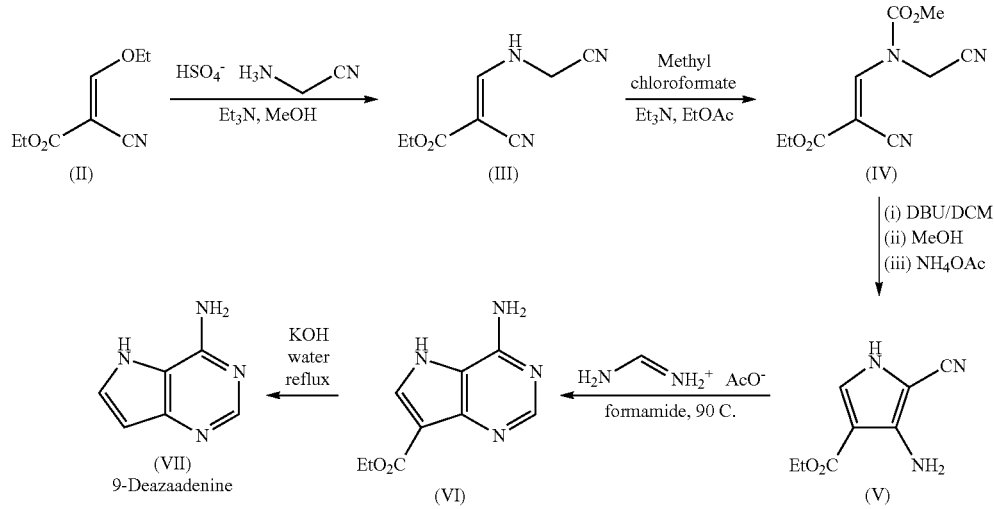

Compound (III) is formed from an olefin addition-elimination reaction of compound (II) with aminoacetonitrile bisulfate in the presence of triethylamine in methanol. The order of addition is carefully controlled to mange the associated exotherm (4.6° C. temperature rise over 5 minutes addition on 10 g scale). Compound (III) is further reacted with methyl chloroformate (MCF). Advantageously, the present process uses ethyl acetate in this step, minimising the use of toxic solvents. It is preferred that dry ethyl acetate is used. The formation of compound (IV) is complete in approximately 10 minutes.

The present inventors have found that variation of temperature and olefin concentration has a strong influence on yield, and that the cyclised product can be unstable. The present process employs a suitably short reaction time in order to minimise the degradation of the cyclised product (V). The free pyrrole, compound (V), is readily precipitated from a variety of solvents leading to a convenient and scale-friendly method for purification and improved yield and purity.

It is surprisingly found that precipitation of compound (V) from ethanol/water removes many of the impurities formed during cyclisation and any residual colour from the reaction. However two impurities remain and their removal at a later stage is required. Increasing the scale of the reaction gives consistent results with compound (V) isolated in 72% yield and 82.8% purity. Thus, advantageously, compound (V) is produced in solid form in high purity.

Scheme 2: Synthesis of Pyrolidine (XII)

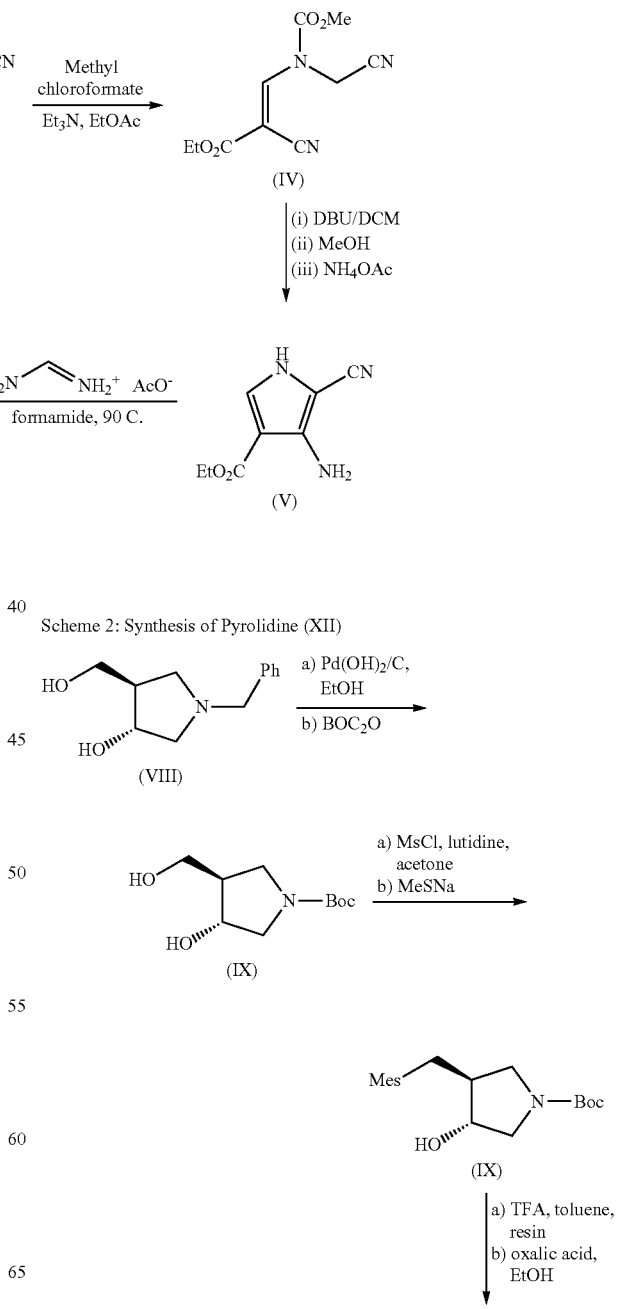

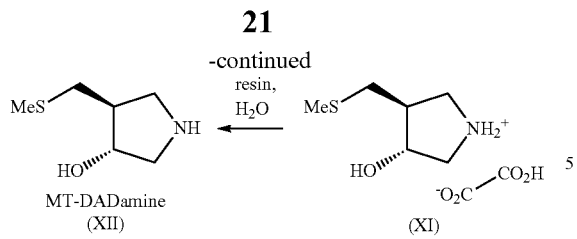

MT-DADamine (XII) ← resin, H₂O — (XI)

Removal of the benzyl protecting group from (VIII) is achieved by hydrogenolysis using Pearlman's catalyst (10 wt % charge relative to (VIII)) under balloon pressure of hydrogen in ethanol. If hydrogenolysis stalls, a second charge of catalyst can be used to achieve conversion. The catalyst is removed via filtration and the resulting solution treated with di-t-butyl dicarbonate. Once gas evolution has stopped the mixture is evaporated to give a quantitative yield of compound (IX) which is used without any further purification.

It has previously been found that mesylation of compound (IX) at the 6-position can be difficult due to participation of the nitrogen in the reaction (Tet. Asymm., 9, 1998, 1051-1057). Only moderate protecting group selectivity is observed resulting in mixtures of the 3-mesyl, 6-mesyl and bis-mesyl protected compounds. This can result in poor yield of the desired product compound (X). However, the present inventors have found that reaction of compound (IX) with methanesulfonyl chloride in an acetone/lutidine system followed by thiomethoxide displacement gives compound (X) in good yield and purity after chromatography.

Deprotection of compound (X) is traditionally accomplished using an aqueous HCl/methanol mixture followed by evaporation to dryness. The present process involves a scale-friendly approach using trifluoroacetic acid and food-grade strong base ion-exchange resins such as Amberlite FPA91 and FPA98 in isopropyl alcohol.

For complete basification, it is important to allow sufficient contact time of the substrate with the resin. This is achieved through slurrying the compound in an IPA solution with the resin for twenty minutes, followed by loading of the slurry on to a column containing more resin and eluting under gravity. Approximately 10 times the weight of resin relative to compound (X) is required for complete deprotection. The use of ion-exchange resin provides a reliable method for generation of crude (XII) in free base form.

Scheme 3: Convergence of Synthetic Routes to form Compound (Ia)

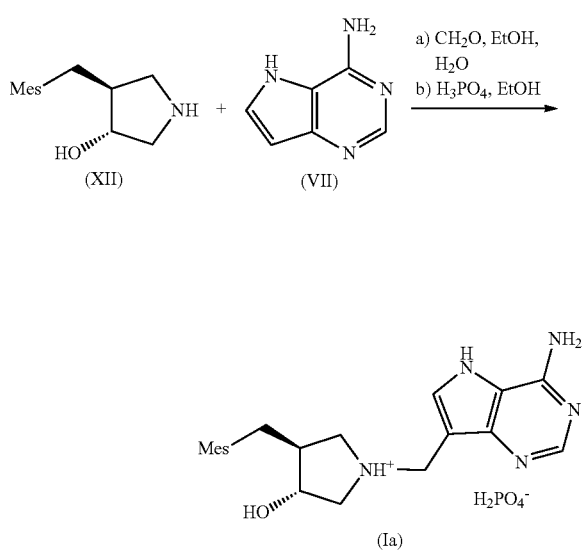

The final stage in the preparation of compound (Ia) is shown in Scheme 3. Oxalate salt, compound (XI), is first converted to the free base (XII) using Amberlite FPA91 ion exchange resin in water to give (XII) before coupling with (VII) and formaldehyde in water/ethanol to give compound (Ia). Following coupling, phosphoric acid is charged along with ethanol as an antisolvent to crystallise compound (Ia) from solution. A water/ethanol ratio of about 45:55 to about 15:85, e.g. about 40:60 is selected to facilitate controlled crystallisation of (Ia) via gradual addition of ethanol as the antisolvent. Compound (Ia) can be recrystallised from water/ethanol or water/methanol.

A crystallisation screen of compound (I) with a number of counter-ions indicates that the oxalate, sulfate, formate and phosphate salts are crystalline. Microanalyses of the phosphate, formate and sulfate salts with interpreted stoichiometries are given below (Table 1).

TABLE 1

Microanalysis of salt forms of compound (I)

| Formula | Form | | C (%) | H (%) | N (%) | S (%) | P (%) |
|---|---|---|---|---|---|---|---|
| compound (I)•H₂SO₄•2(H₂O) | B | Calculated | 36.52 | 5.89 | 16.38 | — | — |
| | | Found | 36.63 | 6.04 | 16.29 | — | — |
| compound (I)•1.30(H₃PO₄)•0.86(H₂O) | D | Calculated | 35.81 | 5.62 | 16.06 | — | 9.23 |
| | | Found | 35.83 | 5.50 | 15.94 | — | 9.77 |
| compound (I)•1.43(H₃PO₄)•0.44(H₂O) | E | Calculated | 35.36 | 5.52 | 15.86 | — | 10.22 |
| | | Found | 35.35 | 5.52 | 15.87 | — | 10.00 |
| compound (I)•1.43(H₃PO₄)•0.44(H₂O) | F | Calculated | 35.36 | 5.52 | 15.86 | — | 10.22 |
| | | Found | 35.34 | 5.52 | 15.86 | — | 10.10 |
| compound (I)•HCO₂H | G | Calculated | 49.54 | 6.24 | 20.63 | 9.45 | — |
| | | Found | 49.42 | 6.42 | 20.75 | 9.56 | — |

Advantageously, a crystalline salt form is provided for handling on scale-up. Crystallisation of the oxalate salt from ethanol gives a filterable crystalline slurry of the pyrrolidine as the oxalate salt (XI) in 80% yield in high purity.

X-ray powder diffraction (XRPD), differential scanning calorimetry (DSC) and thermogravimetric analysis (TGA) indicate that compound (Ia), (3R,4S)-1-((4-amino-5H-pyrrolo[3,2-d]pyrimidin-7-yl)methyl)-4-(methylthiomethyl)

pyrrolidin-3-ol phosphate, exists as polymorphic forms. All forms show similarity in DSC analysis.

TABLE 2

Polymorphs of Compound (Ia)

| Crystal Form | Antisolvent |
|---|---|
| E | EtOH (64%) |
| D | EtOH (40%) |
| F | MeOH |

Compound I(a), (3R,4S)-1-((4-amino-5H-pyrrolo[3,2-d]pyrimidin-7-yl)methyl)-4-(methylthiomethyl)pyrrolidin-3-ol phosphate, exists as two polymorphic forms, D and E, isolated from ethanol, and one polymorphic form, F, isolated from methanol, as shown in Table 2 above.

Recrystallisation of crystal forms D and E can be utilised as a means of increasing purity by dissolution in water with warming to about 38° C., addition of ethanol and subsequent cooling to 30° C. Seed crystals are added followed by further cooling to 20° C. over 1 h. Ethanol is added slowly and the slurry aged for 1 h. A second portion of ethanol is added and the slurry aged for 1 h. A third portion of ethanol is added and the slurry aged for 1 h. The crystals are collected on filter paper and washed with ethanol and dried under vacuum (FIG. 9). The level of residual ethanol (by $^1$H NMR) is approximately 0.5 wt % and this corresponds to the ICH guidance for an oral active pharmaceutical ingredient.

Recrystallisation of crystal form F can also be utilised as a means of increasing purity by the same procedure described above, substituting ethanol with methanol.

Further Aspects

Salt forms of compound (I), e.g. compound (Ia), (3R,4S)-1-((4-amino-5H-pyrrolo[3,2-d]pyrimidin-7-yl)methyl)-4-(methylthiomethyl)pyrrolidin-3-ol phosphate, may be administered to a patient by a variety of routes; its route of administration is not limited. Such administration routes include oral, parenteral, topical, rectal, nasal, buccal, by inhalation spray, or via an implanted reservoir. The amount of compound to be administered will vary widely according to the nature of the patient and the nature and extent of the disorder to be treated. Typically the dosage for an adult human will be in the range less than 1 to 1000 milligrams, preferably 0.1 to 100 milligrams. The compounds can be administered using a variety of dosage regimes, for example once daily or twice daily doses. Those skilled in the art will appreciate that the dosage regimes will vary according to the nature of the patient and the nature and extent of the disorder to be treated.

Salt forms of compound (I), e.g. compound (Ia), can be provided as pharmaceutical compositions. Salt forms of compound (I), e.g. compound (Ia), may be formulated into solid or liquid preparations such as tablets, capsules, suppositories, powders, solutions, suspensions and dispersions. In some embodiments the salt forms of compound (I), e.g. compound (Ia), are formulated for oral administration as solid or liquid preparations, for example tablets, capsules, powders, solutions, suspensions or dispersions. Such preparations are well known in the art. In tablet form, the salt forms of compound (I), e.g. compound (Ia), may be tableted with conventional tablet bases such as glucose, lactose, sucrose, mannitol, and corn starch; together with a binder for example, corn starch or gelatin; a disintegration agent such as carboxymethyl cellulose, poly vinyl pyrrolidinone, potato starch, alginic acid, and gelatin; and a lubricant such as magnesium stearate or talc. For oral administration in the form of capsules, diluents such as lactose and dried corn-starch may be employed. Other components such as colourings, sweeteners or flavourings may be added.

When aqueous suspensions are required for oral use the salt forms of compound (I), e.g. compound (Ia), may be combined with carriers such as water and ethanol, and emulsifying agents, suspending agents and/or surfactants may be used. Colourings, sweeteners, flavourings or pH regulators may also be added.

Salt forms of compound (I), e.g. compound (Ia), may further be administered by means of sustained release systems. For example, they may be incorporated into a slowly dissolving tablet or capsule.

Liquid forms include carriers such as water and ethanol, with or without other agents such as pharmaceutically acceptable surfactants or suspending agents.

The salt forms of compound (I), e.g. compound (Ia), may also be administered by injection in a physiologically acceptable diluent such as water or saline. The diluent may comprise one or more other ingredients such as ethanol, propylene glycol, an oil or a pharmaceutically acceptable surfactant.

The salt forms of compound (I), e.g. compound (Ia), may be present as ingredients in creams, for topical administration to skin or mucous membranes. Preferably the creams include a pharmaceutically acceptable solvent to assist passage through the skin or mucous membranes. Suitable creams are well known to those skilled in the art.

ABBREVIATIONS

Figure 1A:
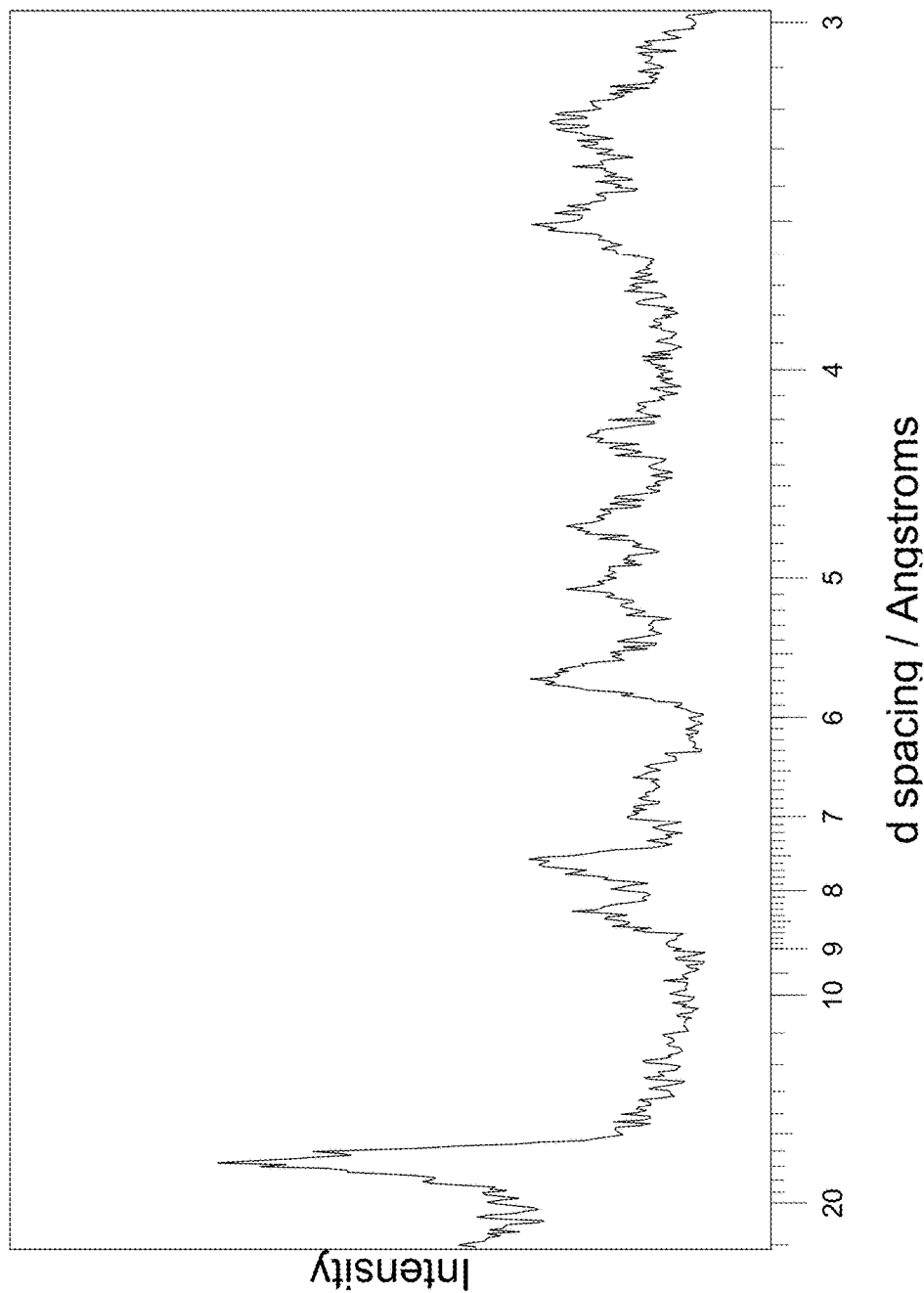
FIG. 1A-1B shows, for (3R,4S)-1-((4-amino-5H-pyrrolo[3,2-d]pyrimidin-7-yl)methyl)-4-(methylthiomethyl)pyrrolidin-3-ol oxalate: (A) X-ray powder diffraction (measured using a Bruker D8 Advance diffractometer); (B) DSC trace (measured using a Mettler-Toledo DSC1 Star-e system), melting endotherm onset at 137.04° C. (scanning from 25° C. to 300° C.; scan rate 10° C./min).
Figure 1B:
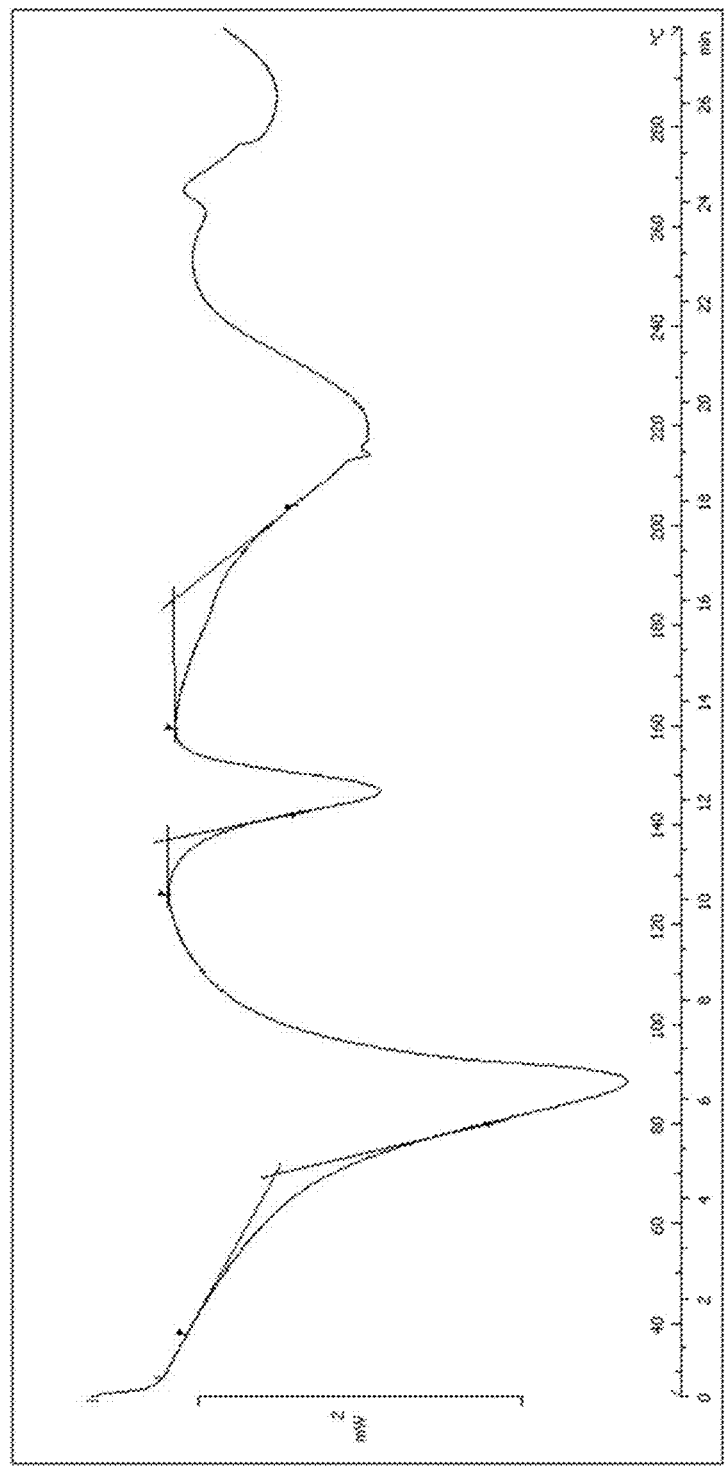
Figure 2A:
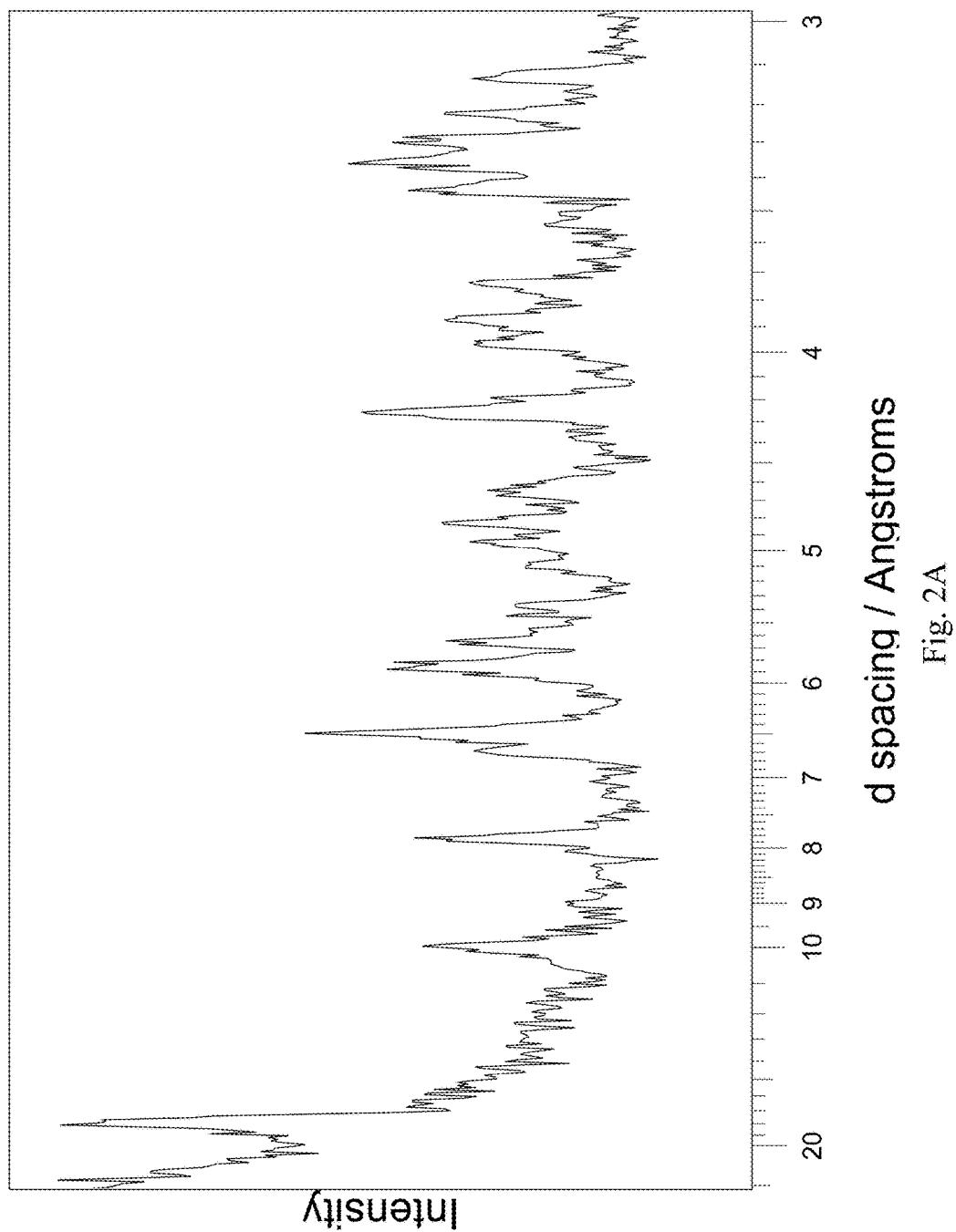
FIG. 2A-2B shows, for (3R,4S)-1-((4-amino-5H-pyrrolo[3,2-d]pyrimidin-7-yl)methyl)-4-(methylthiomethyl)pyrrolidin-3-ol sulfate: (A) X-ray powder diffraction (measured using a Bruker D8 Advance diffractometer); (B) DSC trace (measured using a Mettler-Toledo DSC1 Star-e system), no obvious melting transition (scanning from 25° C. to 300° C.; scan rate 10° C./min).
Figure 2B:
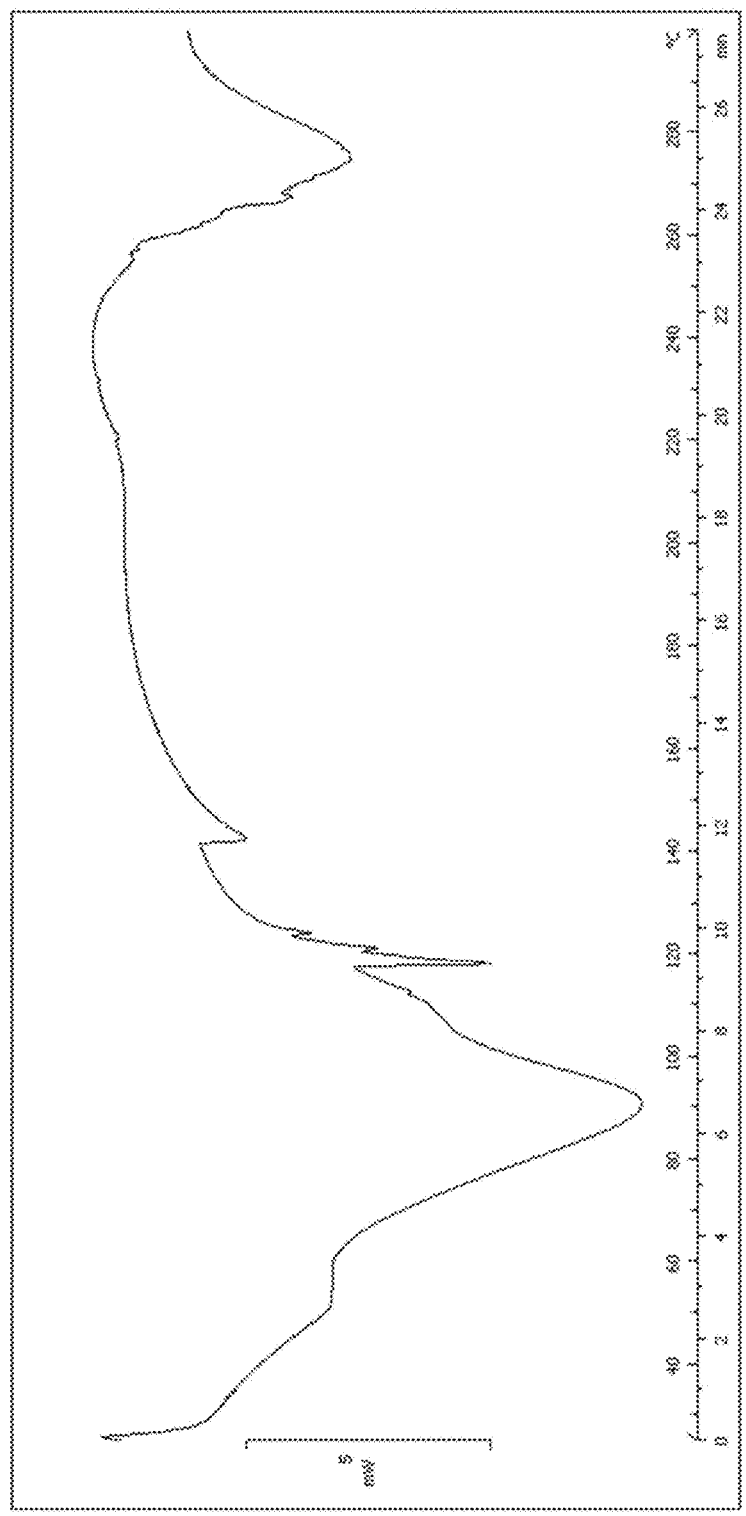
Figure 3A:
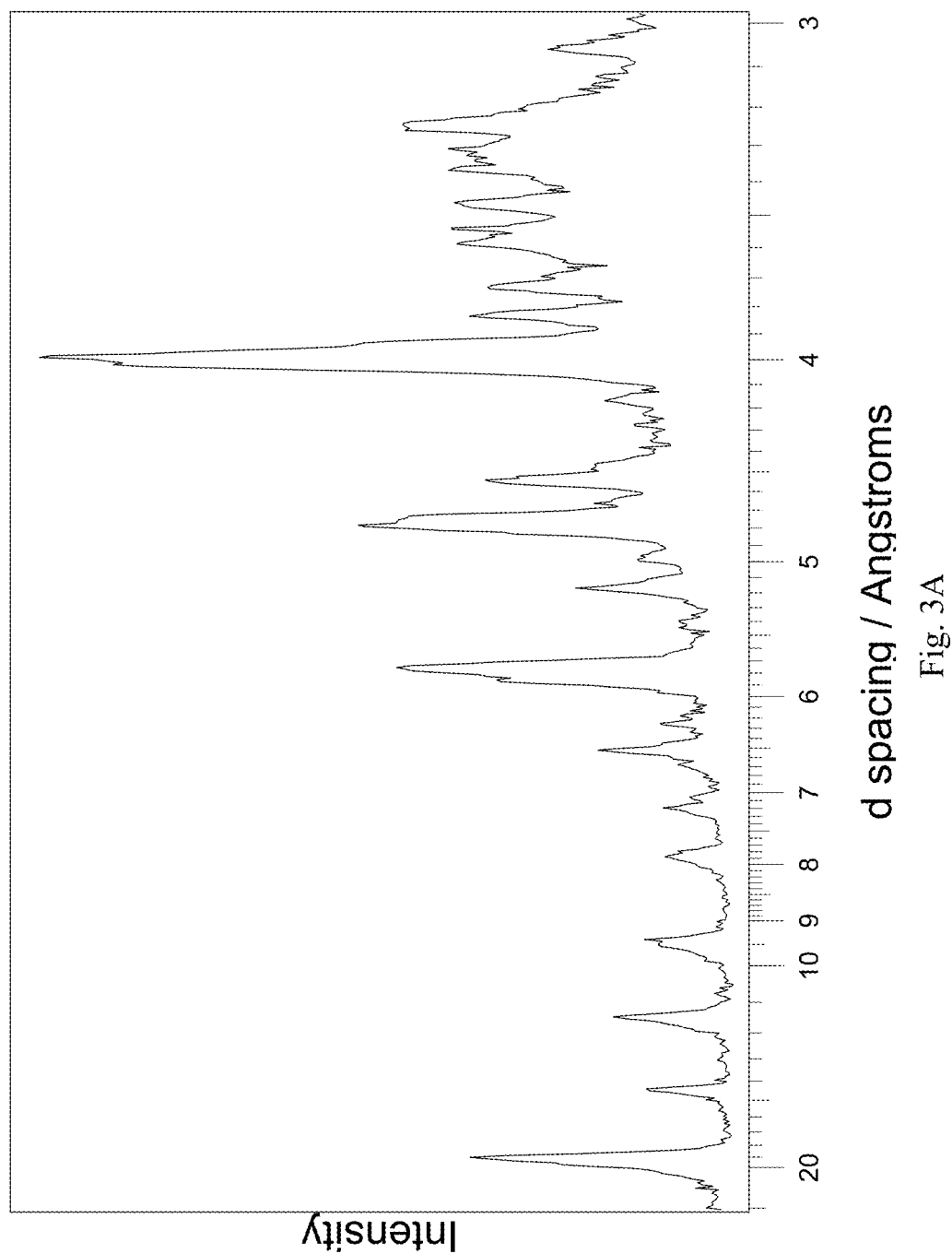
FIG. 3A-3D shows, for (3R,4S)-1-((4-amino-5H-pyrrolo[3,2-d]pyrimidin-7-yl)methyl)-4-(methylthiomethyl)pyrrolidin-3-ol phosphate, Form D, isolated from 60/40 water/ethanol: (A) X-ray powder diffraction (measured using a Phillips PW1700 diffractometer); (B) TGA, initial weight loss of 4.6% (scanning from ambient temperature to 300° C.; scan rate 10° C./min); (C) DSC trace (measured using an Alphatec SDT Q600 instrument), melting endotherm onset at 163.30° C. (scanning from 25° C. to 300° C.; scan rate 10° C./min); (D) TGA derivative.
Figure 3B:
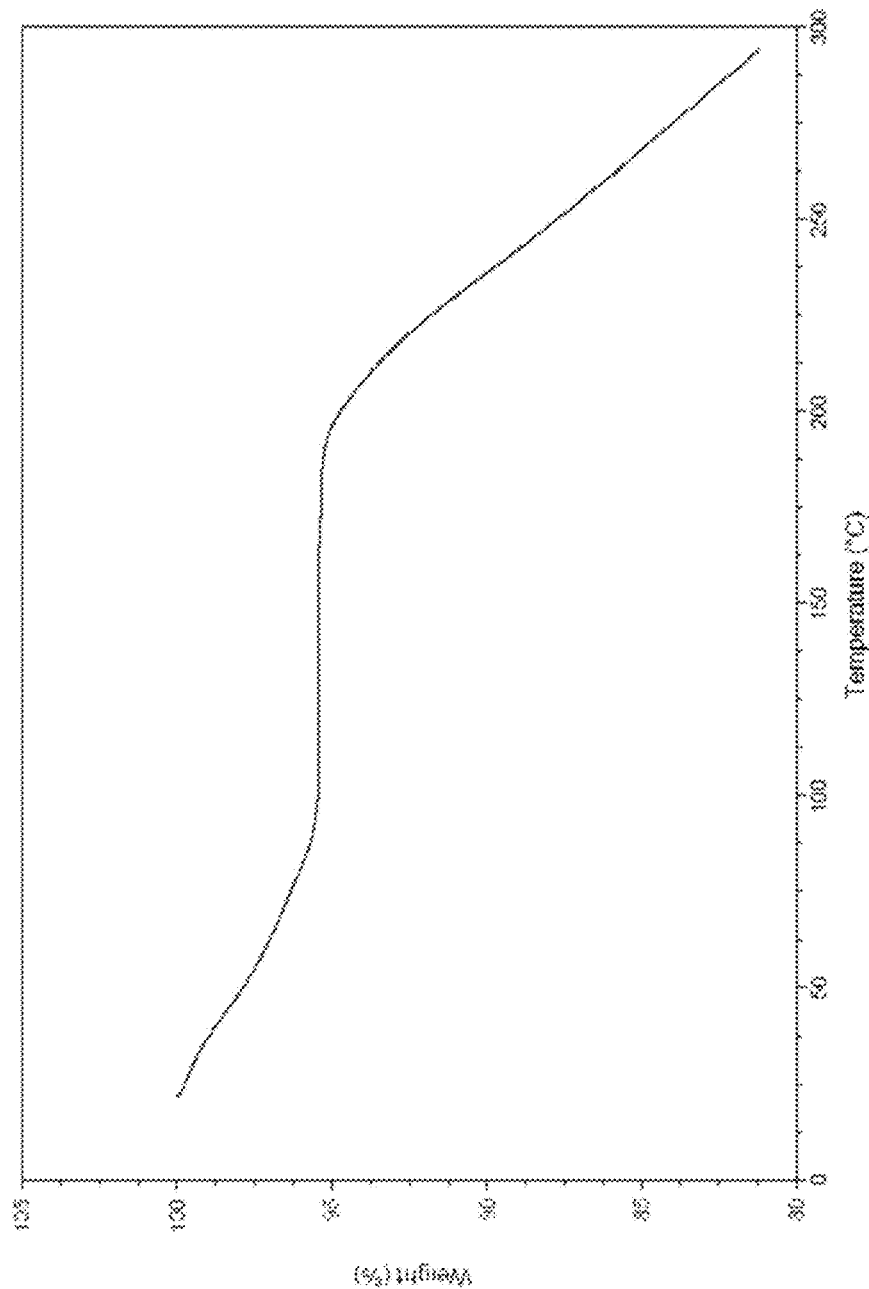
Figure 3C:
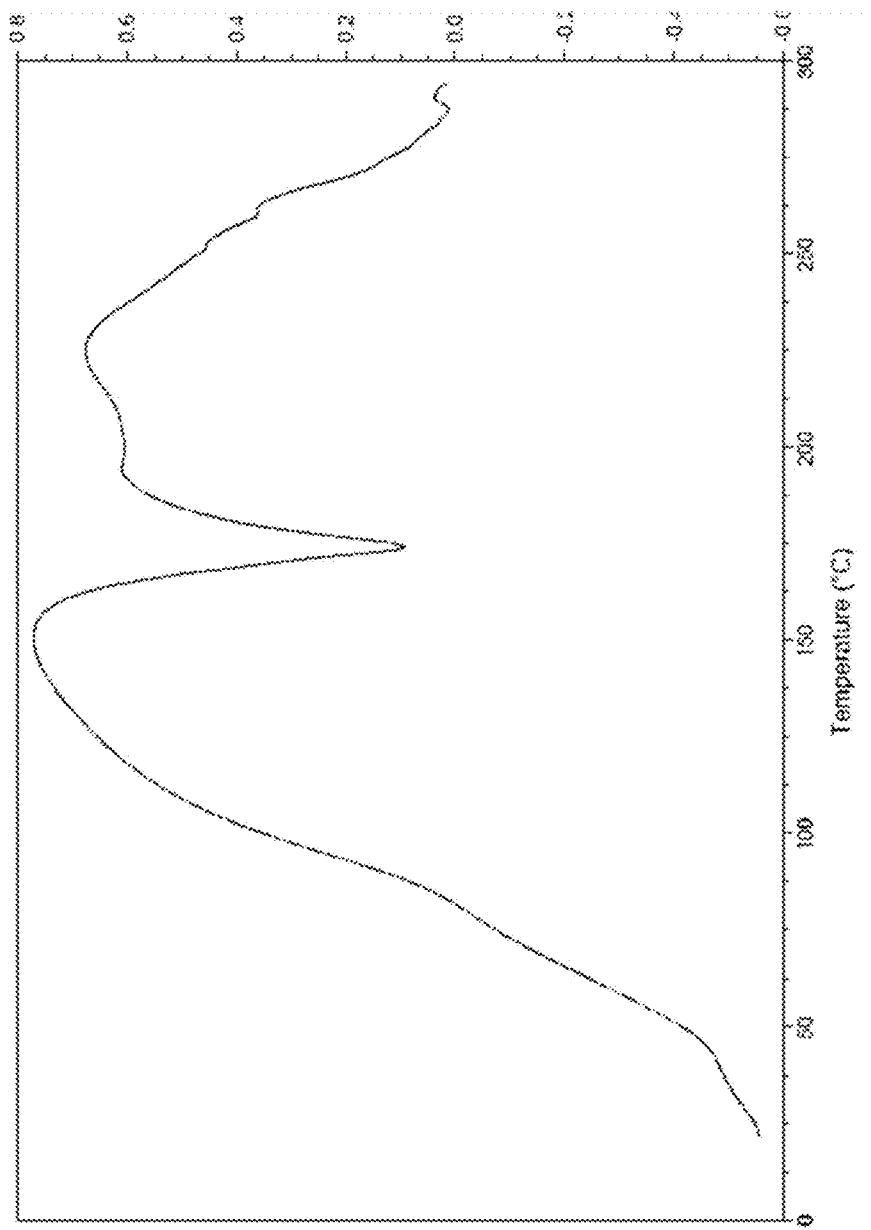
Figure 3D:
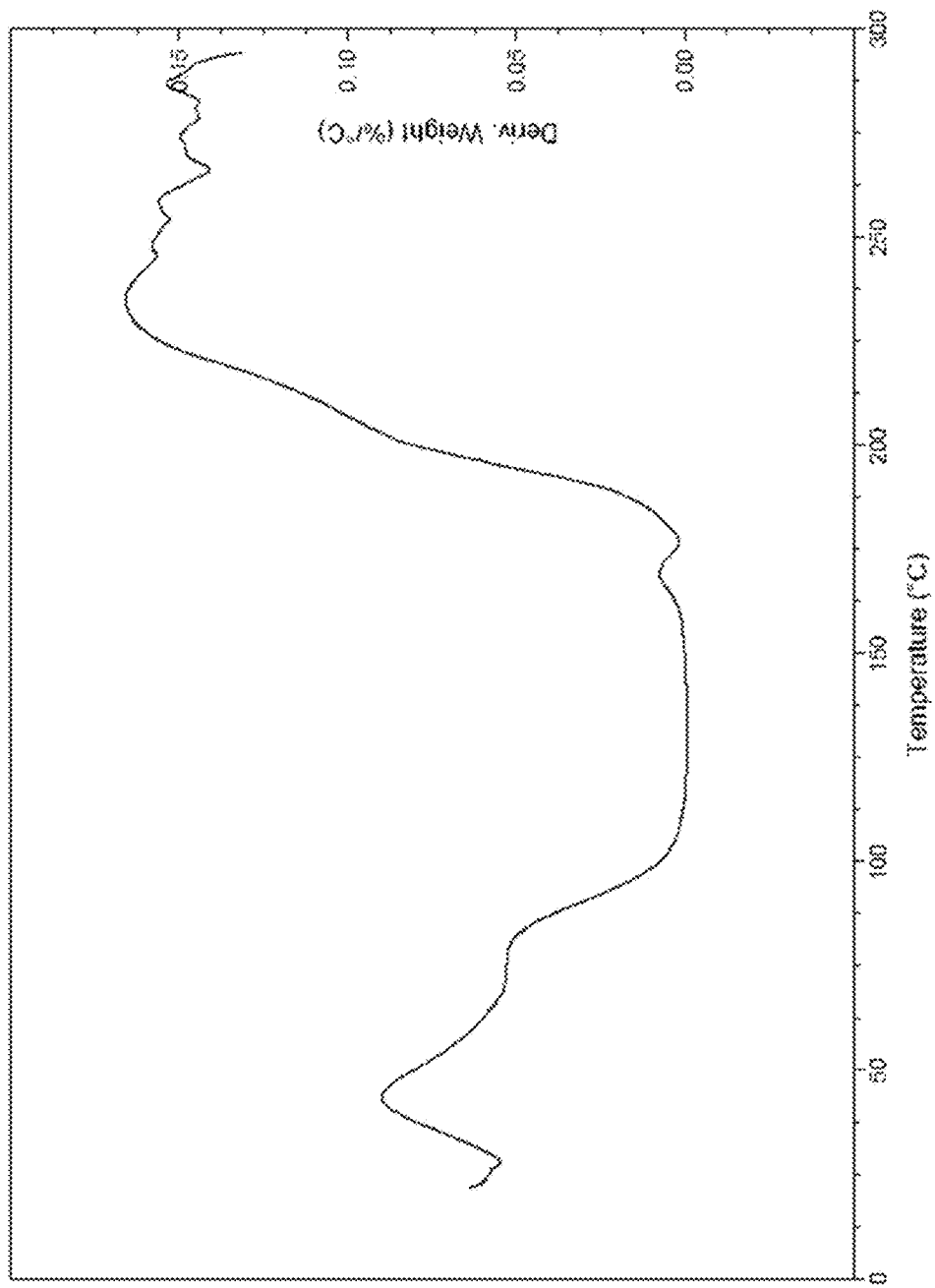
Figure 4A:
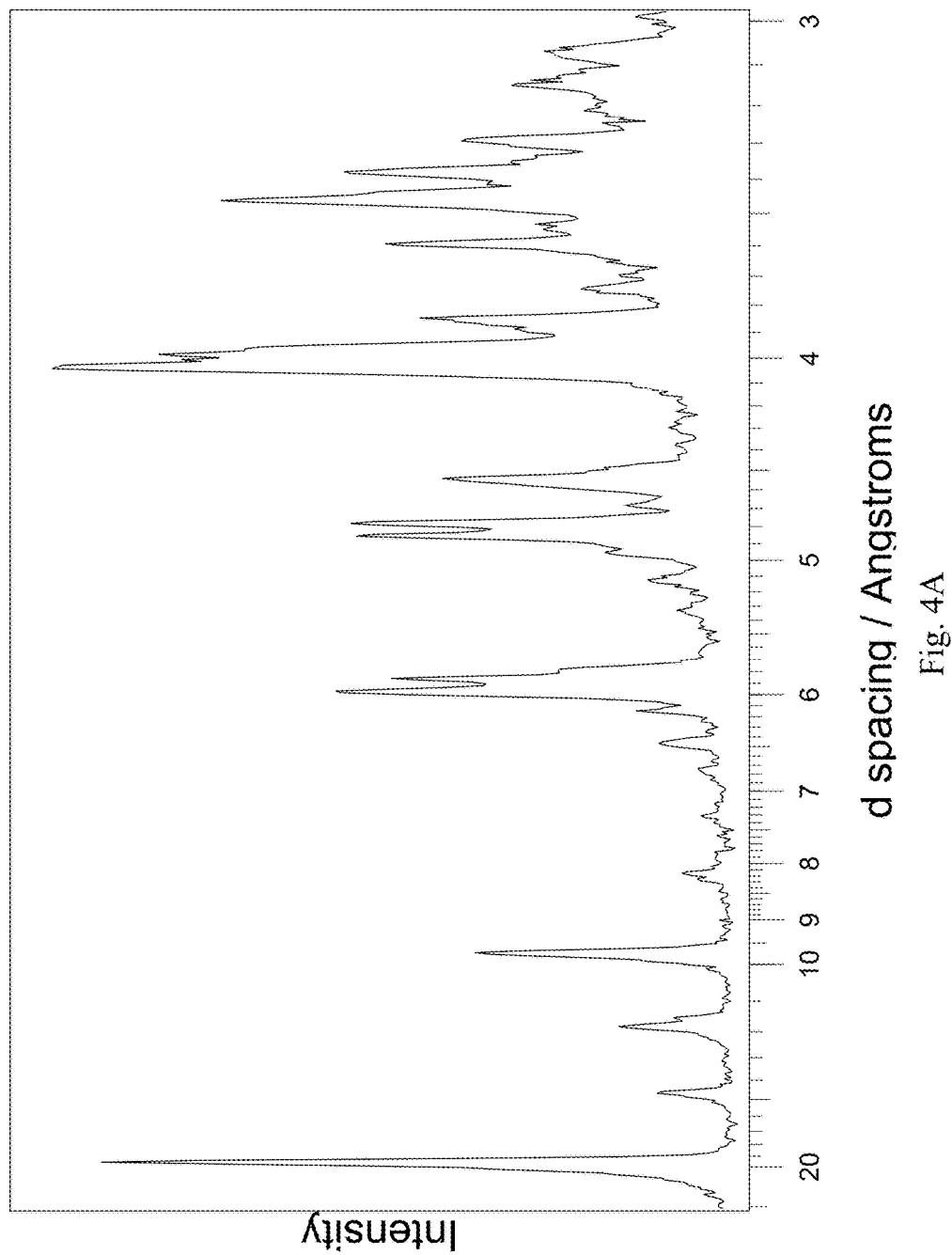
FIG. 4A-4D shows, for (3R,4S)-1-((4-amino-5H-pyrrolo[3,2-d]pyrimidin-7-yl)methyl)-4-(methylthiomethyl)pyrrolidin-3-ol phosphate, Form E, isolated from 3.6/6.4 water/ethanol: (A) X-ray powder diffraction (measured using a Phillips PW1700 diffractometer); (B) TGA, initial weight loss of 5.7% (scanning from ambient temperature to 300° C.; scan rate 10° C./min); (C) DSC trace (measured using an Alphatec SDT Q600 instrument), melting endotherm onset at 173.53° C. (scanning from 25° C. to 300° C.; scan rate 10° C./min); (D) TGA derivative.
Figure 4B:
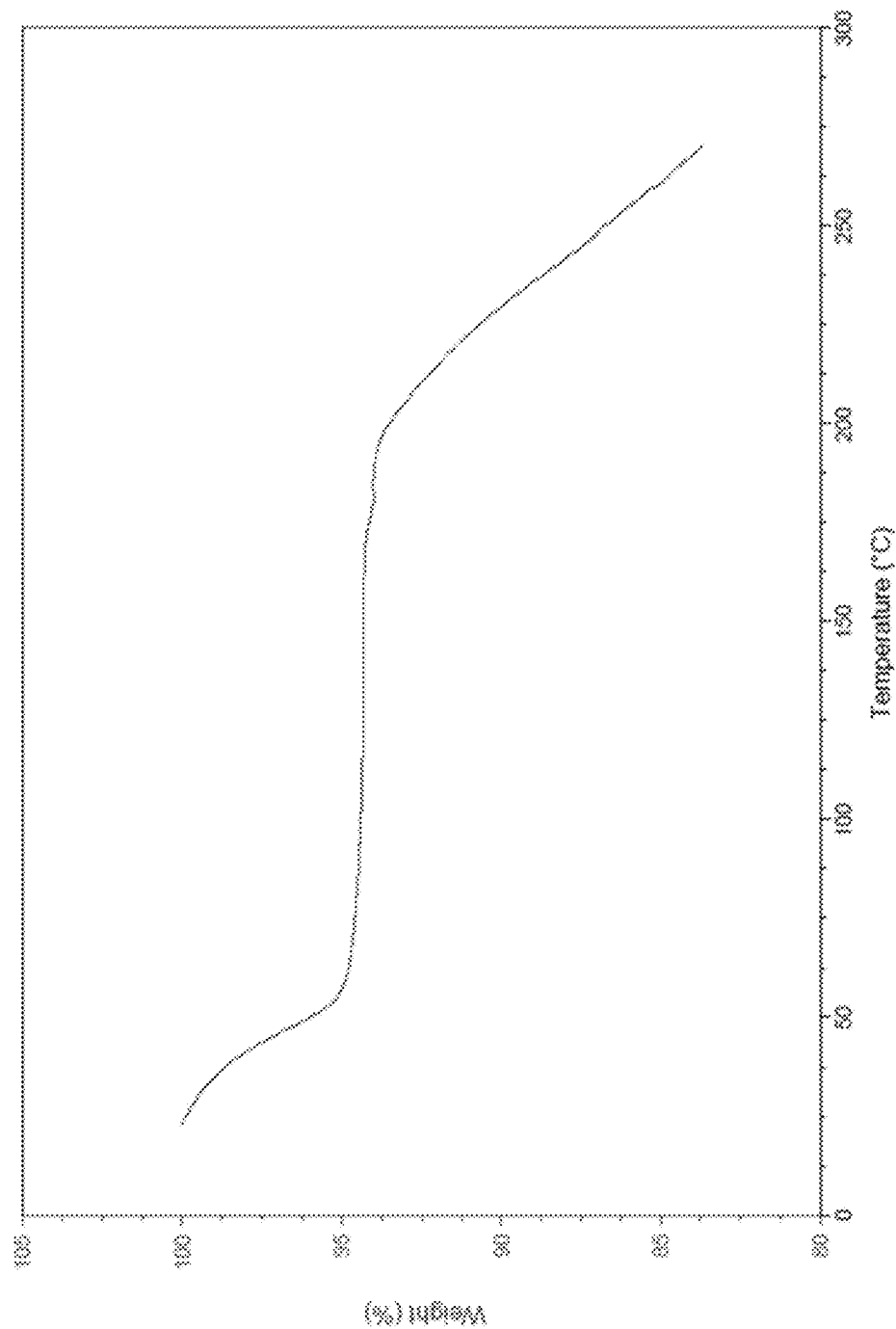
Figure 4C:
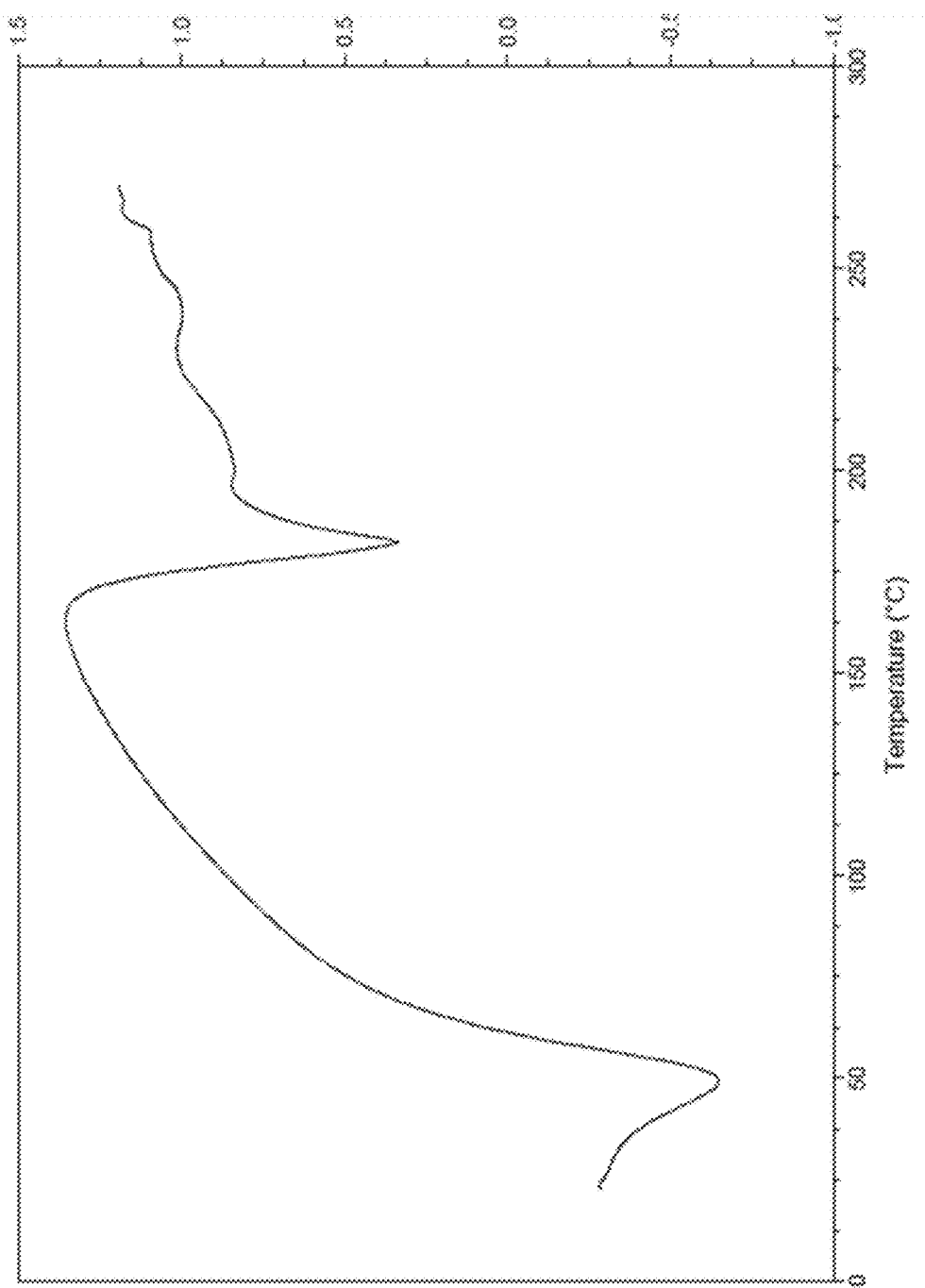
Figure 4D:
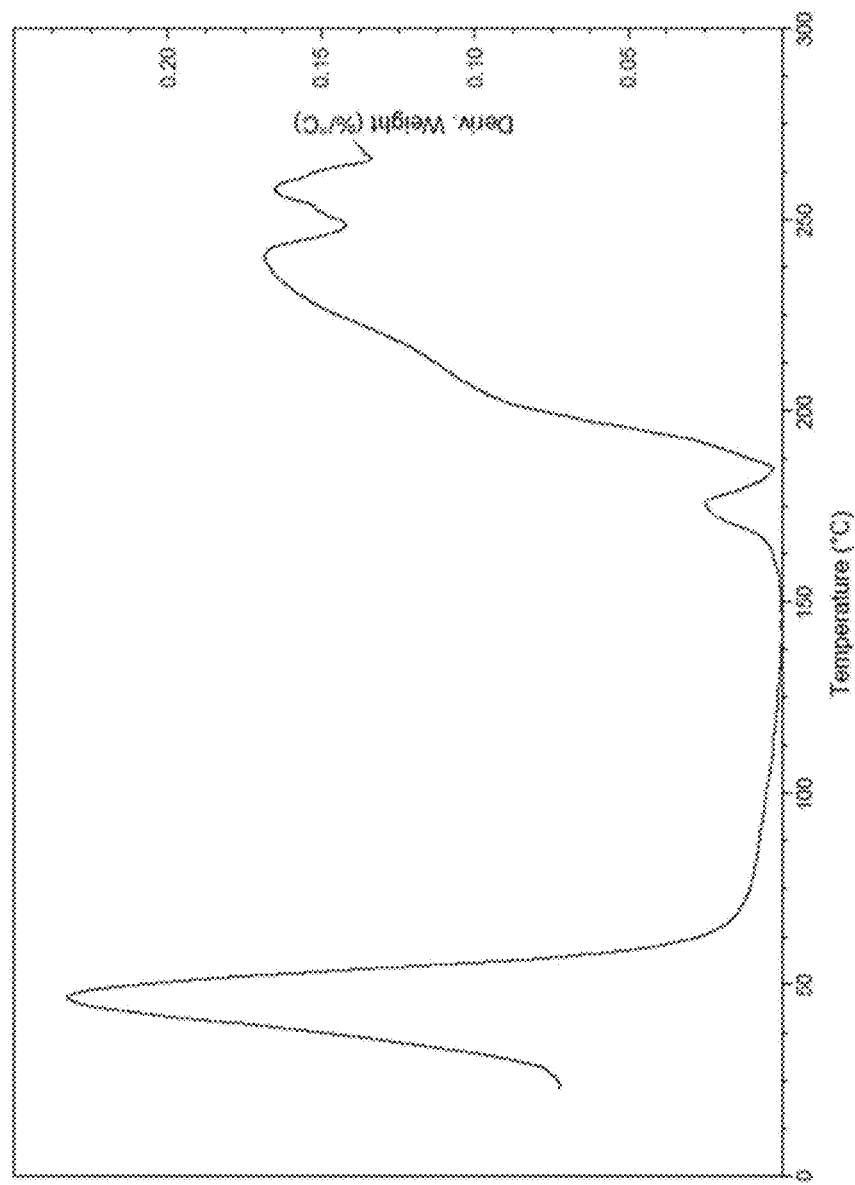
Figure 5A:
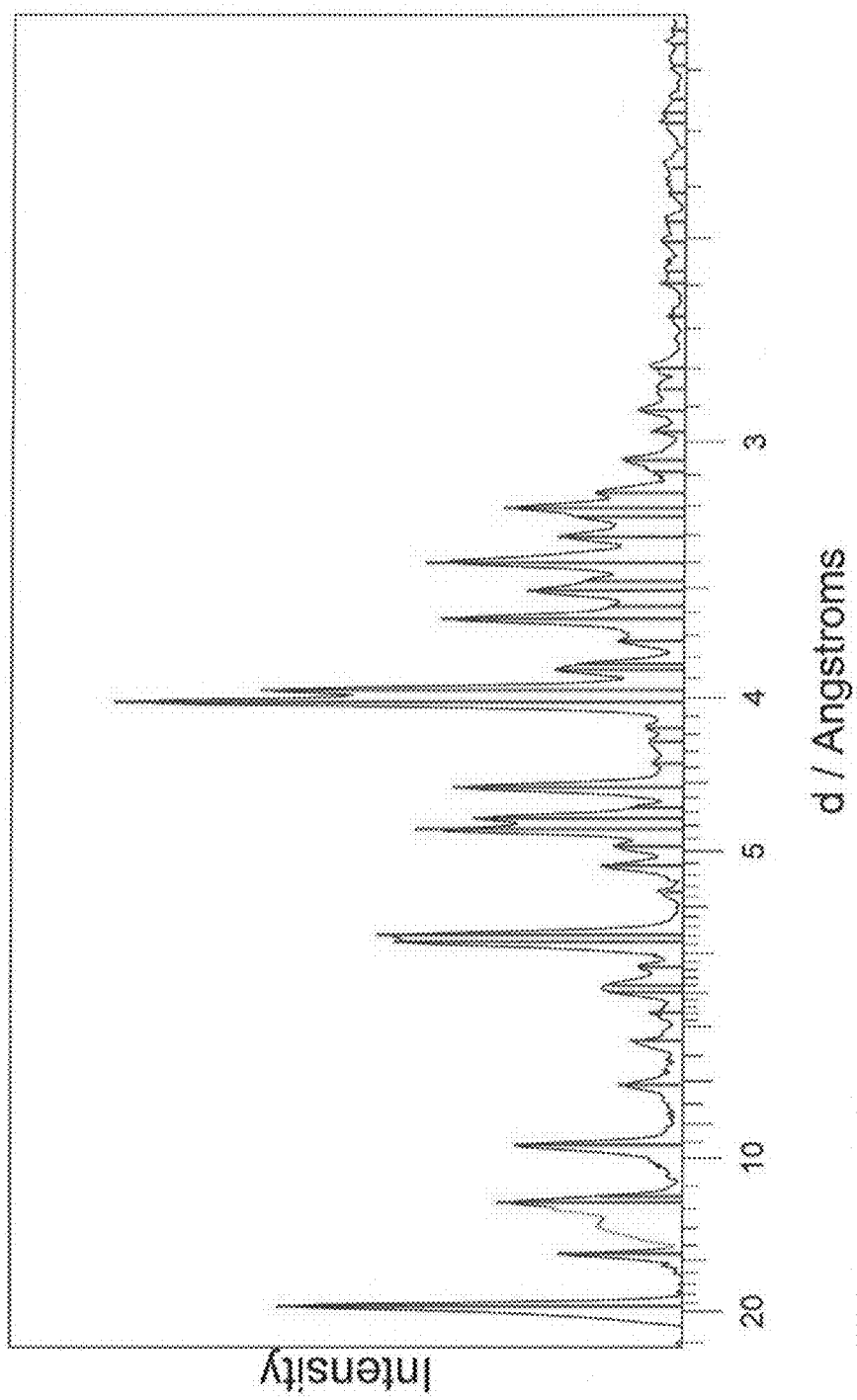
FIG. 5A-5D shows, for (3R,4S)-1-((4-amino-5H-pyrrolo[3,2-d]pyrimidin-7-yl)methyl)-4-(methylthiomethyl)pyrrolidin-3-ol phosphate, Form F, isolated from methanol: (A) X-ray powder diffraction (measured using a Phillips PW1700 diffractometer); (B) TGA, initial weight loss of 3.9 (scanning from ambient temperature to 275° C.; scan rate 10° C./min); (C) DSC trace (measured using an Alphatec SDT Q600 instrument), melting endotherm onset at 177.06° C. (scanning from 25° C. to 300° C.; scan rate 10° C./min); (D) TGA derivative.
Figure 5B:
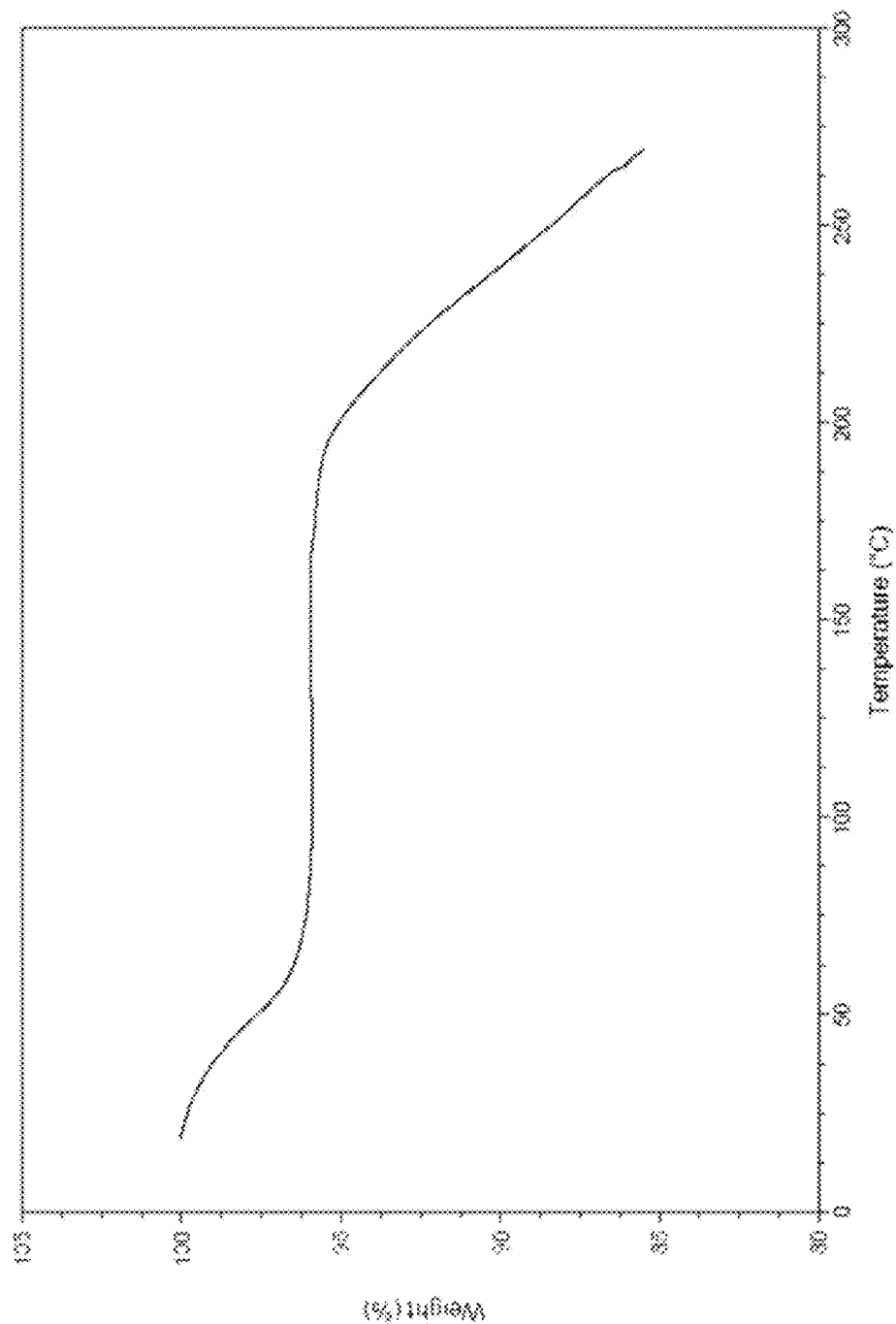
Figure 5C:
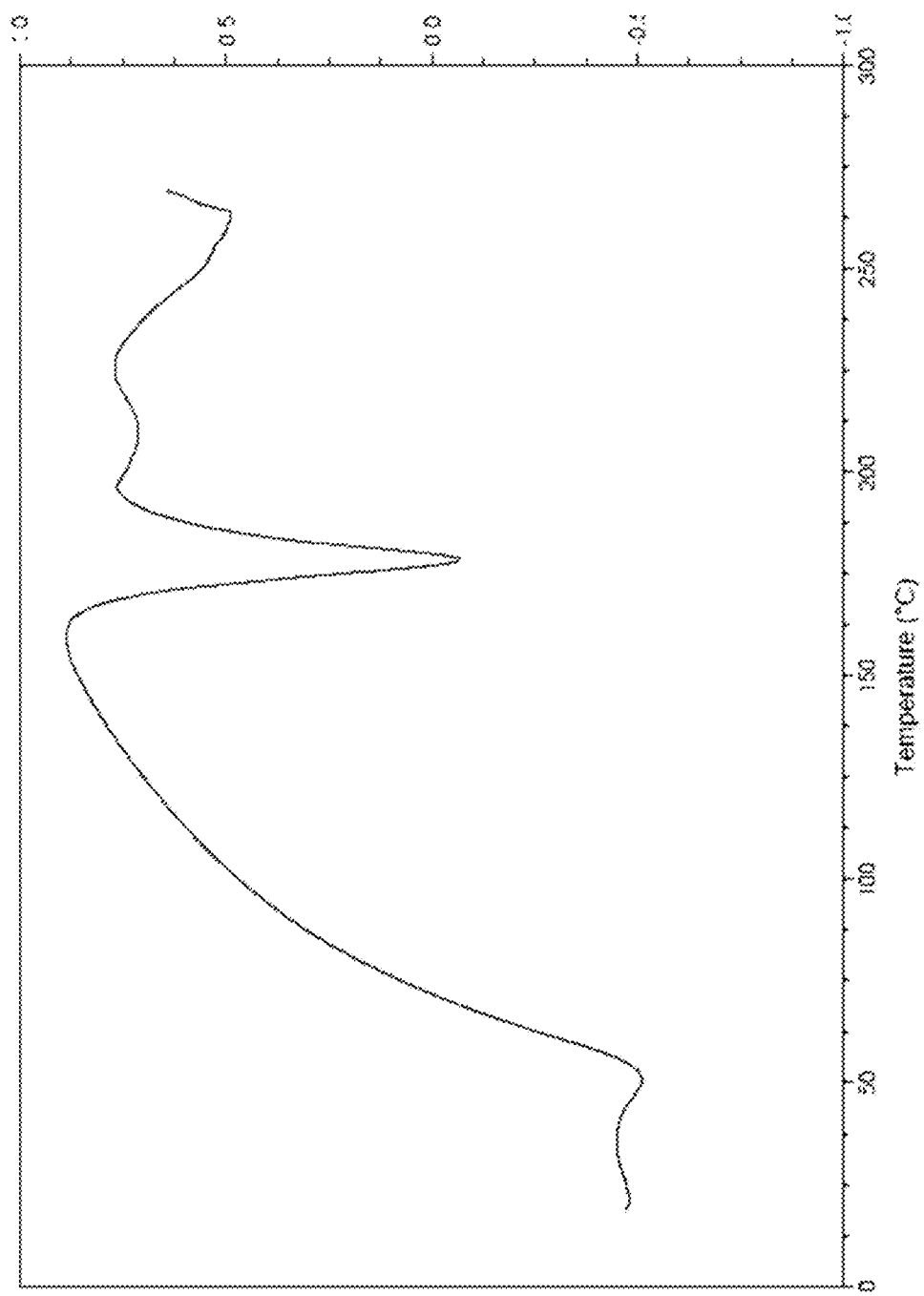
Figure 5D:
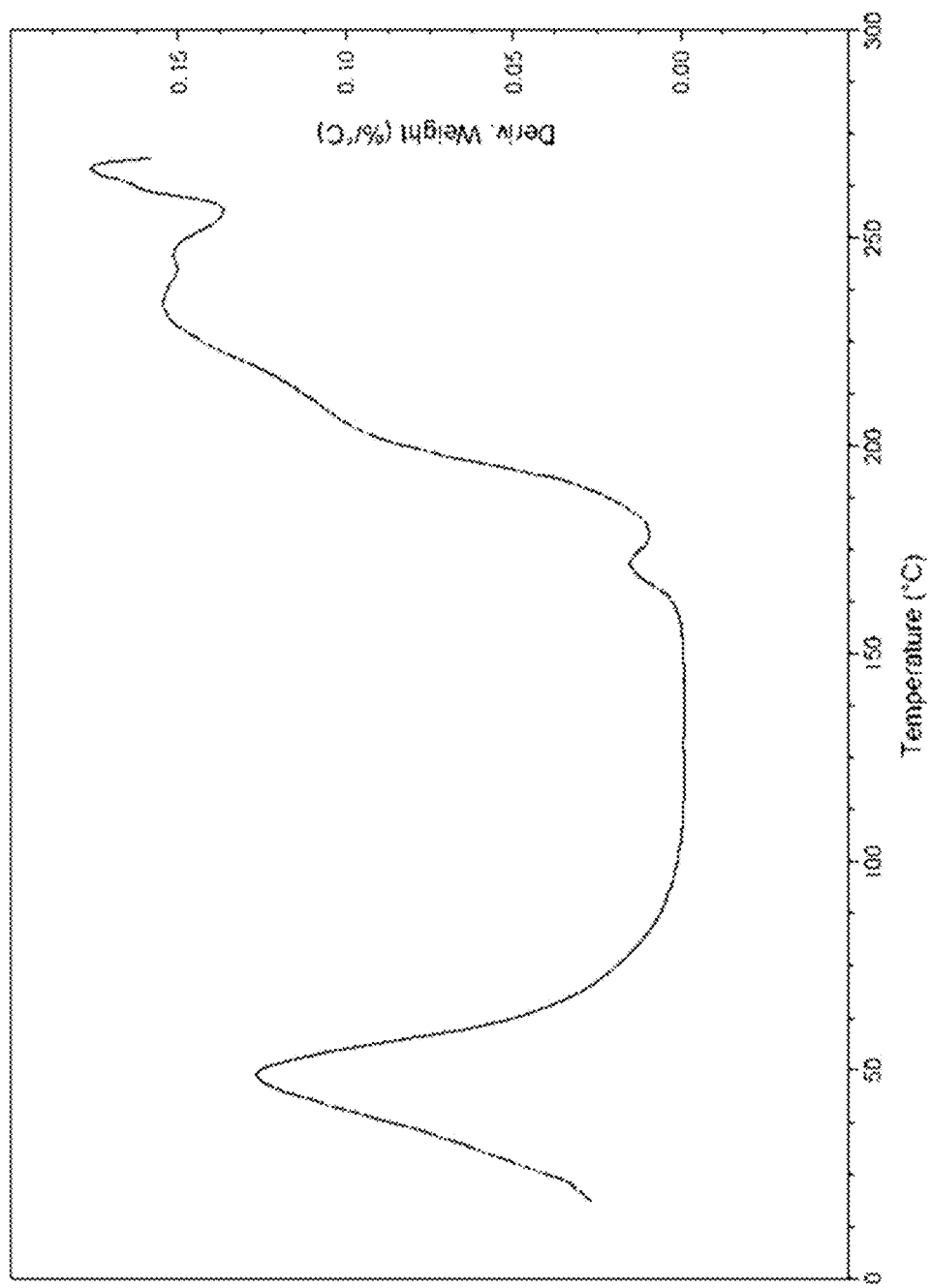
Figure 6A:
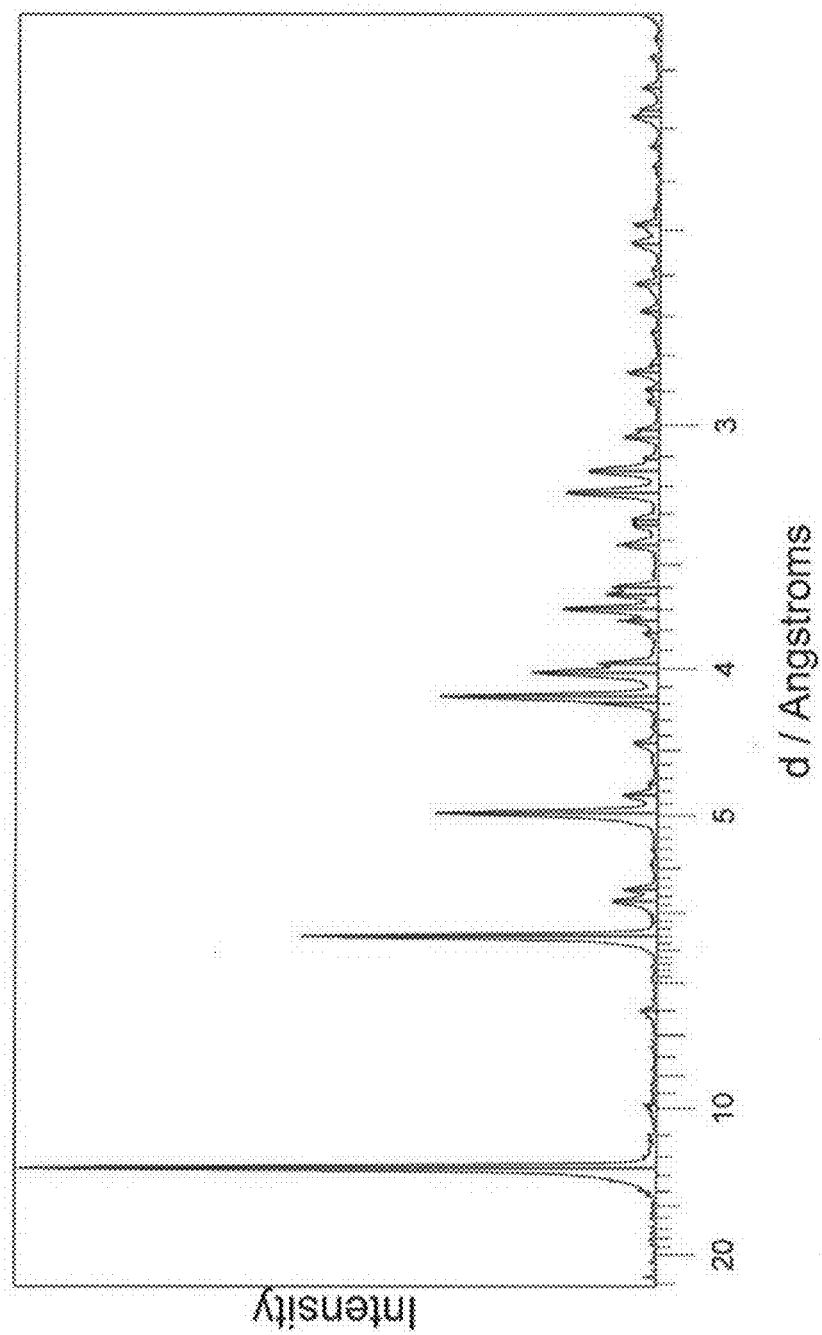
FIG. 6A-6D shows, for (3R,4S)-1-((4-amino-5H-pyrrolo[3,2-d]pyrimidin-7-yl)methyl)-4-(methylthiomethyl)pyrrolidin-3-ol formate, isolated from water/acetone: (A) X-ray powder diffraction (measured using a Bruker D8 Advance diffractometer); (B) TGA, no initial weight loss (scanning from ambient temperature to 275° C.; scan rate 10° C./min); (C) DSC trace (measured using an Alphatec SDT Q600 instrument), melting endotherm onset at 179.54° C. (scanning from 25° C. to 300° C.; scan rate 10° C./min); (D) TGA derivative.
Figure 6B:
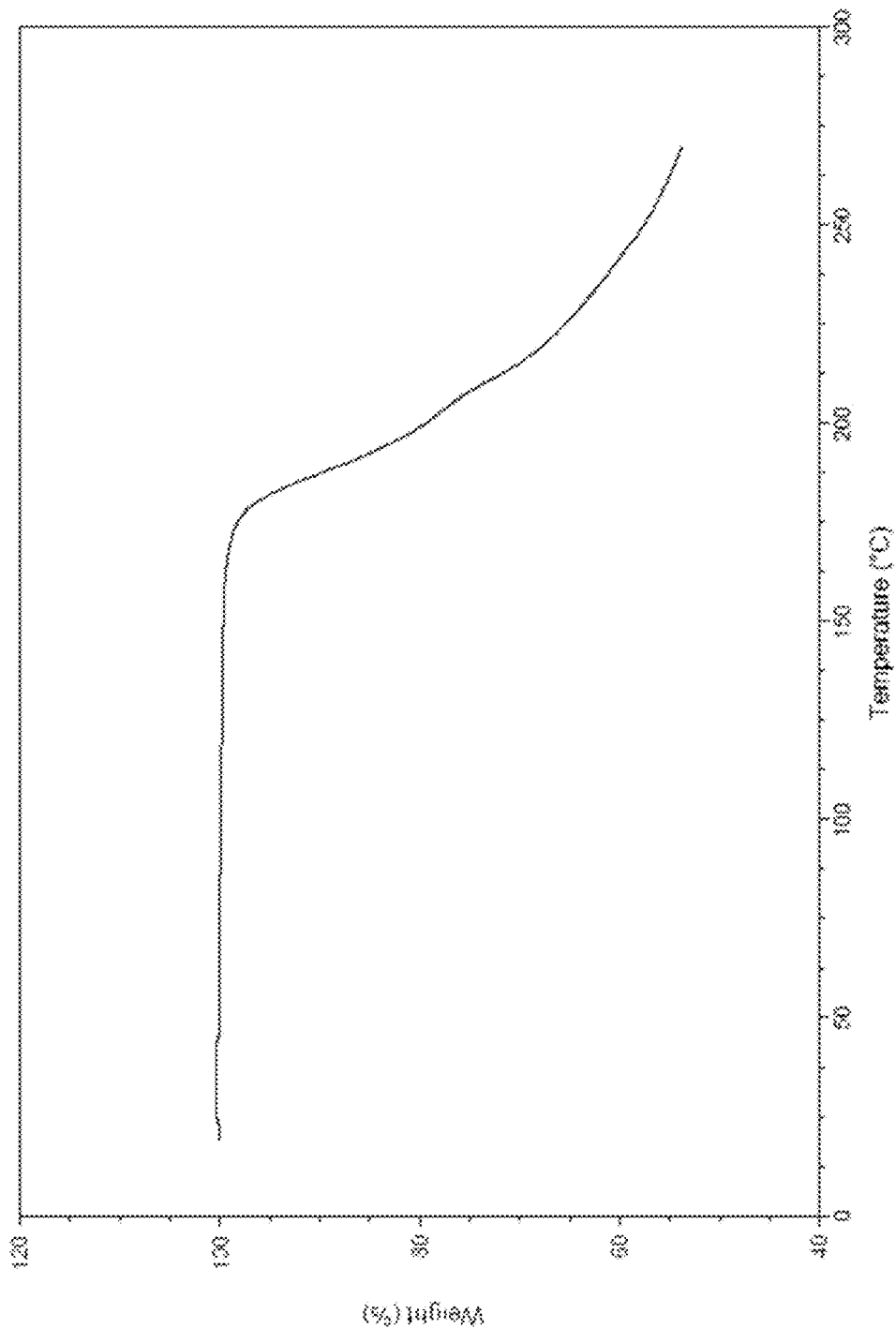
Figure 6C:
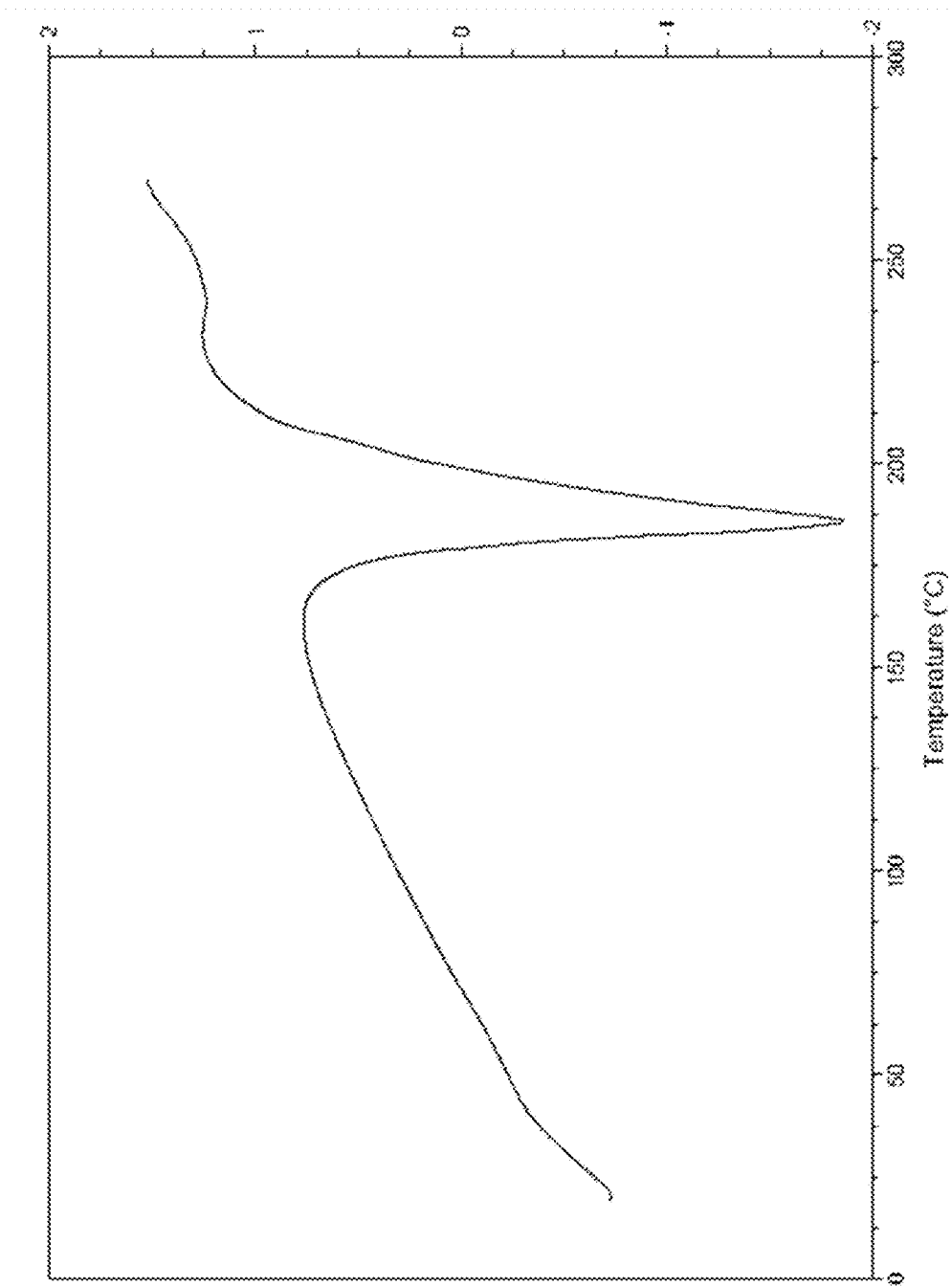
Figure 6D:
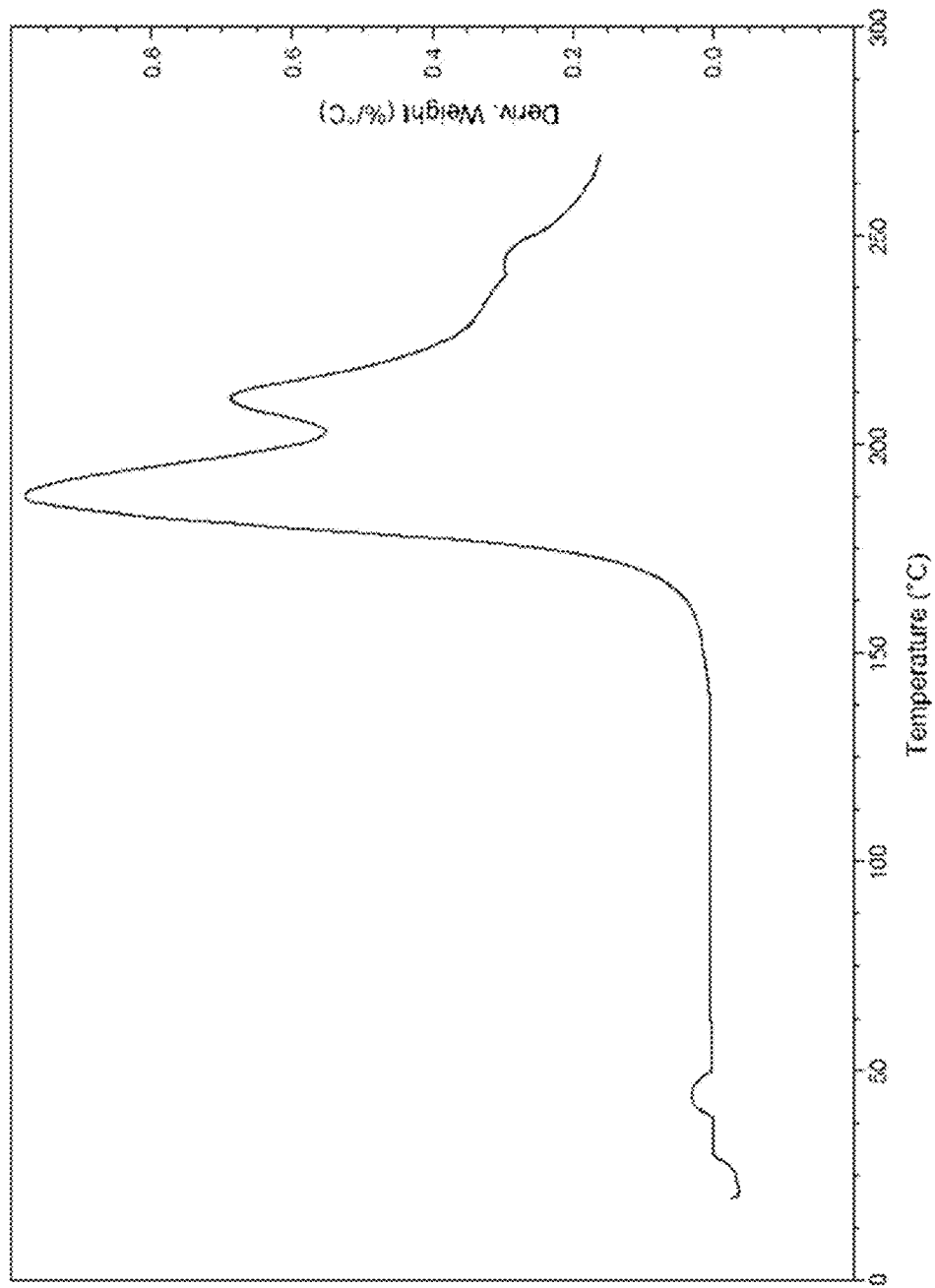
Figure 7A:
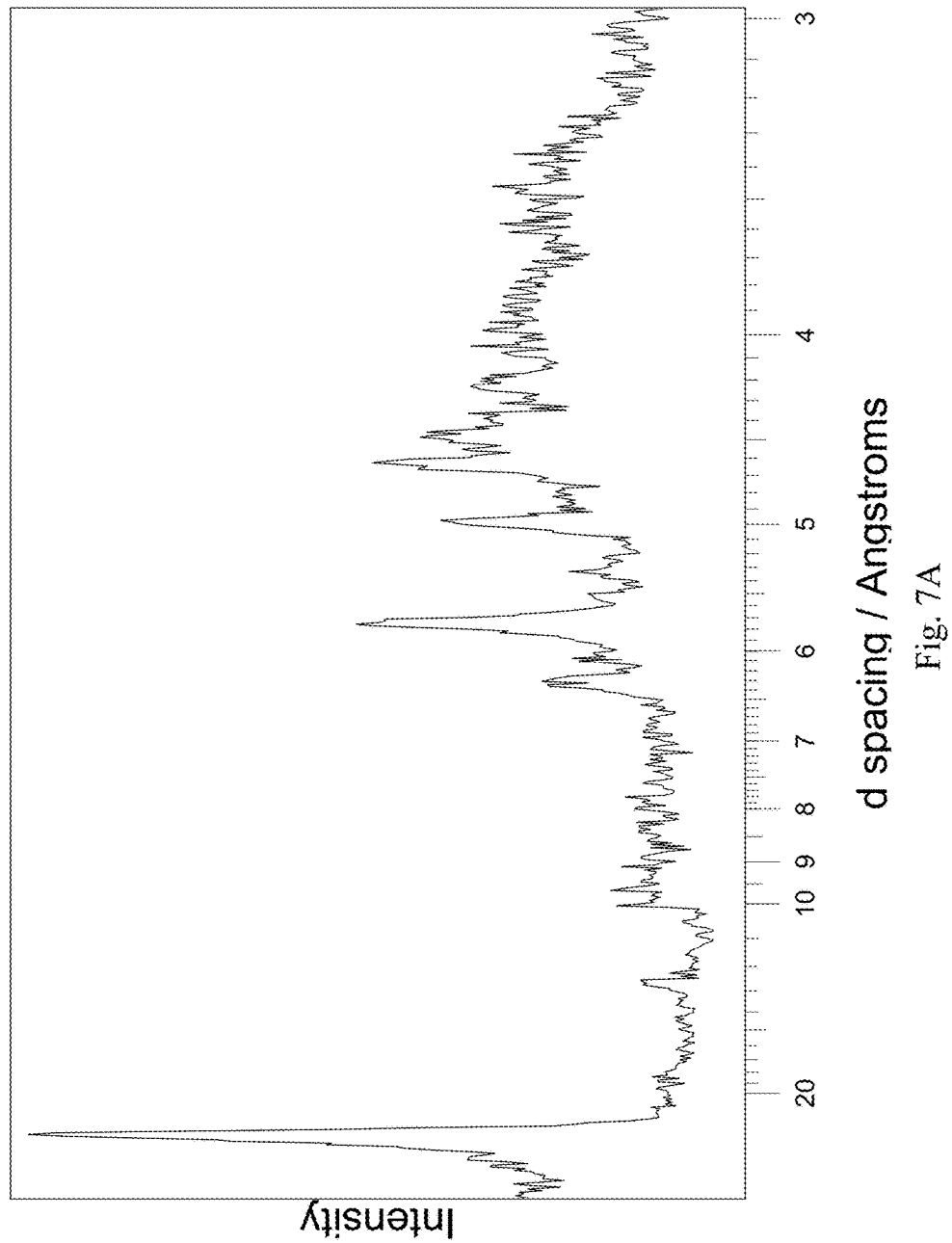
FIG. 7A-7B shows, for (3R,4S)-1-((4-amino-5H-pyrrolo[3,2-d]pyrimidin-7-yl)methyl)-4-(methylthiomethyl)pyrrolidin-3-ol: (A) XRPD (measured using a Bruker D8 Advance diffractometer); (B) DSC trace (measured using a Mettler-Toledo DSC1 Star-e system), melting endotherm onset is 184.82° C. (scanning from 25° C. to 300° C.; scan rate 10° C./min).
Figure 7B:
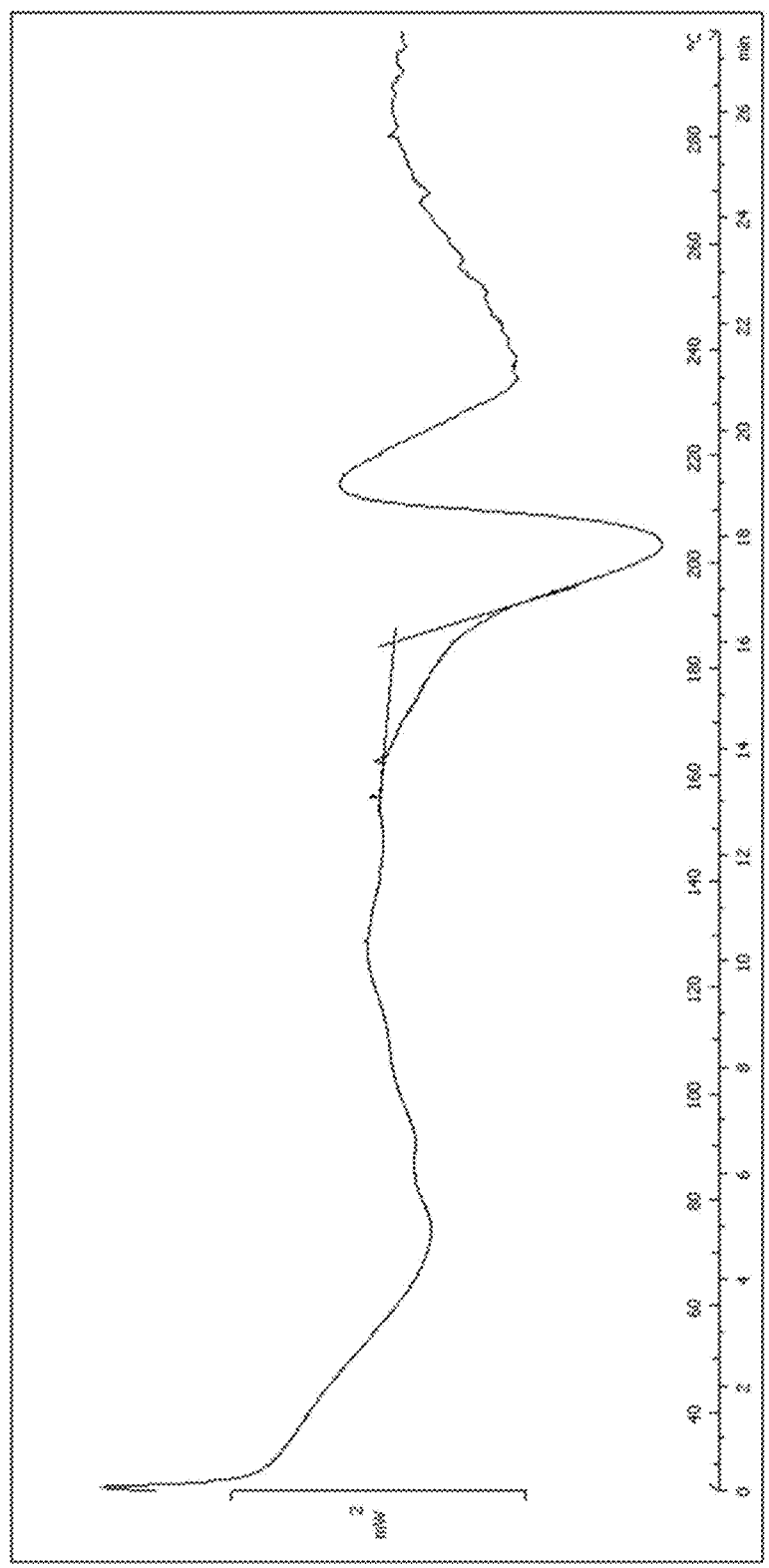
Figure 8:
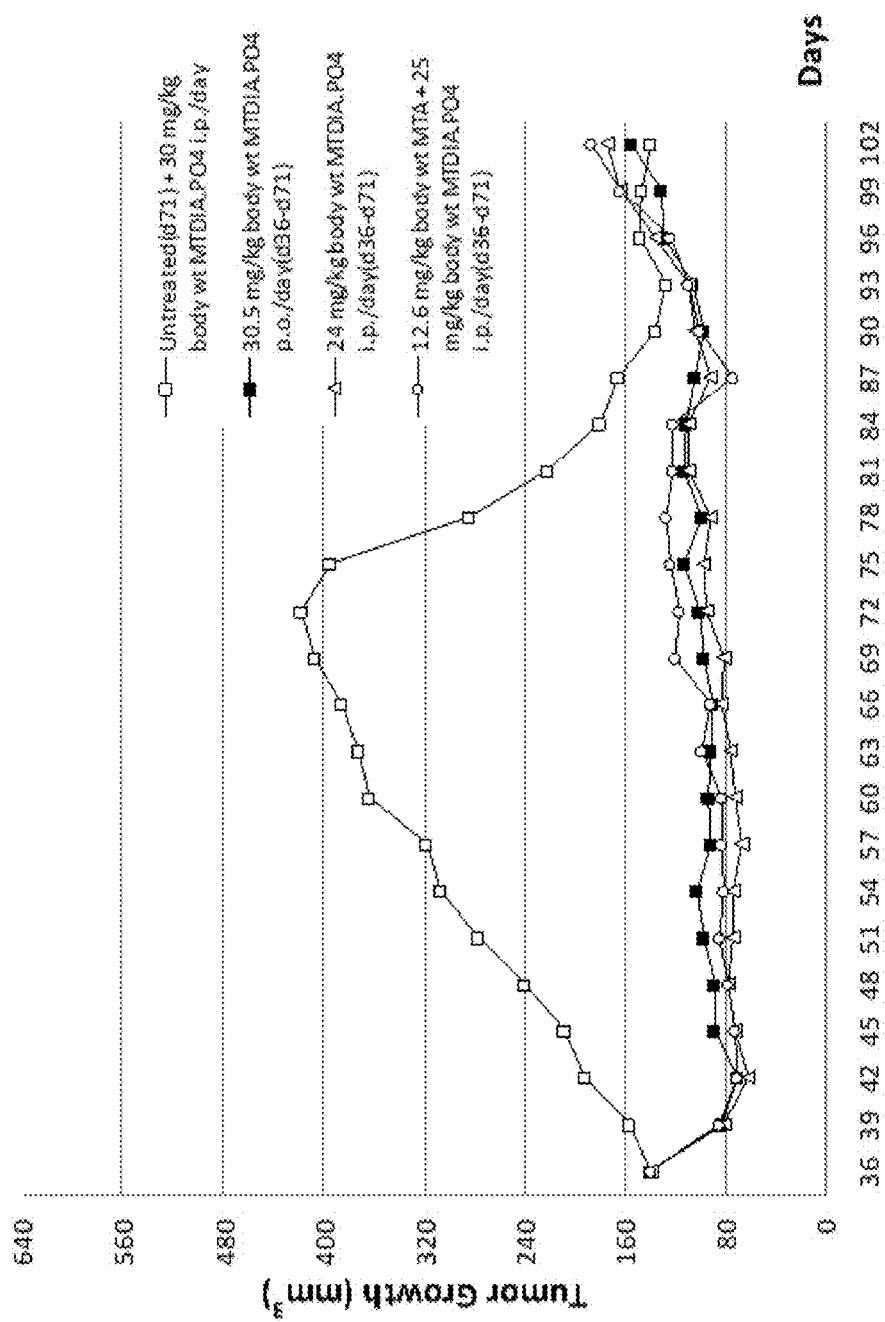
FIG. 8 shows a study of the effect of (3R,4S)-1-((4-amino-5H-pyrrolo[3,2-d]pyrimidin-7-yl)methyl)-4-(methylthiomethyl)pyrrolidin-3-ol phosphate on larger tumours (150 mm$^3$).
Figure 9A:
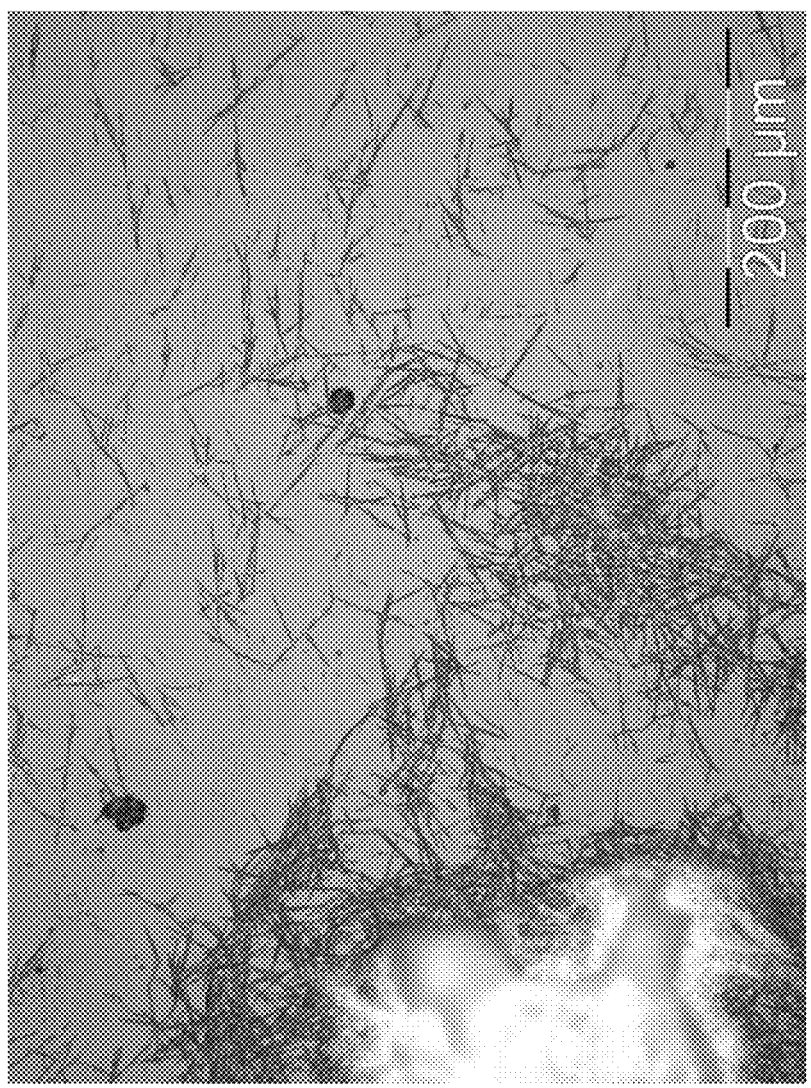
FIG. 9A-9B shows images of crystals of (3R,4S)-1-((4-amino-5H-pyrrolo[3,2-d]pyrimidin-7-yl)methyl)-4-(methylthiomethyl)pyrrolidin-3-ol phosphate, Form E, at (A) 20 times magnification and (B) 50 times magnification.
Figure 9B:
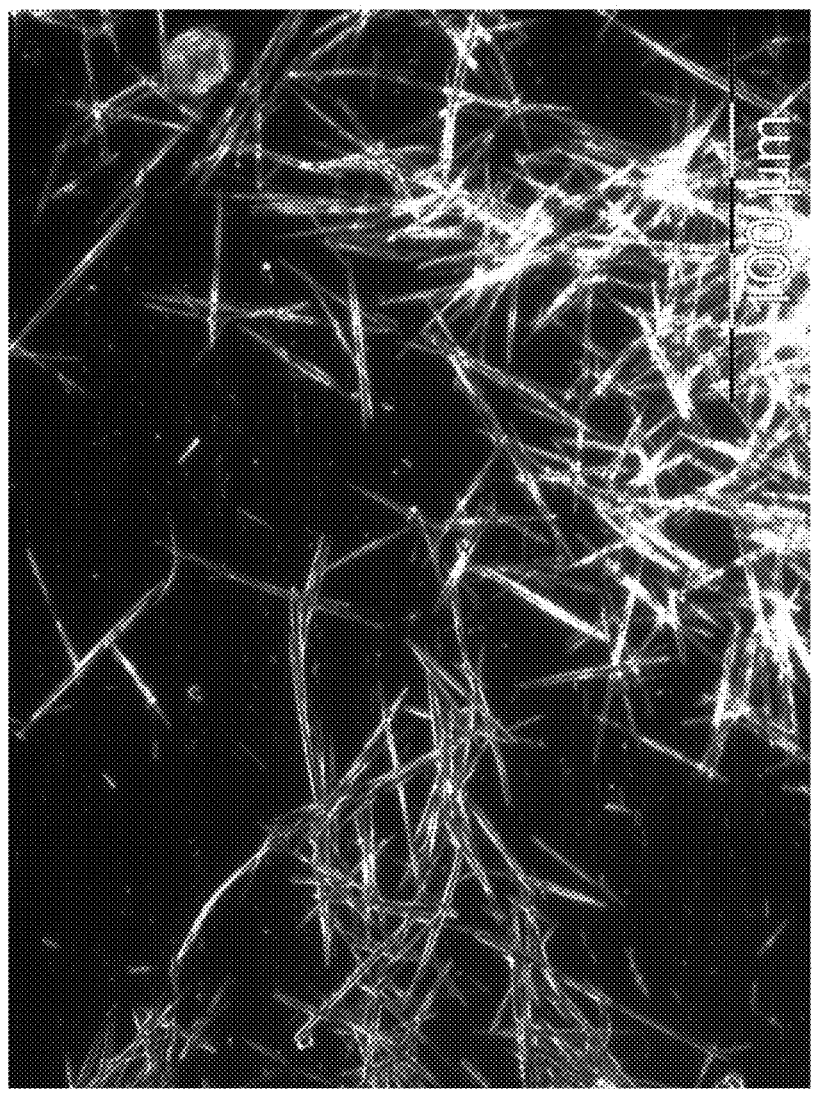

DBU 1,8-diazabicycloundec-7-ene
DCM dichloromethane
DSC differential scanning calorimetry
XRPD X-ray powder diffraction
TLC thin layer chromatography
TFA trifluoroacetic acid
TGA thermogravimetric analysis
DMAP 4-dimethylaminopyridine
MTBE methyl t-butyl ether
IPA isopropyl alcohol
HPLC high performance liquid chromatography
DSC differential scanning calorimetry
GC gas chromatography

EXAMPLES

General

X-ray powder diffraction patterns are obtained using parallel beam X-ray powder diffractometry using Co Kα radiation using either a Bruker D8 Advance diffractometer (for (3R,4S)-1-((4-amino-5H-pyrrolo[3,2-d]pyrimidin-7-yl)methyl)-4-(methylthiomethyl)pyrrolidin-3-ol and (3R,4S)-1-((4-amino-5H-pyrrolo[3,2-d]pyrimidin-7-yl)methyl)-4-(methylthiomethyl)pyrrolidin-3-ol sulfate, oxalate and formate) or a Philips PW1700 diffractometer (for (3R,4S)-1-((4-amino-5H-pyrrolo[3,2-d]pyrimidin-7-yl)methyl)-4-(methylthiomethyl)pyrrolidin-3-ol phosphate forms). The Bruker D8 Advance is equipped with 300 mm goniometer radius, an incident beam goebel mirror and 0.23 degree parallel plate diffracted beam collimator. The detector is a NaI(Tl) scintillation counter. The Philips PW1700 series Bragg-Brentano diffractometer is equipped with 173 mm goniometer radius, automatic divergence and 1 degree fixed antiscatter slits, 0.2 mm receiving slit and graphite diffracted beam monochromator. The detector is a xenon filled proportional counter.

Differential scanning calorimetry is performed on either a Mettler-Toledo DSC1 Star-e system or an Alphatec SDT Q600 instrument, scanning from 25° C. to 300° C.; scan rate 10° C. per minute.

Thermogravimetric analysis is performed on an Alphatec SDT Q600 instrument, scanning from ambient temperature to either 300° C. or 275° C.; scan rate 10° C. per minute.

Example 1: Synthesis of Compound (Ia) (3R,4S)-1-((4-amino-5H-pyrrolo[3,2-d]pyrimidin-7-yl)methyl)-4-(methylthiomethyl)pyrrolidin-3-ol Phosphate Compound (III) (E)-ethyl 2-cyano-3-(cyanomethylamino)acrylate

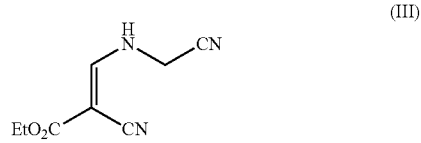 [SMILES: CCOC(=O)/C(C#N)=C/NCC#N]

(III)

Aminoacetonitrile bisulfate (22.8 g, 0.148 mols) in methanol (0.5 L, AR grade) is agitated for sufficient time so as to break up and dissolve any lumps of material present. Acrylate (25 g, 0.148 mols) is charged to the mixture and the temperature cooled to 5-10° C. Triethylamine (45.3 ml, 0.33 mols) is added gradually so as to maintain an internal temperature of less than 20° C. The mixture is agitated for 2 hours and analysed by TLC for consumption of starting material. The solvent is removed in vacuo and the residue is dissolved in ethyl acetate (0.3 L) then washed with saturated aqueous sodium bicarbonate (0.2 L) and brine (0.08 L, 30%). The ethyl acetate solution is concentrated to give the product in quantitative yield before dissolution with an equal volume of fresh ethyl acetate (AR grade) for use in the next step (characterised as a 60:40 isomeric mixture, H'=minor isomer protons). $\delta_H$ (500 MHz, d$^6$-DMSO) 1.21 (3H, t, J 7.1), 1.23 (3H', t, J 7.2), 4.14 (2H, q, J 7.1), 4.17 (2H', q, J 7.2), 4.44 (2H', s), 4.53 (2H, s), 7.86 (1H', bd, J 11.3), 8.16 (1H, s), 9.00 (1H, bs), 9.27 (1H', bs); $\delta_C$ (125 MHz, d$^6$-DMSO) 14.0, 14.3, 36.1, 36.8, 60.1, 71.9, 72.7, 115.7, 116.9, 116.9, 118.2, 159.9, 160.1, 164.3, 165.7; m.p. 95° C.; HRMS calculated for $C_8H_9N_3O_2Na$ m/z 202.0592, found 202.0590.

Compound (IV) (E)-ethyl 2-cyano-3-((cyanomethyl)(methoxycarbonyl)amino)acrylate

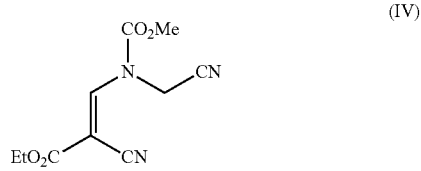 [SMILES: CCOC(=O)/C(C#N)=C/N(CC#N)C(=O)OC]

(IV)

Compound (III) (0.148 mols) in ethyl acetate is cooled to 5-10° C. Methyl chloroformate (12.6 ml, 0.163 mols) is added, followed by gradual addition of triethylamine (22.7 ml, 0.163 mols) so as to maintain an internal temperature of less than 25° C. After complete addition the reaction mixture is stirred for 10 minutes and then warmed to 20° C. The reaction mixture is washed with deionised water (0.15 L), aqueous saturated sodium bicarbonate (0.15 L) and brine (0.05 L, 30%). The solvent is removed in vacuo to give the product as orange oil in quantitative yield. $\delta_H$ (500 MHz, d$^6$-DMSO) 1.27 (3H, t, J 7.1), 3.94 (3H, s), 4.27 (2H, q, J 7.1), 5.07 (2H, s), 8.44 (1H, s); $\delta_C$ (125 MHz, d$^6$-DMSO) 14.0, 34.2, 56.0, 62.1, 83.6, 114.0, 115.3, 149.4, 151.9, 162.6; HRMS calculated for $C_{10}H_{11}N_3O_4Na$ m/z 260.0647, found 260.0652.

Compound (V) ethyl
4-amino-5-cyano-1H-pyrrole-3-carboxylate

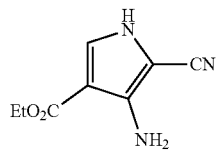

(V)

Compound (IV) (35.1 g, 0.148 mols) is dissolved in dichloromethane (0.39 L) and the temperature is adjusted to 27° C. DBU (12.5 ml, 0.083 mols) as a solution in dichloromethane (12.5 ml) is added to the solution of compound (IV) over approximately 1 minute with vigorous stirring. Once addition is complete, the mixture is agitated for 10 minutes and the jacket set to 20° C. Methanol (39 ml, AR grade) is added and the mixture is agitated for 15 minutes, followed by addition of ammonium acetate (7.98 g, 0.104 mols) as a solution in methanol (60 ml). The solvent is removed in vacuo and the residue slurried in absolute ethanol (70 ml). Water (280 ml) is gradually added to the slurry with stirring, and stirring continued for at least 2 hours. The mixture is then filtered, washed with water (80 ml) and dried under vacuum to give 19 g of solid (72%) of 80% purity as established by IPC. IPC is performed using a Kinetix C18 2.6µ 100×3.0 mm column, at 40° C. with a flow rate of 0.3 ml/min and a sample concentration of 0.5 mg/ml at a wavelength of 255 nm. Solvent A is water+0.1% TFA and solvent B is acetonitrile+0.1% TFA; gradient conditions are 0-20 mins, A:B, 9:1; 20-22 mins, A:B, 1:1; 22-27 mins, A:B, 9:1. $\delta_H$ (500 MHz, d$^6$-DMSO) 1.26 (3H, t, J 7.1), 4.20 (2H, q, J 7.1), 5.65 (2H, s), 7.35 (1H, s), 11.8 (1H, bs); $\delta_C$ (125 MHz, d$^6$-DMSO) 14.3, 59.1, 84.4, 102.3, 114.8, 127.4, 146.0, 164.0; m.p. 205° C.; HRMS calculated for $C_8H_9N_3O_2Na$ m/z 202.0592, found 202.0591.

Compound (VI) ethyl 4-amino-5H-pyrrolo[3,2-d]pyrimidine-7-carboxylate

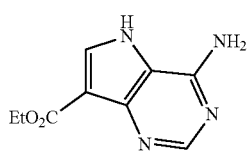

(VI)

Compound (V) (19.1 g, 0.107 mol), formamidine acetate (16.7 g, 0.16 mols), and formamide (0.2 L, AR grade) are charged to a vessel and heated at 90° C. for 20 hours. The mixture is cooled to below 50° C., water (0.3 L) is added to the stirred suspension and the temperature adjusted to 10-20° C. After 2 hours equilibration the mixture is filtered and the solid is washed with water (50 ml) and briefly air dried. The dried solid is obtained in 16-18 g (90-100% yield when adjusted for 80% purity of the starting material). The product is of lower solubility than the starting material and purity is determined by IPC analysis and calculation of the reduction of starting material IPC is performed using a Kinetix C18 2.6µ 100×3.0 mm column, at 40° C. with a flow rate of 0.25 ml/min and a sample concentration of 0.5 mg/ml at a wavelength of 205 nm. Solvent A is water+0.1% TFA and solvent B is acetonitrile+0.1% TFA; gradient conditions are 0-25 mins, A:B, 9:1; 25-26 mins, A:B, 4:6; 26-31 mins, A:B, 9:1. $\delta_H$ (500 MHz, d$^6$-DMSO) 1.29 (3H, t, J 7.1), 4.25 (2H, q, J 7.1), 6.85 (2H, bs), 8.16 (1H, s), 8.20 (1H, s), 11.6 (1H, bs).

Compound (VII)
5H-pyrrolo[3,2-d]pyrimidin-4-amine

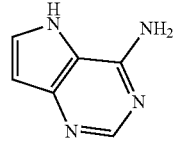

(VII)

Wet compound (VI) (assumed dry weight 17.6 g, 0.085 mols) as a suspension in water (215 ml) is treated with potassium hydroxide (12.0 g, 0.21 mols). The mixture is gently refluxed at 120° C. After 6 hours the mixture is analysed for completion by IPC. Heating and IPC analysis is continued until starting material is consumed. The mixture is cooled to 2-8° C. and stirred for 2 hours. The mixture is filtered, the solid collected and washed with water (40 ml). The damp solid is dried under vacuum at 20-40° C. to give 9-10 g (80-90% purity as determined by IPC) of a beige solid. IPC is performed using an Atlantis T3 3µ 150×4.6 mm column, at 20° C., with a flow rate of 1.0 ml/min, a sample concentration of 0.5 mg/ml at a wavelength of 273 nm. Solvent A is water+0.1% TFA and solvent B is acetonitrile+ 0.1% TFA; gradient conditions are 0-15 mins, A:B, 10:0; 15-16 mins, A:B, 8:2; 16-21 mins, A:B, 10:0. $\delta_H$ (500 MHz, d$^6$-DMSO) 6.34 (1H, s), 6.66 (2H, bs), 7.50 (1H, s), 8.10 (1H, s), 10.91 (1H, bs).

Compound (IX) (3R,4R)-tert-butyl 3-hydroxy-4-(hydroxymethyl)pyrrolidine-1-carboxylate

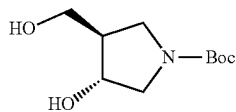

(IV)

Compound (VIII) (which can be prepared as described in WO 2005/118532) (1 g, 4.82 mmol) in ethanol (10 ml) is degassed and then treated with Pearlman's catalyst (0.1 g).

The mixture is stirred under low pressure of hydrogen and the reaction progress is monitored by TLC, more catalyst (0.1 g) is added if the reaction stalls. Once the starting N-benzyl material is consumed, the mixture is filtered through a pad of filter aid and di-t-butyl dicarbonate (1.26 g in total, 5.79 mmol) is added to the filtrate, gas evolution and a mild exotherm are observed. Once off-gassing has subsided, DMAP (13 mg) is added resulting in further off-gassing. Once gas evolution has stopped, the solvent is removed in vacuo to give 1 g of colourless oil. $\delta_H$ (500 MHz, CD$_3$OD) 1.45 (9H, s), 2.23 (1H, m), 3.21 (2H, m), 3.45 (1H, m), 3.54 (3H, m), 4.13 (1H, m).

Compound (X) (3R,4S)-tert-butyl 3-hydroxy-4-(methylthiomethyl)pyrrolidine-1-carboxylate

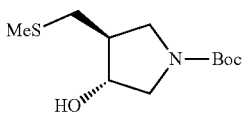
(X)

Compound (IX) (20.6 g, 0.093 mols) is isolated from an acetone solution (0.10 L) concentration in vacuo. The residue is redissolved in acetone (0.20 L) and treated with 2,6-lutidine (22.1 ml, 0.19 mols) followed by methanesulfonyl chloride (8.0 ml, 0.10 mols). The solution is stirred at 15-20° C. for two days and analysed for completion by IPC. The mixture is filtered and the solids washed with a small volume of acetone. The combined filtrates are transferred to a reaction vessel and treated with sodium thiomethoxide (8.6 g, 0.12 mols). The mixture is heated at 50° C. for 2 hours and monitored by IPC. Once complete, the reaction is concentrated and the residue partitioned between MTBE (0.2 L) and aqueous sodium hydroxide (1 M, 0.2 L). The aqueous phase is extracted once more with MTBE (0.2 L) and the combined MTBE phases are washed successively with hydrochloric acid (1 M, 0.2 L) and water (0.2 L). MTBE is removed by distillation and toluene azeotrope (0.2 L). The residue is taken up in dichloromethane/ethyl acetate (90:10, 0.11 L) and applied to a Biotage 75 S cartridge (200 g silica). The column is eluted with 90:10 dichloromethane/ethyl acetate then 66/33 dichloromethane/ethyl acetate. The fractions are assayed by TLC and the product-containing fractions are concentrated to give 14.8 g (63%) of compound (X) as a pale yellow to colourless oil. IPC analysis is performed at 205 nm using a Kinetix C18 2.6μ 100×3.0 mm column, at 40° C. with a flow rate of 0.25 ml/min and a sample concentration of 0.5 mg/ml. Solvent A is water, solvent B is acetonitrile; gradient conditions are 0-25 mins, A:B, 9:1; 25-26 mins, A:B, 4:6; 26-31 mins, A:B, 9:1. $\delta_H$ (500 MHz, CD$_3$OD) 1.46 (9H, s), 2.11 (3H, s), 2.28 (1H, m), 2.49 (1H, m), 2.63 (1H, dd, J 13.1, 6.0), 3.20 (2H, m), 3.56 (1H, m), 3.60 (1H, dd, J 11.1, 7.2), 4.10 (1H, m).

Compound (XI)
(3R,4S)-4-(methylthiomethyl)pyrrolidin-3-ol
Oxalate Salt

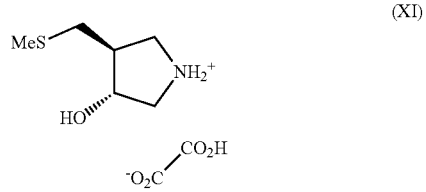
(XI)

Compound (X) (7.24 g, 29.3 mmol) is dissolved in toluene (50 ml) and concentrated. The residue is redissolved in toluene (50 ml, AR grade) and the solution cooled to 0° C. TFA (25 ml) is added with stirring, resulting in steady gas evolution. After 20 minutes, the temperature is raised to 20° C., and the mixture may become biphasic. Once off-gassing has stopped after approximately 40 minutes, the solvents are removed in vacuo and any residual solvent is azeotroped with IPA (40 ml). The residue is redissolved in IPA (75 ml, AR grade) and slurried with Amberlite FPA91 basic resin (60 g wet weight) for 30 minutes. The pH of solution is verified as ≥7. The slurry is applied to a column of FPA91 resin (20 g) and eluted with IPA (350 ml) under gravity. The IPA is evaporated to give the 5 g of free base as a brown oil. The oil is dissolved in ethanol (50 ml) and added slowly, with stirring, to a solution of oxalic acid (4.06 g, 32.1 mmol) in absolute ethanol (50 ml). After complete addition, the crystal slurry is aged for at least 2 hours and the crystals collected by filtration. The crystals are washed with ethanol (20 ml) and dried to give a white to off-white solid, 5.5 g (79%). $\delta_H$ (500 MHz, d$^6$-DMSO) 2.07 (3H, s), 2.32 (1H, m), 2.41 (1H, dd, J 13.2, 9.0), 2.60 (1H, dd, J 13.2, 6.4), 3.01 (2H, m), 3.31 (1H, dd, J 12.2, 5.1), 3.40 (1H, dd, J 11.8, 7.3), 4.13 (1H, m).

Compound (XII)
(3R,4S)-4-(methylthiomethyl)pyrrolidin-3-ol

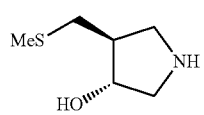
(XII)

Compound (XI) (4.0 g, 16.9 mmol) in water (80 ml) is slurried with Amberlite FPA91 resin (15 g) for 30 minutes. The slurry is applied to a column of FPA91 resin (15 g) and eluted with water (200 ml) under gravity, as required to bring off the product. Removal of water at 40° C. gives 2.68 g of orange oil, which is solidifies on storage at −20° C. GC is performed using an Rtx-5 amine capillary column 1μ, 30 m×0.32 mm, with a flow rate of 2.6 ml/min, at 100° C. then a gradient of at 8° C./min for 25 mins. $\delta_H$ (500 MHz, CD$_3$OD) 2.11 (3H, s), 2.19 (1H, m), 2.43 (1H, dd, J 13.0, 8.7), 2.64 (2H, m), 2.78 (1H, dd, J 12.1, 3.5), 3.01 (1H, dd, J 12.1, 5.5), 3.23 (1H, dd, J 11.6, 7.6), 4.05 (1H, m).

Compound (Ia) (3R,4S)-1-((4-amino-5H-pyrrolo[3,2-d]pyrimidin-7-yl)methyl)-4-(methylthiomethyl)pyrrolidin-3-ol Phosphate

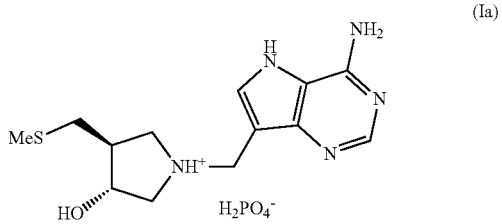

Compound (XII) (15.6 g, 106 mmol) as a solution in water/ethanol (4:1, 375 ml) is treated with compound (VII) (12.8 g, 95.4 mmol) and formaldehyde solution (8.66 ml, 35%). The mixture is stirred at approximately 20° C. for 24 hours and monitored by IPC until the starting material is consumed. Phosphoric acid (9.35 ml, 138 mmol) is added with stirring. A precipitate begins to form. After 30 mins ethanol (200 ml) is slowly added to the vessel and the mixture aged for 1 h, further ethanol (300 ml) is added and the mixture aged for 1 h. Then more ethanol (300 ml) is added and the mixture is allowed to stand overnight. The crystals are collected by filtration and are washed with ethanol/water (4/6, 200 ml), followed by ethanol (2×200 ml), and dried under vacuum to give 36.4 g (97%) of product as a white to off-white solid. IPC is performed using a Waters T3 3μ 150×4.6 mm, at 35° C. with a flow rate of 0.8 ml/min and a sample concentration of 0.5 mg/ml at a wavelength of 273 nm. Solvent A is water+0.1% TFA and solvent B is acetonitrile+0.1% TFA; gradient conditions are 0-25 mins, A:B, 9.5:0.5; 20-21 mins, A:B, 7.8:2.2; 21-26 mins, A:B, 9.5:0.5. This material is dissolved in hot water (150 ml) and methanol (500 ml) is added slowly keeping the solution at boiling point and then allowed to cool. The product is collected by filtration and washed with methanol to give 33.0 g (88%). Anal. Calc. for $C_{13}H_{19}N_5OS \cdot 1.4H_3PO_4 \cdot H_2O$; C, 34.8; H, 5.7; N, 15.6; P, 9.7. Found: C, 34.5; H, 5.6; N, 15.5; P, 9.9. $\delta^{13}C$ NMR (D$_2$O) 150.1, 146.6, 140.4, 133.7, 113.0, 102.5, 72.8, 58.5, 55.5, 47.6, 44.9, 34.0, 14.4.

(3R,4S)-1-((4-amino-5H-pyrrolo[3,2-d]pyrimidin-7-yl)methyl)-4-(methylthiomethyl)pyrrolidin-3-ol Phosphate Form D Compound (XII) (2.48 g, 16.9 mmol) is stirred in water/ethanol (4:1, 80 ml) and treated with 9-deazaadenine (2.06 g, 15.3 mmol) and formaldehyde solution (1.11 ml, 38%). The mixture is stirred at ambient temperature for 2 days. A solution of phosphoric acid (2.25 g, 23.0 mmol) in water (10 ml) is prepared. A portion of this solution (6 ml) is slowly added to the mixture with stirring. Seed crystals (76 mg) are added and the mixture aged for 1 h. The remaining acid solution is slowly charged with stirring; the mixture is aged for 1 h. Ethanol (35 ml) is slowly charged to the vessel and the mixture aged for 1 h. Further ethanol (60 ml) is slowly charged to the vessel and the mixture aged for 1 h. The mixture is filtered and the crystals washed with ethanol/water (40/60, 25 ml), followed by ethanol (2×25 ml). The crystals are dried under vacuum to give the product as a white to off-white solid, 4.7 g (70%).

(3R,4S)-1-((4-amino-5H-pyrrolo[3,2-d]pyrimidin-7-yl)methyl)-4-(methylthiomethyl)pyrrolidin-3-ol Phosphate Form E (3R,4S)-1-((4-amino-5H-pyrrolo[3,2-d]pyrimidin-7-yl)methyl)-4-(methylthiomethyl)pyrrolidin-3-ol phosphate (1 g) is stirred in water (18 ml) and heated to 40° C. to dissolve. Ethanol (2 ml) is added along with (3R,4S)-1-((4-amino-5H-pyrrolo[3,2-d]pyrimidin-7-yl)methyl)-4-(methylthiomethyl)pyrrolidin-3-ol phosphate seed crystals (25 mg). The resulting mixture is cooled to approximately 15° C. After 1 h ethanol (5 ml) is added to the stirred solution. After a further 1 h ethanol (10 ml) is added to the stirred solution. After a further 1 h ethanol (15 ml) is added and the slurry stirred overnight. The mixture is filtered on filter paper and the crystals washed with ethanol (approximately 10 ml). The crystals are dried under vacuum giving 775 mg white solid.

(3R,4S)-1-((4-amino-5H-pyrrolo[3,2-d]pyrimidin-7-yl)methyl)-4-(methylthiomethyl)pyrrolidin-3-ol Phosphate Form F (3R,4S)-1-((4-amino-5H-pyrrolo[3,2-d]pyrimidin-7-yl)methyl)-4-(methylthiomethyl)pyrrolidin-3-ol phosphate (36.3 g) is dissolved in boiling water (150 mL) and methanol (500 ml) is added slowly while maintaining reflux of the solution. The resulting mixture is cooled to 15° C. and agitated for 18 hours. The resulting crystals are filtered, washed with methanol (approx. 50 ml) and dried to give a white solid, 33.0 g (91%).

Example 2: Sulfate, Oxalate and Formate Salts of Compound (I)

(3R,4S)-1-((4-amino-5H-pyrrolo[3,2-d]pyrimidin-7-yl)methyl)-4-(methylthiomethyl)pyrrolidin-3-ol Compound (XII) (457 mg, 3.10 mmol) is stirred in water/ethanol (4:1, 22.5 ml) and treated with 9-deazaadenine (378 mg, 2.82 mmol) and formaldehyde solution (0.21 ml, 38%). The mixture is stirred at ambient temperature for 3 days. A solution of sulfuric acid (2.8 ml, 1M) is added. Ethanol (5 ml) is added. The mixture is cooled to 0° C. and stirred for 15 minutes. The resulting slurry is filtered and the crystals dried to give 548 mg tan solid. A portion of this solid (300 mg) is stirred in water (approximately 10 ml) with Amberlite FPA91-OH resin (approximately 2 g) for 30 minutes. The resin is filtered and the solution evaporated to give 143 mg white solid ((3R,4S)-1-((4-amino-5H-pyrrolo[3,2-d]pyrimidin-7-yl)methyl)-4-(methylthiomethyl)pyrrolidin-3-ol which is used in the next steps).

(3R,4S)-1-((4-amino-5H-pyrrolo[3,2-d]pyrimidin-7-yl)methyl)-4-(methylthiomethyl)pyrrolidin-3-ol Sulfate (3R,4S)-1-((4-amino-5H-pyrrolo[3,2-d]pyrimidin-7-yl)methyl)-4-(methylthiomethyl)pyrrolidin-3-ol (50 mg, 0.17 mmol) is dissolved in water (1.0 ml) and treated with sulfuric acid (0.17 ml, 1M, 1.0 eq). IPA (0.4 ml) is added and the resulting solution stored at 4° C. resulting in formation of an oil phase. The mixture is warmed to give a solution, treated with ethanol (approximately 0.2 ml) and stored at 4° C. overnight resulting in precipitation of solids from solution. The solid is filtered on filter paper and dried under vacuum.

(3R,4S)-1-((4-amino-5H-pyrrolo[3,2-d]pyrimidin-7-yl)methyl)-4-(methylthiomethyl)pyrrolidin-3-ol Oxalate (3R,4S)-1-((4-amino-5H-pyrrolo[3,2-d]pyrimidin-7-yl) methyl)-4-(methylthiomethyl)pyrrolidin-3-ol (50 mg, 0.17 mmol) is dissolved in water (1.0 ml) and treated with oxalic acid dihydrate (22 mg, 0.17 mmol). IPA (0.4 ml) is added and the resulting solution stored at 4° C. resulting in formation of solids. The solid is filtered on filter paper and dried under vacuum.

3R,4S)-1-((4-amino-5H-pyrrolo[3,2-d]pyrimidin-7-yl)methyl)-4-(methylthiomethyl)pyrrolidin-3-ol Formate (3R,4S)-1-((4-amino-5H-pyrrolo[3,2-d]pyrimidin-7-yl) methyl)-4-(methylthiomethyl)pyrrolidin-3-ol (0.983 g, 3.35 mmol) is suspended in water (3 ml) and formic acid (0.25 ml, 6.70 mmol) is added. The mixture is warmed to approximately 40° C. to dissolve. Ethanol (approx. 10 ml) is added. The mixture is evaporated to dryness and re-suspended in water (2 ml) and acetone added (approx. 30 ml) resulting in formation of pale yellow crystals (0.71 g). A portion of this material (0.65 g) is dissolved in water (2.5 ml) and diluted with acetone (30 ml). The resulting crystals are filtered and dried to give 0.55 g (52% yield from the free base) cream coloured solid.

Example 3: X-Ray Powder Diffraction Data for Compounds of the Invention

(3R,4S)-1-((4-amino-5H-pyrrolo[3,2-d]pyrimidin-7-yl)methyl)-4-(methylthiomethyl)pyrrolidin-3-ol Phosphate Form D

| 2-theta degrees | d value Angstrom | Intensity Count |
|---|---|---|
| 5.38 | 19.075 | 283 |
| 7.10 | 14.448 | 103 |
| 8.93 | 11.487 | 137 |
| 10.87 | 9.443 | 104 |
| 13.06 | 7.865 | 84.2 |
| 14.31 | 7.181 | 85.8 |
| 14.57 | 7.053 | 58.7 |
| 15.32 | 6.709 | 70.4 |
| 15.81 | 6.504 | 152 |
| 16.50 | 6.232 | 88.7 |
| 17.59 | 5.849 | 256 |
| 17.92 | 5.742 | 357 |
| 19.07 | 5.4 | 72.6 |
| 19.97 | 5.159 | 175 |
| 20.17 | 5.108 | 105 |
| 20.77 | 4.963 | 112 |
| 21.53 | 4.789 | 397 |
| 21.78 | 4.734 | 355 |
| 22.22 | 4.643 | 144 |
| 22.76 | 4.534 | 267 |
| 23.12 | 4.463 | 161 |
| 24.84 | 4.159 | 145 |
| 25.75 | 4.014 | 653 |
| 26.00 | 3.977 | 722 |
| 26.31 | 3.931 | 392 |
| 27.06 | 3.823 | 283 |
| 27.79 | 3.725 | 265 |
| 28.14 | 3.679 | 211 |
| 28.57 | 3.625 | 202 |
| 28.95 | 3.579 | 296 |
| 29.35 | 3.531 | 302 |
| 29.97 | 3.459 | 299 |
| 30.50 | 3.401 | 217 |
| 30.91 | 3.357 | 305 |
| 31.35 | 3.311 | 305 |
| 32.64 | 3.183 | 217 |
| 32.09 | 3.236 | 351 |
| 34.17 | 3.045 | 204 |
| 33.33 | 3.119 | 150 |

(3R,4S)-1-((4-amino-5H-pyrrolo[3,2-d]pyrimidin-7-yl)methyl)-4-(methylthiomethyl)pyrrolidin-3-ol Phosphate Form E

| 2-theta degrees | d value Angstrom | Intensity Count |
|---|---|---|
| 5.26 | 19.479 | 667 |
| 7.01 | 14.623 | 100 |
| 8.69 | 11.801 | 133 |
| 8.90 | 11.522 | 87.2 |
| 10.58 | 9.704 | 283 |
| 12.56 | 8.177 | 67 |
| 15.95 | 6.446 | 93 |
| 16.76 | 6.136 | 117 |
| 17.26 | 5.962 | 439 |
| 17.57 | 5.857 | 367 |
| 17.84 | 5.77 | 193 |
| 19.36 | 5.319 | 73 |
| 20.14 | 5.115 | 102 |
| 20.86 | 4.942 | 146 |
| 21.27 | 4.846 | 404 |
| 21.60 | 4.773 | 408 |
| 22.09 | 4.669 | 126 |
| 22.52 | 4.58 | 241 |
| 22.75 | 4.536 | 322 |
| 23.03 | 4.481 | 146 |
| 24.14 | 4.278 | 82 |
| 25.64 | 4.031 | 714 |
| 25.95 | 3.984 | 606 |
| 26.16 | 3.952 | 516 |
| 26.63 | 3.884 | 247 |
| 26.88 | 3.849 | 348 |
| 27.72 | 3.734 | 175 |
| 28.86 | 3.589 | 380 |
| 29.35 | 3.531 | 220 |
| 29.99 | 3.457 | 541 |
| 30.22 | 3.431 | 383 |
| 30.75 | 3.374 | 431 |
| 31.11 | 3.336 | 242 |
| 31.57 | 3.288 | 294 |
| 32.38 | 3.208 | 173 |
| 33.04 | 3.146 | 242 |
| 33.38 | 3.115 | 180 |
| 33.92 | 3.066 | 224 |

(3R,4S)-1-((4-amino-5H-pyrrolo[3,2-d]pyrimidin-7-yl)methyl)-4-(methylthiomethyl)pyrrolidin-3-ol Phosphate Form F

| 2-theta degrees | d value Angstrom | Intensity % |
|---|---|---|
| 5.25 | 19.534 | 71 |
| 7.00 | 14.654 | 21.5 |
| 8.73 | 11.758 | 32.4 |
| 8.92 | 11.500 | 14.2 |
| 10.67 | 9.620 | 29.4 |

| 2-theta degrees | d value Angstrom | Intensity % |
|---|---|---|
| 12.69 | 8.091 | 10.9 |
| 14.18 | 7.245 | 8.8 |
| 15.14 | 6.790 | 5.4 |
| 15.82 | 6.500 | 12.5 |
| 16.03 | 6.413 | 12 |
| 16.68 | 6.167 | 7.5 |
| 17.52 | 5.873 | 50.7 |
| 17.75 | 5.797 | 53.7 |
| 19.21 | 5.360 | 2.6 |
| 20.13 | 5.118 | 14.2 |
| 20.77 | 4.962 | 12 |
| 21.36 | 4.827 | 46.9 |
| 21.72 | 4.748 | 36.9 |
| 22.09 | 4.669 | 8.9 |
| 22.79 | 4.527 | 40.3 |
| 23.60 | 4.374 | 5.3 |
| 24.35 | 4.241 | 5.1 |
| 24.80 | 4.165 | 6.2 |
| 25.70 | 4.022 | 100 |
| 26.10 | 3.962 | 74.2 |
| 26.80 | 3.859 | 22.5 |
| 27.00 | 3.832 | 18.2 |
| 27.81 | 3.722 | 11.3 |
| 28.55 | 3.627 | 42.5 |
| 29.01 | 3.571 | 12.7 |
| 29.56 | 3.506 | 27.5 |
| 29.88 | 3.469 | 17.1 |
| 30.52 | 3.398 | 45.1 |
| 31.42 | 3.303 | 21.9 |
| 32.12 | 3.233 | 18.5 |
| 32.42 | 3.204 | 31.4 |
| 32.95 | 3.154 | 15.2 |
| 33.68 | 3.088 | 4.8 |
| 34.08 | 3.052 | 9.9 |
| 35.08 | 2.968 | 5.6 |
| 35.84 | 2.907 | 7.9 |
| 36.58 | 2.850 | 3.3 |
| 37.32 | 2.795 | 5.1 |
| 39.18 | 2.668 | 2.7 |
| 40.37 | 2.592 | 4 |
| 40.79 | 2.567 | 3.1 |
| 41.84 | 2.505 | 3.5 |
| 42.56 | 2.464 | 3 |
| 43.62 | 2.408 | 2.6 |
| 44.51 | 2.362 | 2.1 |
| 46.14 | 2.283 | 2.9 |
| 46.52 | 2.265 | 3.3 |
| 47.00 | 2.243 | 1.9 |
| 48.23 | 2.189 | 1.8 |
| 49.02 | 2.156 | 2.3 |
| 49.54 | 2.135 | 2.3 |

(3R,4S)-1-((4-amino-5H-pyrrolo[3,2-d]pyrimidin-7-yl)methyl)-4-(methylthiomethyl)pyrrolidin-3-ol Oxalate

| 2-theta degrees | d value Angstrom | Intensity Count |
|---|---|---|
| 6.22 | 16.498 | 364 |
| 12.35 | 8.318 | 104 |
| 13.54 | 7.588 | 152 |
| 14.94 | 6.881 | 94 |
| 15.72 | 6.542 | 81.6 |
| 18.22 | 5.648 | 148 |
| 19.11 | 5.388 | 100 |
| 20.47 | 5.034 | 134 |
| 21.94 | 4.7 | 134 |
| 22.53 | 4.578 | 103 |
| 24.22 | 4.263 | 114 |
| 29.44 | 3.52 | 149 |
| 30.07 | 3.448 | 130 |
| 31.11 | 3.336 | 115 |
| 32.06 | 3.239 | 145 |
| 32.71 | 3.177 | 115 |
| 33.90 | 3.068 | 86.1 |

(3R,4S)-1-((4-amino-5H-pyrrolo[3,2-d]pyrimidin-7-yl)methyl)-4-(methylthiomethyl)pyrrolidin-3-ol Formate

| 2-theta degrees | d value Angstrom | Intensity % |
|---|---|---|
| 8.11 | 12.650 | 100.0 |
| 10.34 | 9.927 | 1.7 |
| 13.66 | 7.522 | 2.3 |
| 16.30 | 6.311 | 54.6 |
| 17.54 | 5.868 | 6.5 |
| 17.94 | 5.735 | 5.0 |
| 18.83 | 5.469 | 0.8 |
| 20.68 | 4.983 | 34.0 |
| 21.32 | 4.835 | 5.0 |
| 21.71 | 4.749 | 1.2 |
| 23.17 | 4.454 | 2.9 |
| 24.63 | 4.194 | 9.7 |
| 24.85 | 4.157 | 33.3 |
| 25.70 | 4.022 | 19.2 |
| 26.03 | 3.972 | 8.9 |
| 27.13 | 3.814 | 1.8 |
| 27.57 | 3.754 | 6.1 |
| 28.00 | 3.698 | 14.4 |
| 28.51 | 3.632 | 7.7 |
| 28.77 | 3.600 | 6.6 |
| 30.32 | 3.420 | 6.2 |
| 31.05 | 3.342 | 3.3 |
| 31.24 | 3.322 | 4.0 |
| 32.23 | 3.223 | 14.0 |
| 33.02 | 3.147 | 10.1 |
| 33.45 | 3.108 | 1.7 |
| 34.24 | 3.039 | 5.1 |
| 34.52 | 3.014 | 3.3 |
| 35.57 | 2.929 | 1.4 |
| 35.99 | 2.896 | 1.9 |
| 36.65 | 2.845 | 4.7 |
| 36.92 | 2.825 | 1.2 |
| 38.15 | 2.737 | 0.9 |
| 38.90 | 2.686 | 2.6 |
| 39.94 | 2.619 | 3.7 |
| 40.47 | 2.586 | 0.6 |
| 41.45 | 2.528 | 3.6 |
| 42.17 | 2.486 | 3.9 |
| 42.75 | 2.454 | 0.9 |
| 44.36 | 2.369 | 1.0 |
| 45.14 | 2.330 | 1.4 |
| 46.27 | 2.277 | 4.2 |
| 46.50 | 2.266 | 2.8 |
| 47.36 | 2.227 | 2.5 |
| 48.48 | 2.178 | 1.3 |
| 49.20 | 2.149 | 0.4 |
| 50.12 | 2.112 | 2.5 |

(3R,4S)-1-((4-amino-5H-pyrrolo[3,2-d]pyrimidin-7-yl)methyl)-4-(methylthiomethyl)pyrrolidin-3-ol Sulfate

| 2-theta degrees | d value Angstrom | Intensity Count |
|---|---|---|
| 5.75 | 17.828 | 233 |
| 10.33 | 9.936 | 111 |
| 13.14 | 7.818 | 114 |
| 15.41 | 6.672 | 93.3 |
| 15.90 | 6.469 | 151 |
| 17.61 | 5.844 | 121 |
| 18.32 | 5.619 | 103 |
| 19.14 | 5.38 | 79.4 |
| 20.27 | 5.082 | 79.4 |
| 20.87 | 4.939 | 87.7 |
| 21.43 | 4.811 | 104 |
| 22.26 | 4.633 | 82.8 |
| 24.30 | 4.25 | 131 |
| 24.64 | 4.192 | 87.3 |
| 26.15 | 3.954 | 93.3 |
| 26.76 | 3.866 | 103 |
| 27.67 | 3.741 | 94.9 |
| 29.37 | 3.529 | 69.8 |
| 30.28 | 3.425 | 115 |
| 30.97 | 3.35 | 136 |
| 31.52 | 3.293 | 120 |
| 32.27 | 3.219 | 103 |
| 33.24 | 3.127 | 84.2 |

Example 4: Activity of (3R,4S)-1-((4-amino-5H-pyrrolo[3,2-d]pyrimidin-7-yl)methyl)-4-(methylthiomethyl)pyrrolidin-3-ol Phosphate Against Head and Neck Cancers, Lung Cancer, Breast Cancer, Colon Cancer, Cervical Cancer or Prostate Cancer Female Ncr-Nu mice (6-8 weeks old) are obtained from NCI, NIH. Animal experiments are conducted in accordance with approved protocol guidelines of the Animal Committee of the Albert Einstein College of Medicine. Orthotopic mammary fat pad injections are performed at two opposite inguinal fat pad of each mouse by re-suspending $2.5 \times 10^6$ MDA-MB-468 viable cells in 75 ml of PBS and mixing with 25 ml of rat tail collagen, type I (BD) per site. At day 36, mice with established tumours (~150 mm³) are randomly assigned to treatment or control groups of five animals each followed by treatment with (3R,4S)-1-((4-amino-5H-pyrrolo[3,2-d]pyrimidin-7-yl)methyl)-4-(methylthiomethyl)pyrrolidin-3-ol phosphate at 30.5 mg/kg body weight in drinking water or by daily intraperitoneal (i.p.) injections of 24 mg/kg body weight with and without 13 mg/kg methylthioadenosine. Tumour volume (V) is determined as follows: $V=(4/3) \times (22/7) \times \frac{1}{8}(\text{length} \times \text{width} \times \text{height})$. Differences between treatment cohorts are determined using the Student's t test. Mice are weighed every 4-5 days, monitored for hair loss, loss of appetite, vomiting, and diarrhea. Untreated control tumours grow from 150 to 400 mm³ over a period of 35 days. Doses of (3R,4S)-1-((4-amino-5H-pyrrolo[3,2-d]pyrimidin-7-yl)methyl)-4-(methylthiomethyl) pyrrolidin-3-ol phosphate from 24 to 30.5 mg/kg are equally effective at stopping cancer growth. At day 71, animals being treated are released from therapy to see if regrowth equals untreated tumour growth. Conversely, animals with the large control tumours are treated with 30 mg/kg i.p. (3R,4S)-1-((4-amino-5H-pyrrolo[3,2-d]pyrimidin-7-yl)methyl)-4-(methylthiomethyl)pyrrolidin-3-ol phosphate. During treatment, (3R,4S)-1-((4-amino-5H-pyrrolo[3,2-d]pyrimidin-7-yl)methyl)-4-(methylthiomethyl)pyrrolidin-3-ol phosphate completely suppresses tumour growth in the 150 mm³ tumours. Upon drug release, tumour size increases slowly relative to untreated tumour growth. The large tumours undergo rapid decrease in size as a consequence of tumour lysis. The bulk of the tumours resolve over a two-week treatment period.

Although the invention has been described in connection with specific preferred embodiments, it should be understood that the invention as claimed should not be unduly limited to such specific embodiments.

It is appreciated that further modifications may be made to the invention as described herein without departing from the spirit and scope of the invention.

The invention claimed is:

1. A process for preparing a compound of formula (V)

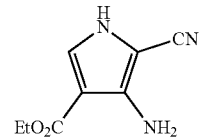

(V)

including the steps:

(d) reacting a compound of formula (III) with methyl chloroformate to produce a compound of formula (IV)

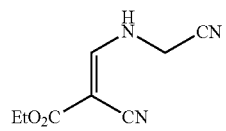

(III)

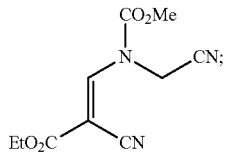

(IV)

and (e) cyclisation of the compound of formula (IV) under basic conditions to give the compound of formula (V); wherein ethyl acetate is employed as a solvent in step (d).

* * * * *